United States Patent
Garikipati et al.

(10) Patent No.: US 9,873,652 B2
(45) Date of Patent: Jan. 23, 2018

(54) PROCESS AND SYSTEMS FOR OBTAINING 1,4-BUTANEDIOL FROM FERMENTATION BROTHS

(71) Applicant: Genomatica, Inc., San Diego, CA (US)

(72) Inventors: SVB Janardhan Garikipati, San Diego, CA (US); Michael Japs, San Diego, CA (US); Ishmael M. Sonico, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 0 days.

(21) Appl. No.: 14/776,517

(22) PCT Filed: Mar. 14, 2014

(86) PCT No.: PCT/US2014/027593
§ 371 (c)(1),
(2) Date: Sep. 14, 2015

(87) PCT Pub. No.: WO2014/152665
PCT Pub. Date: Sep. 25, 2014

(65) Prior Publication Data
US 2016/0031778 A1 Feb. 4, 2016

Related U.S. Application Data

(60) Provisional application No. 61/801,107, filed on Mar. 15, 2013, provisional application No. 61/829,625, (Continued)

(51) Int. Cl.
*C07C 29/80* (2006.01)
*C07C 29/74* (2006.01)
(Continued)

(52) U.S. Cl.
CPC .............. *C07C 29/80* (2013.01); *B01D 1/22* (2013.01); *B01D 3/002* (2013.01); *B01D 3/143* (2013.01);
(Continued)

(58) Field of Classification Search
CPC ....... C07C 29/80; C07C 29/00; C07C 31/207; C07C 29/90; C07C 29/74; C12P 7/18; B01D 3/002; B01D 1/22; B01D 3/143
See application file for complete search history.

(56) References Cited

U.S. PATENT DOCUMENTS 3,976,430 A 8/1976 Houston et al.
4,032,458 A * 6/1977 Cooley ............... C07C 29/177
560/190

(Continued)

FOREIGN PATENT DOCUMENTS

CA 2226534 A 7/1998
CA 2841059 A1 1/2013
(Continued)

OTHER PUBLICATIONS

Cvengros et al. "Evaporator with wiped film as the reboiler of the vacuum rectifying column" Separation and Purification Technology 15 (1999) 95-100 published in 1999.*

(Continued)

*Primary Examiner* — Amber R Orlando
*Assistant Examiner* — Stephen Hobson
(74) *Attorney, Agent, or Firm* — Jones Day

(57) ABSTRACT

A process of purifying 1,4-butanediol (1,4-BDO) from a fermentation broth including separating solid materials, salts and water, and subjecting the resulting material to a two, three or four column distillation system, that can include a wiped film evaporator to produce a purified 1,4-butanediol product.

9 Claims, 7 Drawing Sheets

Related U.S. Application Data filed on May 31, 2013, provisional application No. 61/928,966, filed on Jan. 17, 2014.

(51) Int. Cl.

| | | |
|---|---|---|
| B01D 3/14 | (2006.01) | |
| C07C 29/90 | (2006.01) | |
| B01D 1/22 | (2006.01) | |
| B01D 3/00 | (2006.01) | |
| C07C 29/00 | (2006.01) | |
| C07C 31/20 | (2006.01) | |
| C12P 7/18 | (2006.01) | |

(52) U.S. Cl.
CPC .............. *C07C 29/00* (2013.01); *C07C 29/74* (2013.01); *C07C 29/90* (2013.01); *C07C 31/207* (2013.01); *C12P 7/18* (2013.01)

(56) References Cited

U.S. PATENT DOCUMENTS

| | | | |
|---|---|---|---|
| 4,383,895 A * | 5/1983 | Ernst | C07C 29/80 203/77 |
| 5,342,488 A * | 8/1994 | Gosch | C07C 29/80 203/80 |
| 5,608,146 A | 3/1997 | Frommer et al. | |
| 5,766,439 A | 6/1998 | Eyal et al. | |
| 5,772,890 A | 6/1998 | Hubred | |
| 5,981,810 A * | 11/1999 | Okuyama | C07C 29/78 568/854 |
| 5,986,133 A | 11/1999 | Holtzapple et al. | |
| 6,228,579 B1 | 5/2001 | Zyskind et al. | |
| 6,361,983 B1 | 3/2002 | Ames | |
| 6,515,187 B1 | 2/2003 | Schon et al. | |
| 6,846,389 B2 | 1/2005 | Kaibel et al. | |
| 7,708,865 B2 | 5/2010 | Holtzapple et al. | |
| 7,858,350 B2 | 12/2010 | Burk et al. | |
| 7,893,305 B2 * | 2/2011 | Liu | C07C 29/80 568/868 |
| 7,919,658 B2 | 4/2011 | Adkesson et al. | |
| 7,947,483 B2 | 5/2011 | Burgard et al. | |
| 8,048,661 B2 | 11/2011 | Burgard et al. | |
| 8,067,214 B2 | 11/2011 | Burk et al. | |
| 8,129,156 B2 | 3/2012 | Burk et al. | |
| 8,129,169 B2 | 3/2012 | Van Dien et al. | |
| 8,178,327 B2 | 5/2012 | Burk et al. | |
| 8,183,417 B2 | 5/2012 | Adkesson et al. | |
| 8,357,520 B2 | 1/2013 | Burk et al. | |
| 8,377,666 B2 | 2/2013 | Haselbeck et al. | |
| 8,377,667 B2 | 2/2013 | Haselbeck et al. | |
| 8,445,244 B2 | 5/2013 | Burgard et al. | |
| 8,470,582 B2 | 6/2013 | Burgard et al. | |
| 8,530,210 B2 | 9/2013 | Sun et al. | |
| 8,597,918 B2 | 12/2013 | Clark et al. | |
| 9,464,030 B2 * | 10/2016 | Fruchey | C07C 29/149 |
| 2003/0106786 A1 | 6/2003 | Kaibel et al. | |
| 2003/0203459 A1 | 10/2003 | Chen et al. | |
| 2003/0233218 A1 | 12/2003 | Schilling | |
| 2005/0069997 A1 | 3/2005 | Adkesson et al. | |
| 2005/0221466 A1 | 10/2005 | Liao et al. | |
| 2006/0041152 A1 | 2/2006 | Cantrell et al. | |
| 2009/0023182 A1 | 1/2009 | Schilling | |
| 2009/0047719 A1 | 2/2009 | Burgard et al. | |
| 2009/0075351 A1 | 3/2009 | Burk et al. | |
| 2009/0275096 A1 | 11/2009 | Burgard et al. | |
| 2010/0101931 A1 * | 4/2010 | Pinkos | C07C 29/80 203/82 |
| 2010/0317902 A1 | 12/2010 | Liu et al. | |
| 2010/0330634 A1 | 12/2010 | Park et al. | |
| 2011/0003355 A1 * | 1/2011 | Clark | C07C 29/76 435/158 |
| 2011/0014669 A1 | 1/2011 | Madden et al. | |
| 2011/0129904 A1 | 6/2011 | Burgard et al. | |
| 2011/0152581 A1 | 6/2011 | Adkesson et al. | |
| 2011/0201068 A1 | 8/2011 | Pharkya et al. | |
| 2011/0212507 A1 | 9/2011 | Burgard et al. | |
| 2011/0257441 A1 | 10/2011 | Rousseaux et al. | |
| 2012/0094345 A1 | 4/2012 | Burk et al. | |
| 2012/0225463 A1 | 9/2012 | Van Dien et al. | |
| 2012/0277484 A1 * | 11/2012 | Warner | C07C 29/149 568/884 |
| 2013/0035523 A1 * | 2/2013 | Lee | B01D 3/148 568/885 |
| 2013/0196397 A1 | 8/2013 | Burk et al. | |
| 2014/0116872 A1 | 5/2014 | Izawa et al. | |
| 2014/0121390 A1 | 5/2014 | Izawa et al. | |
| 2014/0135511 A1 | 5/2014 | Izawa et al. | |
| 2014/0275465 A1 * | 9/2014 | Garikipati | C07C 29/80 528/68 |
| 2015/0087038 A1 * | 3/2015 | Utsunomiya | C07C 29/80 435/158 |
| 2016/0031778 A1 * | 2/2016 | Garikipati | B01D 3/143 435/158 |

FOREIGN PATENT DOCUMENTS

| | | | | |
|---|---|---|---|---|
| CN | 102161615 B | * | 6/2013 | |
| CN | 104640830 A | | 5/2015 | |
| DE | 102005042541 A1 | | 3/2007 | |
| DE | 102007048277 A1 | | 4/2009 | |
| EP | 2730566 A1 | | 5/2014 | |
| JP | A-S62-285779 | | 4/1986 | |
| WO | 2004101479 A2 | | 11/2004 | |
| WO | 2007030830 A2 | | 3/2007 | |
| WO | 2008115840 A2 | | 9/2008 | |
| WO | 2009023493 A1 | | 2/2009 | |
| WO | 2009094485 A1 | | 7/2009 | |
| WO | 2010006076 A2 | | 1/2010 | |
| WO | 2010141780 A1 | | 12/2010 | |
| WO | 2011137192 A1 | | 11/2011 | |
| WO | WO 2012125276 A2 | * | 9/2012 | ............. C07B 63/00 |
| WO | 2013012047 A1 | | 1/2013 | |
| WO | 2013012048 A1 | | 1/2013 | |
| WO | 2013015290 A1 | | 1/2013 | |
| WO | 2013034881 A1 | | 3/2013 | |
| WO | 2013005747 A1 | | 10/2013 | |
| WO | 2014152665 A1 | | 9/2014 | |

OTHER PUBLICATIONS

Yavorsky, D., et al., "The clarification of bioreactor cell cultures for biopharmaceuticals," Pharmacology Technology (2003), pp. 62-76.
Schaep, J., "Modelling the retention of ionic components for different nanofiltration membranes," Separation and Purification Technology, (2001), pp. 22-23 and 169-179.
International Searching Authority, "Written Opinion for International Application No. PCT/US2014/027593," (dated Jul. 14, 2014), 3 pages.
Kobayashi et al., "Fermentative Production of 1,4-Butanediol from Sugars by *Bacillus* sp.," Agric. Biol. Chern., (1987), vol. 51, Issue 6, pp. 1689-1690.
Ahmed and Lewis, "Fermentation of biomass-generated synthesis gas: effects of nitric oxide," Biotechnol. Bioeng. (2007), vol. 97, pp. 1080-1086.
Atsumi et al., "Non-fermentative pathways for synthesis of branched-chain higher alcohols as biofuels," Nature (2008), vol. 451, Issue 7174, pp. 86-89.
Cukalovic et al., "Feasibility of production method for succinic acid derivatives: a marriage of renewable resources and chemical technology," Biofuels Bioprod. Bioref. (2008), vol. 2, pp. 505-529.
Datar et al., "Fermentation of biomass-generated producer gas to ethanol," Biotechnol. Bioeng, (2004), vol. 86, pp. 587-594.
Durre and Bahl, "Microbial Production of Acetone/Butanol/Isopropanol," In Biotechnology, vol. 6: "Products of Primary Metabolism", Second edition, M. Roehr, ed. Published jointly by: VCH Verlagsgesellschaft mbH, Weinheim, Federal Republic of Germany and VCH Publishers Inc., New York, NY (1996). pp. 229-268.
Forster et al., "Genome-scale reconstruction of the *Saccharomyces cerevisiae* metabolic network," Genome Res. (2003), vol. 13, pp. 244-253.

(56) References Cited

OTHER PUBLICATIONS

Gerhardt et al., "Fermentation of 4-aminobutyrate by Clostridium aminobutyricum: cloning of two genes involved in the formation and dehydration of 4-hydroxybutyryi-CoA," Arch. Microbial., (2000), vol. 174, pp. 189-199.

Gong et al., "Effects of transport properites of ion-exchange membranes on desalination of 1,3-propanediol fermentation broth by electrodialysis," Desalination, (2006), vol. 191, pp. 193-199.

Hanai et al., "Engineered synthetic pathway for isopropanol production in *Escherichia coli*," Appl. Environ. Microbial. (2007), vol. 73, pp. 7814-7818.

Hein et al., "Biosynthesis of poly(4-hydroxybutyric acid) by recombinant strains of *Escherichia coli*," FEMS Microbial., Lett., (1997), vol. 153, Issue 2, pp. 411-418.

Ichikawa et al. "Catalytic reaction of 1,3-butanediol over solid acids," J. Mol. Catalysis A Chem., (2006), vol. 256, pp. 106-112.

Ichikawa et al., "PIO study on 1,3-butanediol dehydration over Ce02 (1 1 1) surface," J. Mol. Catalvsis A Chem., (2005), vol. 231, pp. 181-189.

Jojima et al., "Production of isopropanol by metabolically engineered *Escherichia coli*," Appl. Microbial. Biotechnol., (2008), vol. 77, pp. 1219-1224.

Jones and Woods, "Acetone-butanol fermentation revisited," Microbial. Rev., (1986), vol. 50, Issue 4, pp. 484-524.

Kato et al., "Production of a novel copolyester of 3-hydroxybutyric acid with a medium-chain-length 3-hydroxyalkanoic acids by *Pseudomonas* sp. 61-3 from sugars," Appl. Microbial. Biotechnol., (1996), vol. 45, pp. 363-370.

Kim et al., "Construction of an *Escherichia coli* K-12 mutant for homoethanologenic fermentation of glucose or xylose without foreign genes," Appl. Environ. Microbial., (2007), vol. 73, pp. 1766-1771.

Lee et al., "Biosynthesis of enantiopure (s)-3-hydroxybutyric acid in metabolically engineered *Escherichia coli*," Appl. Microbial. Biotechnol., (2008), vol. 79, Issue 4, pp. 633-641.

Lee et al., "Biosynthesis of copolyesters consisting of 3-hydroxybutyric acid and medium-chain-length 3-hydroxyalkanoic acids from 1,3-butanediol or from 3-hydroxybutyrate by *Pseudomonas* sp. A33," Appl. Microbial. Biotechnol., (1995), vol. 42, pp. 901-909.

Lin et al., "Fed-batch culture of a metabolically engineered *Escherichia coli* strain designed for high-level succinate production and yield under aerobic conditions," Biotechnol. Bioeng., (2005), vol. 90, Issue 6, pp. 775-779.

Mahadevan et al., "Application of metabolic modeling to drive bioprocess development for the production of value-added chemicals," Biotechnol. Bioprocess Eng., (2005), vol. 10, Issue 5, pp. 408-417.

Mahadevan and Schilling, "The effects of alternate optimal solutions in constraint based genome-scale metabolic models," Metab. Eng., (2003), vol. 5, Issue 4, pp. 264-276.

Nakano et al., "Characterization of Anaerobic Fermentative Growth of Bacillus subtilis: Identification of Fermentation End Products and Genes Required for Growth," J. Bacterial., (1997), vol. 179, Issue 21, pp. 6749-6755.

Nexant, "1,4-Butanediol/THF—PERP Program New Report Alert," Nexant ChemSystems PERP Report 02/03-7, (Jan. 2004), pp. 1-5.

Park and Lee, "Biosynthesis of poly(3-hydroxybutyrate-co-3-hydroxyalkanoates) by metabolically engineered *Escherichia coli* strains," Appl. Biochem. Biotechnol. (2004), vol. 113-116, pp. 335-346.

Schilling et al., "Toward Metabolic Phenomics: Analysis of Genomic Data Using Flux Balances," Biotechnol. Proa., (1999), vol. 15, pp. 288-295.

Schilling et al., "Combining Pathway Analysis with Flux Balance Analysis for the Comprehensive Study of Metabolic Systems," Biotechnol. Bioeng., (2000-2001), vol. 71, Issue 4, pp. 286-306.

Schilling et al., "Theory for the Systematic Definition of Metabolic Pathways and Their Use in Interpreting Metabolic Function from a Pathway-Oriented Perspective," J. Theor. Biol., (2000), vol. 203, Issue 3, pp. 229-248.

Werpy et al., "Top Value Added Chemicals from Biomass. Volume I—Results of Screening for Potential Candidates from Sugars and Synthesis Gas," (2004), DOE Report.

European Patent Office, "European Search Report for European Patent Application No. EP10784131," (dated Sep. 13, 2013).

International Searching Authority, "International Search Report for International Application No. PCT/US2014/027593," (dated Jul. 14, 2014), 3 pages.

English translation of Office Action dated Jul. 1, 2016 for Chinese Application No. 201480027233.9 (15 pages).

Yim et al., "Metabolic engineering of *Escherichia coli* for direct production of 1,4-butanediol", Nat Chem. Biol., 7 (7):445-452 (2011).

\* cited by examiner

US 9,873,652 B2

PROCESS AND SYSTEMS FOR OBTAINING 1,4-BUTANEDIOL FROM FERMENTATION BROTHS

This application is a U.S. National Stage filing under 35 U.S.C. §371 of International Application No. PCT/US2014/027593, filed Mar. 14, 2014, which claims priority to U.S. Provisional Application No. 61/801,107, filed Mar. 15, 2013, U.S. Provisional Application No. 61/829,625, filed May 31, 2013, and U.S. Provisional Application No. 61/928,966, filed Jan. 17, 2014, which are incorporated herein in their entireties.

BACKGROUND

Provided here are process and systems relating generally to the separation of 1,4-butanediol or a target compound from fermentation broths.

1,4-Butanediol (1,4-BDO) is an industrial polymer intermediate useful for synthesizing polyester resins, gamma-butyrolactone, tetrahydrofuran, and other compounds. Industrial syntheses of 1,4-butanediol using nonrenewable petrochemical feedstocks are known, as are process for purifying 1,4-butanediol from crude 1,4-butanediol obtained from petrochemical based syntheses (see, e.g., Okuyama, U.S. Pat. No. 5,981,810). Fermentation production of 1,4-butanediol is an alternative to traditional production using nonrenewable petrochemical feedstocks. For instance, fermentation production utilizes renewable feedstocks such as biomass or other bio-based feedstocks, and the process can be more environmentally sound than petrochemical based production. Separating 1,4-butanediol from other components within fermentation broths, however, requires different procedures than those applicable for purifying 1,4-butanediol from petrochemical based syntheses due, for example, to the different types of components present in fermentation broths.

Adkesson et al., U.S. Pat. Pub. No. 2005/0069997 describes a process for separating 1,3-propanediol from a fermentation broth. The process in Adkesson et al. includes filtration, ion exchange and distillation, wherein distillation consists of four columns and can include a hydrogenation step between columns 2 and 3. Clark et al., WO 2010/141780 describes separating 1,4-butanediol from a fermentation broth. The process includes separating a liquid fraction from a solid fraction, removing salts from the liquid fraction, and separating the product in a series of distillations, to remove water and other light components in one distillation column and to remove heavy materials with boiling points lower than the product in another distillation column.

Challenges remaining for obtaining 1,4-butanediol or target compound from fermentation broths can include, for instance, increasing yield or purity of the 1,4-butanediol or target compound obtained from fermentation broths, reducing process steps or system components and/or reducing levels of certain particular contaminants, among other things. For example, obtaining 1,4-butanediol from fermentation broths can include undesirable organic acids and other substances, either in a fermentation broth or that are formed during steps of a procedure of purifying 1,4-butanediol, which can react with 1,4-butanediol effectively lowering yields.

SUMMARY

In some aspects, embodiments disclosed herein relate to a process of purifying 1,4-butanediol (1,4-BDO). In some embodiments the process includes (a) subjecting a crude 1,4-BDO mixture to a first column distillation procedure to remove materials with a boiling point lower than 1,4-BDO from the crude 1,4-BDO mixture to produce a first 1,4-BDO-containing product stream and (b) subjecting the first 1,4-BDO-containing product stream to a second column distillation procedure to remove materials with boiling points higher than 1,4-BDO as a first high-boilers stream, to produce a purified 1,4 BDO product, wherein the purified 1,4 BDO product is collected from a side-draw of the second column distillation procedure.

In certain embodiments, the process further includes (c) subjecting the first high-boilers stream to wiped-film evaporation (WFE) to produce a first WFE distillate and subjecting the first WFE distillate to step (b).

In certain embodiments, the process further includes (d) subjecting the first 1,4-BDO-containing product stream, prior to performing step (b), to an intermediate column distillation procedure to remove materials with boiling points higher than 1,4 BDO as a second high-boilers stream.

In certain embodiments, the process further includes subjecting the second high-boilers stream to wiped-film evaporation (WFE) producing a second WFE distillate and subjecting the second WFE distillate to step (d).

In certain embodiments, the process further includes (e) treating the first 1,4-BDO-containing product stream with a hydrogenation reaction prior to performing step (b).

In certain embodiments, the process further includes (f) treating the purified 1,4 BDO product with a hydrogenation reaction.

In certain embodiments of the process, the crude 1,4-BDO mixture is at least 50% (w/w), 60% (w/w), 70% (w/w), 80% (w/w), 85% (w/w) or 90% (w/w) 1,4-BDO.

In certain embodiments of the process, the purified 1,4-BDO product is greater than 90% (w/w), 91% (w/w), 92% (w/w), 93% (w/w), 94% (w/w), 95% (w/w), 96% (w/w), 97%, (w/w) 98% (w/w), 99% (w/w), 99.1% (w/w), 99.2% (w/w), 99.3% (w/w), 99.4% (w/w), 99.5% (w/w), 99.6% (w/w), 99.7% (w/w), 99.8% (w/w) or 99.9% (w/w), 1,4-BDO.

In certain embodiments of the process, recovery of 1,4-BDO in the purified 1,4-BDO product from the crude 1,4-BDO mixture is greater than 40%, 50%, 60%, 70%, 80%, 90%, 95%, 96%, 97%, 98% or 99%.

In certain embodiments, the process further includes culturing a modified non-naturally occurring organism to produce a 1,4-BDO in a fermentation broth, subjecting the fermentation broth to a separation procedure to obtain a separated 1,4-BDO product, and subjecting the separated 1,4 BDO product to water removal and salt removal to produce the crude 1,4-BDO mixture, wherein the separation procedure consists of a first filtration and a second filtration, wherein the first filtration is microfiltration or ultrafiltration, and wherein the second filtration is nanofiltration.

In certain embodiments, the process further includes subjecting the crude 1,4-BDO mixture to a polishing ion exchange using a polishing ion exchange resin that is an anion exchange resin.

One embodiment is a system for purifying 1,4-BDO including two distillation columns. The system includes a first distillation column receiving a crude 1,4-BDO mixture and generating a first stream of materials with boiling points lower than 1,4-BDO and a 1,4-BDO-containing product stream, a second distillation column receiving the 1,4 BDO-containing product stream at a feed point and generating a first stream of materials with boiling points higher than 1,4-BDO, a second stream of materials with boiling points lower than 1,4-BDO, and a purified 1,4-BDO product from a side-draw and a wiped-film evaporator receiving the first stream of materials with boiling points higher than 1,4-BDO and generating a distillate, where the distillate is fed to the second distillation column.

In certain embodiments, the system further includes a hydrogenation reactor constructed to treat the purified 1,4-BDO product generated by the second distillation column.

One embodiment is a system for purifying 1,4-BDO including three distillation columns. The system includes a first distillation column receiving a crude 1,4-BDO mixture generating a first stream of materials with boiling points lower than 1,4-BDO and a first 1,4-BDO-containing product stream, an intermediate distillation column receiving the first 1,4 BDO-containing product stream generating a first stream of materials with boiling points higher than 1,4-BDO, and a second 1,4 BDO-containing product stream, a wiped-film evaporator receiving the first stream of materials with boiling points higher than 1,4-BDO and generating a distillate, wherein the distillate is fed to the intermediate distillation column and a second distillation column receiving the second 1,4 BDO-containing product stream at a feed point and generating a second stream of materials with boiling points lower than 1,4 BDO, a second stream of materials with boiling points higher than 1,4-BDO, and a purified 1,4-BDO product from a side-draw.

In certain embodiments, the system include three distillation columns further includes a hydrogenation reactor constructed to treat the second 1,4-BDO-containing product stream prior to the second 1,4-BDO-containing product stream being received by the second distillation column.

One embodiment is a process of producing a 1,4-BDO product. The process of producing a 1,4-BDO product includes culturing a modified non-naturally occurring organism to produce a 1,4-BDO in a fermentation broth, subjecting the fermentation broth to a separation procedure to obtain a separated 1,4 BDO product, where the separation procedure consists a first filtration and a second filtration, where the first filtration is microfiltration or ultrafiltration, and where the second filtration is nanofiltration, and subjecting the separated 1,4-BDO product to a polishing ion exchange using a polishing ion exchange resin.

In certain embodiments, the process of producing a 1,4-BDO product includes subjecting the separated 1,4-BDO product to water removal before subjecting the separated 1,4-BDO product to the polishing ion exchange.

One embodiment is a bioderived 1,4-BDO, where the bioderived 1,4-BDO is produced by any of the processes described herein.

In certain embodiments, the bioderived 1,4-BDO has a carbon-12, carbon-13 and carbon-14 isotope ratio that reflects an atmospheric carbon dioxide source.

One embodiment is a biobased plastic, elastic fiber, polyurethane, polyester, poly-4-hydroxybutyrate or co-polymer thereof, poly(tetramethylene ether) glycol and polyurethane-polyurea copolymer including the bioderived 1,4-BDO.

In certain embodiments, the biobased plastic, elastic fiber, polyurethane, polyester, poly-4-hydroxybutyrate or co-polymer thereof, poly(tetramethylene ether) glycol and polyurethane-polyurea copolymer includes at least 5%, at least 10%, at least 20%, at least 30%, at least 40%, or at least 50% bioderived 1,4-BDO.

One embodiment is a system for purifying 1,4-BDO including four distillation columns. The system includes a first distillation column receiving a crude 1,4-BDO mixture generating a first stream of materials with boiling points lower than 1,4-BDO and a first 1,4-BDO-containing product stream, a first intermediate distillation column receiving the first 1,4 BDO-containing product stream generating a first stream of materials with boiling points higher than 1,4-BDO, and a second 1,4 BDO-containing product stream, a wiped-film evaporator receiving the first stream of materials with boiling points higher than 1,4-BDO and generating a distillate, wherein the distillate is fed to the first intermediate distillation column, a second intermediate distillation column receiving the second 1,4 BDO-containing product stream generating a second stream of materials with boiling points lower than 1,4-BDO, and a third 1,4 BDO-containing product stream and a second distillation column receiving the third 1,4 BDO-containing product stream at a feed point and generating a third stream of materials with boiling points lower than 1,4 BDO, a third stream of materials with boiling points higher than 1,4-BDO, and a purified 1,4-BDO product.

In certain embodiments, the system includes four distillation columns and further includes a hydrogenation reactor constructed to treat the second 1,4-BDO-containing product stream prior to the second 1,4-BDO-containing product stream being received by the second intermediate distillation column.

In certain embodiments, the system includes four distillation columns, the second distillation column further includes a side draw, and the generated purified 1,4-BDO product is from the side draw.

One embodiment is a process of purifying 1,4-butanediol. The process includes subjecting a crude 1,4-BDO mixture to a first column distillation procedure to remove materials with a boiling point lower than 1,4-BDO from the crude 1,4-BDO mixture to produce a first 1,4-BDO-containing product stream; subjecting the first 1,4-BDO-containing product stream to a first intermediate column distillation procedure to remove materials with a boiling point higher than 1,4-BDO, as a first high boilers stream, to produce a second 1,4-BDO-containing product stream; subjecting the first high-boilers stream to wiped-film evaporation (WFE) to produce a WFE distillate and subjecting the WFE distillate to the first intermediate column distillation procedure; subjecting the second 1,4-BDO-containing product stream to a second intermediate column distillation procedure to remove materials with a boiling point lower than 1,4-BDO, to produce a third 1,4-BDO-containing product stream; and subjecting the third 1,4-BDO-containing product stream to a second column distillation procedure to remove materials with boiling points higher than 1,4-BDO as a second high-boilers stream, to produce a purified 1,4-BDO product.

In certain embodiments, the process further includes treating the second 1,4-BDO-containing product stream with a hydrogenation reaction prior to performing the second intermediate column distillation.

In certain embodiments of the process, the purified 1,4-BDO product is collected as a distillate of the second column distillation procedure.

In certain embodiments of the process, recovery of 1,4-BDO in the purified 1,4-BDO product from the crude 1,4-BDO mixture is greater than 40%, 50%, 60%, 70%, 80%, 90%, 95%, 96%, 97%, 98% or 99%.

DETAILED DESCRIPTION

Figure 1A:
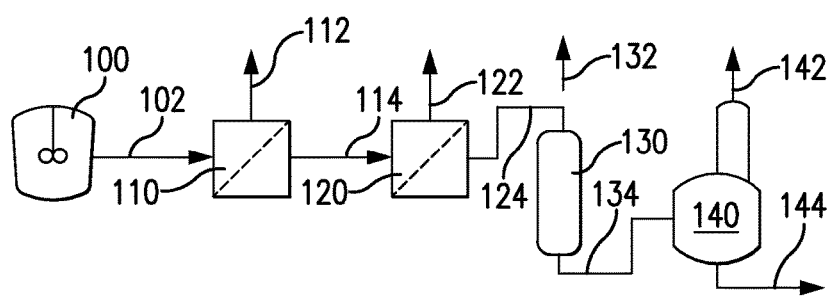
FIG. 1A depicts an exemplary system to produce a crude 1,4-BDO mixture from 1,4-BDO in a fermentation broth with two filtrations, primary ion exchange and evaporation.

In one aspect, a process for purifying a 1,4-butanediol (1,4-BDO or target compound product is provided. In certain embodiments, the process provided includes subjecting a 1,4-BDO or target compound in a fermentation broth to a separation procedure. In one embodiment, the process provided includes culturing a non-naturally occurring microbial organism to produce a 1,4-BDO or target compound in a fermentation broth and subjecting the 1,4-BDO or target compound in the fermentation broth to a separation procedure, to produce a 1,4-BDO or target compound product. In the absence of further process steps, this 1,4-BDO or target compound product can be referred to as the "separated 1,4-BDO product" or the "separated target compound product." In certain embodiments, the separated 1,4-BDO or target compound product is cell-free or is essentially cell-free.

The purification process and/or the one or more steps disclosed herein can be used to purify 1,4-BDO and other bio-synthetically produced target compound. The target compound can have a physical property similar to 1,4-BDO, including one or more properties selected from a boiling point higher than water (>100° C.) and solubility in water, or can have both properties. The solubility of the target compound can be highly soluble in water, or greater than 100 grams target compound per liter at 23° C., or greater than 500 grams target compound per liter at 23° C., or fully miscible in water at 23° C. In one embodiment, the target compound can have a boiling point higher than water and a solubility at 23° C. of greater than 500 g/L or completely miscible in water.

The target compound can include an alcohol, a diol, a triol, a monohydric, a dihydric or a trihydric alcohol; a lower monohydric, a dihydric or a trihydric alcohol; a butanediol; 1,3-butanediol, a germinal or a vicinal diol; and can include a glycol including 1,3-propanediol, ethylene glycol, diethylene glycol, triethylene glycol, 1,2-propylene glycol, dipropylene glycol, tripropylene glycol, neopentyl glycol and bisphenol A.

The processes can be applied to 1,4-BDO or other target compounds produced in a non-naturally occurring microbial organism genetically engineered to produce 1,4-BDO or other target compound. Host microbial organisms can be selected from, and the non-naturally occurring microbial organisms generated in, for example, bacteria, yeast, fungus or any of a variety of other microorganisms applicable or suitable to fermentation processes. Exemplary bacteria include any species selected from the order Enterobacteriales, family Enterobacteriaceae, including the genera *Escherichia* and *Klebsiella*; the order Aeromonadales, family Succinivibrionaceae, including the genus *Anaerobiospirillum*; the order Pasteurellales, family Pasteurellaceae, including the genera *Actinobacillus* and *Mannheimia*; the order Rhizobiales, family Bradyrhizobiaceae, including the genus *Rhizobium*; the order Bacillales, family Bacillaceae, including the genus *Bacillus*; the order Actinomycetales, families Corynebacteriaceae and Streptomycetaceae, including the genus *Corynebacterium* and the genus *Streptomyces*, respectively; order Rhodospirillales, family Acetobacteraceae, including the genus *Gluconobacter*; the order Sphingomonadales, family Sphingomonadaceae, including the genus *Zymomonas*; the order Lactobacillales, families Lactobacillaceae and Streptococcaceae, including the genus *Lactobacillus* and the genus *Lactococcus*, respectively; the order Clostridiales, family Clostridiaceae, genus *Clostridium*; and the order Pseudomonadales, family Pseudomonadaceae, including the genus *Pseudomonas*. Non-limiting species of host bacteria include *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens*, and *Pseudomonas putida*.

Similarly, exemplary species of yeast or fungi species include any species selected from the order Saccharomycetales, family Saccharomycetaceae, including the genera *Saccharomyces, Kluyveromyces* and *Pichia*; the order Saccharomycetales, family Dipodascaceae, including the genus *Yarrowia*; the order Schizosaccharomycetales, family Schizosaccaromycetaceae, including the genus *Schizosaccharomyces*; the order Eurotiales, family Trichocomaceae, including the genus *Aspergillus*; and the order Mucorales, family Mucoraceae, including the genus *Rhizopus*. Non-limiting species of host yeast or fungi include *Saccharomyces cerevisiae, Schizosaccharomyces pombe, Kluyveromyces lactis, Kluyveromyces marxianus, Aspergillus terreus, Aspergillus niger, Pichia pastoris, Rhizopus arrhizus, Rhizopus oryzae, Yarrowia lipolytica*, and the like. *E. coli* is a particularly useful host organism since it is a well characterized microbial organism suitable for genetic engineering. Other particularly useful host organisms include yeast such as *Saccharomyces cerevisiae*. It is understood that any suitable microbial host organism can be used to introduce metabolic and/or genetic modifications to produce a desired product.

As used herein, the term "crude 1,4-BDO mixture" is intended to mean a mixture of 1,4-BDO that is about 50% to 90% 1,4-BDO and 50% to 1% water with one or more other impurities that are derived from a fermentation process, preferably about 75% to 85% 1,4-BDO or more preferably about 80% to 85% 1,4-BDO with 1% to 25% water with one or more other impurities derived from a fermentation process.

As used herein, the term "1,4-BDO-containing product stream" is intended to mean material that leaves a procedure and contains the majority of 1,4-BDO that entered the procedure.

As used herein, the term "1,4-BDO product" is intended to mean a mixture that contains 1,4-BDO, and has been subjected to at least one procedure to increase the content of 1,4-BDO or decrease the content of an impurity. The term 1,4-BDO product can include a crude 1,4-BDO mixture, however, the 1,4-BDO and water content of a 1,4-BDO product can be higher or lower than a crude 1,4-BDO mixture.

As used herein, the term "1,4-BDO in a fermentation broth" is intended to mean a fermentation broth that contains 1,4-BDO produced by culturing a non-naturally occurring microbial organism capable of producing 1,4-BDO in a suitable culturing medium.

As used herein, the term "bioderived" means produced from or synthesized by a biological organism and can be considered a renewable resource since it can be generated by a biological organism. Such a biological organism, in particular the microbial organisms of the invention disclosed herein, can utilize feedstock or biomass, such as, sugars or carbohydrates obtained from an agricultural, plant, bacterial, or animal source; or other renewable sources such as synthesis gas ($CO$, $CO_2$ and/or $H_2$). Coal products can also be used as a carbon source for a biological organism to synthesize a biobased product of the invention. Alternatively, the biological organism can utilize atmospheric carbon. As used herein, the term "biobased" means a product as described above that is composed, in whole or in part, of a bioderived compound of the invention. A biobased or bioderived product is in contrast to a petroleum derived product, wherein such a product is derived from or chemically synthesized from petroleum or a petrochemical feedstock.

Culturing 1,4-BDO Producing Microorganisms

A 1,4-BDO in a fermentation broth can be obtained, for instance, by culturing a microbial organism capable of producing 1,4-BDO via a set of 1,4-BDO pathway enzymes. Exemplary microbial organisms include, without limitation, those described in U.S. Pat. No. 8,067,214, U.S. 2012/009434 (WO2008/115840); U.S. Pat. No. 7,947,485 (WO 2009/023493); U.S. Pat. No. 7,858,350 (WO 2010/030711); U.S. Pat. No. 8,129,169, U.S. 2011/0159572 (WO2010/141290); U.S. 2011/0229946 (WO 2011/047101; and U.S. 2011/0217742 (WO2011/066076), all of which are incorporated herein by reference in their entireties.

Any of the previously exemplified host organisms can be used for engineering into a 1,4-BDO biosynthetic pathway including, for example, bacteria and yeast. Exemplary species include, for example, *E. coli* and *Saccharomyces cerevisiae*. Suitable organisms for producing 1,4-BDO can be, for example, those host organisms that have been modified by incorporating into the organism one or more exogenous nucleic acids that encode one or more enzymes in a 1,4-BDO biosynthetic pathway. Such organisms include, for example, non-naturally occurring microbial organisms engineered to have a complete 1,4-BDO biosynthetic pathway. Such pathways can include enzymes encoded by both endogenous and/or exogenous nucleic acids. Enzymes not normally present in a microbial host can be introduced to complete a 1,4-BDO biosynthetic pathway by including one or more exogenous nucleic acids, for example. One exemplary 1,4-BDO pathway includes enzymes encoding a 4-hydroxybutanoate dehydrogenase, a succinyl-CoA synthetase, a CoA-dependent succinic semialdehyde dehydrogenase, a 4-hydroxybutyrate:CoA transferase, a 4-butyrate kinase, a phosphotransbutyrylase, an α-ketoglutarate decarboxylase, an aldehyde dehydrogenase, an alcohol dehydrogenase or an aldehyde/alcohol dehydrogenase. Other pathways include, without limitation, those described in U.S. Pat. No. 8,067,214, U.S. 2012/009434 (WO2008/115840); U.S. Pat. No. 7,947,485 (WO 2009/023493); U.S. Pat. No. 7,858,350 (WO 2010/030711); U.S. Pat. No. 8,129,169, U.S. 2011/0159572 (WO2010/141290); U.S. 2011/0229946 (WO 2011/047101; and U.S. 2011/0217742 (WO2011/066076), all of which are incorporated herein by reference in their entireties.

Those skilled in the art will know suitable carbon and nitrogen sources for maintaining cultures suitable for producing 1,4-BDO in a fermentation broths, as well as techniques for controlling the pH of the cultures. Exemplary procedures used in the fermentation of 1,4-BDO producing microbial organisms can be, for example, batch fermentation, fed-batch fermentation with batch separation; fed-batch fermentation with continuous separation, semi-continuous fermentation with batch separation, semi-continuous fermentation with continuous separation, continuous fermentation with batch separation, or continuous fermentation with continuous separation. All of these processes are well known in the art. Depending on the organism design, the fermentations can be carried out under aerobic, anaerobic or substantially anaerobic conditions.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

In certain embodiments of the process provided, culturing a non-naturally occurring microbial organism to produce a 1,4-BDO in a fermentation broth includes culturing a genetically modified *E. coli* or yeast such as *Saccharomyces cerevisiae*, under anaerobic or substantially anaerobic batch fermentation conditions to produce the 1,4-BDO in the fermentation broth.

Culturing a Target Compound Producing Organism

A target compound in a fermentation broth can be obtained, for instance, by culturing a microbial organism capable of producing the target compound via a set of target compound pathway enzymes. Exemplary microbial organisms engineered to express target compound pathway enzymes and produce target compounds include, without limitation, those described in patent or Patent Publication Nos. U.S. 2005/0069997-A1 (WO 2004/101479); U.S. 2010/0330635-A1 (WO 2010/127319); U.S. 2012/0329113-A1 (WO 2012/177619), and U.S. 2013/0066035-A1 (WO/2013/036764); all of which are incorporated herein by reference in their entireties.

As described previously, of the previously exemplified host organisms can be used for engineering into a 1,4-BDO biosynthetic pathway including, for example, bacteria and yeast. Exemplary species include, for example, *E. coli* and

*Saccharomyces cerevisiae*. Suitable organisms for producing a target compound can be, for example, those that have been modified by incorporating into the organism one or more exogenous nucleic acids that encode one or more enzymes in a target compound biosynthetic pathway. Such organisms include, for example, non-naturally occurring microbial organisms engineered to have a complete target compound biosynthetic pathway. Such pathways can include enzymes encoded by both endogenous and/or exogenous nucleic acids. Enzymes not normally present in a microbial host can be introduced to complete a target compound biosynthetic pathway by including one or more exogenous nucleic acids, for example. One exemplary target compound is 1,3-BDO. The 1,3-BDO can be produced from a host organism engineered to have a complete 1,3-BDO biosynthetic pathway. One exemplary 1,3-BDO pathway includes enzymes encoding a includes enzymes encoding an acetoacetyl-CoA thiolase, an acetoacetyl-CoA reductase (ketone reducing), a 3-hydroxybutyryl-CoA reductase (aldehyde forming), and a 3-hydroxybutyraldehyde reductase.

Those skilled in the art will know suitable carbon and nitrogen sources for maintaining cultures suitable for producing target compound in a fermentation broths, as well as techniques for controlling the pH of the cultures. Exemplary cell growth procedures used in the fermentation of target compound producing microbial organisms can be, for example, batch fermentation, fed-batch fermentation with batch separation; fed-batch fermentation with continuous separation, semi-continuous fermentation with batch separation, semi-continuous fermentation with continuous separation, continuous fermentation with batch separation, or continuous fermentation with continuous separation. All of these processes are well known in the art. Depending on the organism design, the fermentations can be carried out under aerobic, anaerobic or substantially anaerobic conditions.

In certain embodiments of the process provided, culturing a non-naturally occurring microbial organism to produce a target compound in a fermentation broth includes culturing a genetically modified *E. coli* or yeast such as *Saccharomyces cerevisiae*, under anaerobic or substantially anaerobic batch fermentation conditions to produce the target compound in the fermentation broth.

Biomass Deactivation

The organisms or cells that make up the cellular biomass present in the fermentation broth at the end of the fermentation can be subjected to deactivating or killing. Alternatively, if cells are recycled for use as inoculum of the next fermentation or as part of a continuous cell recycle loop, the killing is done after cell removal and before disposal. Cell recycling can be performed using known methods, for example, with a membrane cell recycle reactor. In the biomass deactivation, the cells are transferred to a heat exchanger for the killing, in manner that minimizes cell lysis yet promotes cell agglomeration or flocculation during the deactivation. Biomass deactivation or cell killing is performed at a temperature from about 50° C. to 80° C., from about 60° C. to 70° C., at least about 60° C., or at least about 70° C., for a duration of about from 1 minute to 10 minutes, 2 minutes to 5 minutes, from 2 minutes to 3 minutes, at least 2 minutes, or at least 2.5 minutes.

Separations

In certain embodiments of the process described herein, subjecting the 1,4-BDO or target compound in the fermentation broth to a separation procedure includes subjecting the 1,4-BDO or target compound in the fermentation broth to one or more of the procedures of biomass deactivation, centrifugation, microfiltration, ultrafiltration and nanofiltration.

Multiple filtration membranes can be used serially with gradually increasing refinement of the size of the solids, and/or charge of the solids, that are retained. Multiple filtrations can be useful to reduce fouling of membranes and aid in recovering individual components of the fermentation broth for recycle. The invention includes all combinations and permutations of centrifugation, microfiltration, ultrafiltration and nanofiltration as exemplified below.

Centrifugation

Centrifugation can be used to provide a 1,4-BDO or target compound product substantially free of solids, including cell mass. Depending on the centrifuge configuration and size, operating speeds can vary from less than 500 rpm, generally from 500 rpm to 12,000 rpm or more than 12,000 rpm. The rpm from 500 to 12,000 can produce a centrifugal force of up to and over 15,000 times the force of gravity. Many centrifuge configurations for removal of cells and solids from a fermentation broth are known in the art and can be employed in the process of the invention. Such configurations include, for example, a disc-stack centrifuge and a decanter, or solid bowl centrifuge. Centrifugation can occur batch-wise or in a continuous fashion. All combinations of centrifugation configurations well known in the art can be employed in the process of the invention.

The cells and solids can be separated by multiple centrifugations to increase the yield of 1,4-BDO or target compound. Multiple centrifugations can it include centrifugation two times, three times, four times, and five times or more times, for example. Intermediate underflow streams can be diluted with water and passed through additional centrifugation to further increase recovery of the liquid product. Any combination of configurations can also be used to perform multiple centrifugations, such as combinations of the disc-stack and decanter centrifugations described above.

Microfiltration

Microfiltration, for example, involves a low-pressure membrane process for separating colloidal and suspended particles in the range of about 0.05-10 microns. Useful configurations include cross-flow filtration using spiral-wound, hollow fiber, or flat sheet (cartridge) microfiltration elements. Microfiltration includes filtering through a membrane having pore sizes from about 0.05 microns to about 10.0 microns. Microfiltration membranes can have nominal molecular weight cut-offs (MWCO) of about 20,000 Daltons and higher. The term molecular weight cut-off is used to denote the size of particle, including polypeptides, or aggregates of peptides, that will be approximately 90% retained by the membrane. Polymeric, ceramic, or steel microfiltration membranes can be used to separate cells. Ceramic or steel microfiltration membranes have long operating lifetimes including up to or over 10 years. Microfiltration can be used in the clarification of fermentation broth. For example, microfiltration membranes can have pore sizes from about 0.05 microns to 10 micron, or from about 0.05 microns to 2 microns, about 0.05 microns to 1.0 micron, about 0.05 microns to 0.5 microns, about 0.05 microns to 0.2 microns, about 1.0 micron to 10 microns, or about 1.0 micron to 5.0 microns, or membranes can have a pore size of about 0.05 microns, about 0.1 microns, or about 0.2 microns For example, microfiltration membranes can have a MWCO from about 20,000 Daltons to 500,000 Daltons, about 20,000 Daltons to 200,000 Daltons, about 20,000 Daltons to 100,000 Daltons, about 20,000 Daltons to 50,000 Daltons, or with about 50,000 Daltons to 300,000 Daltons; or with a MWCO of about 20,000 Daltons, about 50,000 Dalton, about 100,000 Daltons or about 300,000 Daltons can be used in separating cell and solids from the fermentation broth.

Ultrafiltration

Ultrafiltration is a selective separation process through a membrane using pressures up to about 145 psi (10 bar). Useful configurations include cross-flow filtration using spiral-wound, hollow fiber, or flat sheet (cartridge) ultrafiltration elements. These elements consist of polymeric or ceramic membranes with a molecular weight cut-off of less than about 200,000 Daltons. Ceramic ultrafiltration membranes are also useful since they have long operating lifetimes of up to or over 10 years. Ceramics have the disadvantage of being much more expensive than polymeric membranes. Ultrafiltration concentrates suspended solids and solutes of molecular weight greater than about 1,000 Daltons. Ultrafiltration includes filtering through a membrane having nominal molecular weight cut-offs (MWCO) from about 1,000 Daltons to about 200,000 Daltons (pore sizes of about 0.005 to 0.1 microns). For example, ultrafiltration membranes can have pore sizes from about 0.005 microns to 0.1 micron, or from about 0.005 microns to 0.05 microns, about 0.005 microns to 0.02 micron, or about 0.005 microns to 0.01 microns. For example, ultrafiltration membranes can have a MWCO from about 1,000 Daltons to 200,000 Daltons, about 1,000 Daltons to 50,000 Daltons, about 1,000 Daltons to 20,000 Daltons, about 1,000 Daltons to 5,000 Daltons, or with about 5,000 Daltons to 50,000 Daltons. Using ultrafiltration the permeate liquid will contain low-molecular-weight organic solutes, such as 1,4-BDO or target compound, media salts, and water. The captured solids can include, for example, residual cell debris, DNA, and proteins. Diafiltration techniques well known in the art can be used to increase the recovery of 1,4-BDO or target compound in the ultrafiltration step.

Nanofiltration

A further filtration procedure called nanofiltration can be used to separate out certain materials by size and charge, including carbohydrates, inorganic and organic salts, residual proteins and other high molecular weight impurities that remain after the previous filtration step. This procedure can allow the recovery of certain salts without prior evaporation of water, for example. Nanofiltration can separate salts, remove color, and provide desalination. In nanofiltration, the permeate liquid generally contains monovalent ions and low-molecular-weight organic compounds as exemplified by 1,4-BDO or target compound. Nanofiltration includes filtering through a membrane having nominal molecular weight cut-offs (MWCO) from about 100 Daltons to about 2,000 Daltons (pore sizes of about 0.0005 to 0.005 microns). For example, nanofiltration membranes can have a MWCO from about 100 Daltons to 500 Daltons, about 100 Daltons to 300 Daltons, or about 150 Daltons to 250 Daltons. The mass transfer mechanism in nanofiltration is diffusion. The nanofiltration membrane allows the partial diffusion of certain ionic solutes (such as sodium and chloride), predominantly monovalent ions, as well as water. Larger ionic species, including divalent and multivalent ions, and more complex molecules are substantially retained (rejected). Larger non-ionic species, such as carbohydrates are also substantially retained (rejected). Nanofiltration is generally operated at pressures from 70 psi to 700, psi, from 200 psi to 650 psi, from 200 psi to 600 psi, from 200 psi to 450 psi, from 70 psi to 400 psi, of about 400 psi, of about 450 psi or of about 500 psi.

One embodiment of a nanofiltration has a membrane with a molecular weight cut off of about 200 Daltons that rejects, for example, about 99% of divalent salts such as magnesium sulfate. A certain embodiment would have a nanofiltration membrane with a molecular weight cut off of about 150-300 Daltons for uncharged organic molecules.

Salt Removal and Water Removal

In certain embodiments, the process for purifying a 1,4-BDO or target compound product further includes subjecting the separated 1,4-BDO or target compound product to salt removal, water removal, or both salt removal and water removal. Removing salts from the separated 1,4-BDO or target compound product can be achieved before or after removal of some or substantially all of the water from the separated 1,4-BDO or target compound product. In certain embodiments of the process provided, salt removal is achieved through subjecting a 1,4-BDO or target compound product to an ion exchange procedure. In certain embodiments of the process provided, salt removal includes crystallization. In certain embodiments of the process provided, water removal is achieved through subjecting a 1,4-BDO or target compound product to evaporation. In certain embodiments of the process provided, water removal is achieved through subjecting a 1,4-BDO or target compound product to reverse osmosis.

In certain embodiments, the 1,4-BDO or target compound product obtained after salt removal and/or water removal is a crude 1,4-BDO or target compound mixture. The crude 1,4-BDO or target compound mixture obtained is at least 50%, 60%, 70%, 80%, 85% or 90% 1,4-BDO or target compound, and is less than 50%, 40%, 30%, 20%, 15%, 10% or 5% water on a weight/weight basis.

Ion Exchange

Ion exchange can be used to remove salts from a mixture, such as for example, a fermentation broth. Ion exchange elements can take the form of resin beads as well as membranes. Frequently, the resins can be cast in the form of porous beads. The resins can be cross-linked polymers having active groups in the form of electrically charged sites. At these sites, ions of opposite charge are attracted, but can be replaced by other ions depending on their relative concentrations and affinities for the sites. Ion exchange resins can be cationic or anionic, for example. Factors that determine the efficiency of a given ion exchange resin include the favorability for a given ion, and the number of active sites available. To maximize the active sites, large surface areas can be useful. Thus, small porous particles are useful because of their large surface area per unit volume.

The anion exchange resins can be strongly basic or weakly basic anion exchange resins, and the cation exchange resin can be strongly acidic or weakly acidic cation exchange resin. Non-limiting examples of ion-exchange resin that are strongly acidic cation exchange resins include AMBERJET™ 1000 Na, AMBERLITE™ IR10 or DOWEX™ 88; weakly acidic cation exchange resins include AMBERLITE™ IRC86 or DOWEX™ MAC3; strongly basic anion exchange resins include AMBERJET™ 4200 Cl or DOWEX™ 22; and weakly basic anion exchange resins include AMBERLITE™ IRA96, DOWEX™ 66 or DOWEX™ Marathon WMA. Ion exchange resins can be obtained from a variety of manufacturers such as Dow, Purolite, Rohm and Haas, Mitsubishi or others.

A primary ion exchange can be utilized for the removal of salts. The primary ion exchange can include, for example, both a cation exchange or an anion exchange, or a mixed cation-anion exchange, which include both cation exchange and anion exchange resins. In certain embodiments, primary ion exchange can be cation exchange and anion exchange in any order. In some embodiments, the primary ion exchange is an anion exchange followed by a cation exchange, or a cation exchange followed by an anion exchange, or a mixed cation-anion exchange. In certain embodiments, the primary ion exchange is an anion exchange, or a cation exchange. More than one ion exchange of a given type, can be used in the primary ion exchange. For example, the primary ion exchange can include a cation exchange, followed by an anion exchange, followed by a cation exchange and finally followed by an anion exchange.

In certain embodiments, the primary ion exchange uses a strongly acidic cation exchange and a weakly basic anion exchange Ion exchange, for example, primary ion exchange, can be carried out at temperatures from 20° C. to 60° C., from 30° C. to 60° C., 30° C. to 50° C., 30° C. to 40° C. or 40° C. to 50° C.; or at about 30° C., about 40° C., about 50° C., or about 60° C. Flow rates in ion exchange, such as primary ion exchange, can be from 1 bed volume per hour (BV/h) to 10 BV/h, 2 BV/h to 8 BV/h, 2 BV/h to 6 BV/h, 2 BV/h to 4 BV/h, 4 BV/h to 6 BV/h, 4 BV/h to 8 BV/h, 4 BV/h to 10 BV/h or 6 BV/h to 10 BV/h.

Crystallization

An evaporative crystallizer can be used to generate precipitated salts which can be removed by centrifugation, filtration or other mechanical means. In the process of purifying 1,4-BDO or target compound, an evaporative crystallizer can serve for the removal of water from the fermentation broth and simultaneously cause supersaturation of the salts in the fermentation broth, and subsequent crystallization of the salts, which can then be removed. In some embodiments, the salts have a sufficiently low solubility in 1,4-BDO or target compound that the separated 1,4-BDO or target compound is about 98% salt-free. Examples of evaporative crystallizers can be a forced circulation crystallizer, a turbulence or draft-tube and baffle crystallizer, an induced circulation crystallizer, or an Oslo-type (also known as "growth-", "fluid-bed-" or "Krystal-" type) crystallizer.

Many of the evaporative crystallization apparatus allow for controlled crystal growth. In the removal of crystallization salts from a 1,4-BDO or target compound product, the exact crystal morphology, size, and the like are generally inconsequential. Hence, removal of amorphous salts can be sufficient in the crystallization procedure. Thus, in some embodiments, other evaporation methods can be utilized that do not control crystal growth per se.

Reverse Osmosis

When salts are removed by nanofiltration and/or ion exchange, a reverse osmosis (RO) membrane filtration can be used to remove a portion of the water prior to evaporation. Water permeates the RO membrane while 1,4-BDO or target compound is retained. In some embodiments, an RO membrane can concentrate a product, such as 1,4-BDO or target compound to about 20%. One skilled in the art will recognize that the osmotic pressure from the 1,4-BDO or target compound increases to a point where further concentration using an RO membrane can no longer be viable. Nonetheless, the use of an RO membrane is a useful low energy input method for concentrating 1,4-BDO or target compound prior to the more energy intensive water evaporation process. Thus, on large scale, employing a RO membrane can be particularly useful.

Evaporation

There are many types and configurations of evaporators well known to those skilled in the art that are available for water removal. An evaporator is a heat exchanger in which a liquid is boiled to give a vapor that is also a low pressure steam generator. This steam can be used for further heating in another evaporator called another "effect." Removing water is accomplished by evaporation with an evaporator system which includes one or more effects. In some embodiments, a double- or triple-effect evaporator system can be used to separate water from 1,4-BDO or target compound. Any number of multiple-effect evaporator systems can be used in the removal of water. A triple effect evaporator, or other evaporative apparatus configuration, can include dedicated effects that are evaporative crystallizers for salt recovery, for example the final effect of a triple effect configuration. Alternatively, mechanical vapor recompression or thermal vapor recompression evaporators can be utilized to reduce the energy required for evaporating water beyond what can be achieved in standard multiple effect evaporators.

Examples of evaporators include a falling film evaporator (which can be a short path evaporator), a forced circulation evaporator, a plate evaporator, a circulation evaporator, a fluidized bed evaporator, a rising film evaporator, a counterflow-trickle evaporator, a stirrer evaporator and a spiral tube evaporator.

Polishing

Polishing is a procedure to remove any remaining salts and/or other impurities in a crude 1,4-BDO or target compound mixture. The polishing can include contacting the crude 1,4-BDO or target compound mixture with a number of materials that can react with or adsorb the impurities in the crude 1,4-BDO or target compound mixture. The materials used in the polishing can include ion exchange resins, activated carbon, or adsorbent resins, such as, for example, DOWEX™ 22, DOWEX™ 88, OPTIPORE™ L493, AMBERLITE™ XAD761 or AMBERLITE™ FPX66, or mixtures of these resins, such as a mixture of DOWEX™ 22 and DOWEX™ 88.

Polishing Ion Exchange

In one embodiment, the polishing is a polishing ion exchange. The polishing ion exchange can be used to remove any residual salts, color bodies and color precursors before further purification. The polishing ion exchange can include an anion exchange, a cation exchange, both a cation exchange and anion exchange, or can be a mixed cation-anion exchange, which includes both cation exchange and anion exchange resins. In certain embodiments, the polishing ion exchange is an anion exchange followed by a cation exchange, a cation exchange followed by an anion exchange, or a mixed cation-anion exchange. In certain embodiment, the polishing ion exchange is an anion exchange. The polishing ion exchange includes both strong cation and strong anion exchange, or includes strong anion exchange without other polishing cation exchange or polishing anion exchange. The polishing ion exchange occurs after a water removal step such as evaporation, and prior to a subsequent distillation.

Distillation

The process of purifying 1,4-BDO or target compound can include distillation of a crude 1,4-BDO or target compound mixture. The distillation can be carried out with a distillation system to produce a purified 1,4-BDO or target compound product. The purified 1,4-BDO or target compound product can be greater than 90%, 92%, 94%, 96%, 97%, 98%, 99%, 99.5%, 99.7% or 99.9% 1,4-BDO or target compound on a weight/weight basis. The distillation system can be composed of one or more distillation columns that can be used to remove materials that have a higher or lower boiling point than 1,4-BDO or target compound by generating streams of materials with boiling points higher or lower than 1,4-BDO or target compound. The distillation columns can contain, for example, random-packing, structured-packing, plates, random- and structured-packing, random-packing and plates, or structured-packing and plates. As is known in the art, many types and configurations of distillation columns are available. The recovery of 1,4-BDO or target compound in the purified 1,4-BDO or target compound product can be calculated as a percentage of the amount of 1,4-BDO or target compound in the purified 1,4-BDO or target compound product divided by the amount of 1,4-BDO or target compound in the crude 1,4-BDO or target compound mixture that was purified.

A consideration in distillation is to minimize the amount of heating that a 1,4-BDO or target compound product must undergo through the distillation process. Impurities or even the 1,4-BDO or target compound can undergo thermal or chemical decomposition while being heated during distillation. Operating the distillation columns under reduced pressure (less than atmospheric pressure) or vacuum lowers the boiling temperature of the mixture in the distillation column and allows for operating the distillation column at lower temperatures. Any of the columns described in the various embodiments of the invention can be operated under reduced pressure. A common vacuum system can be used with all distillation columns to achieve a reduced pressure, or each column can have its own vacuum system. All combinations and permutations of the above exemplary vacuum configurations are included within the invention as described herein. The pressure of a distillation column can be measured at the top or condenser, the bottom or base, or anywhere in between. The pressure at the top of a distillation column can be different than the pressure in the base of the distillation column, and this pressure difference denotes the pressure drop across the distillation column. Different distillation columns of the same embodiment can be operated at different pressures. Pressures in a column can be ambient, less than ambient, or less than 500 mmHg, 200 mmHg, 100 mmHg, 50 mmHg, 40 mmHg, 30 mmHg, 20 mmHg, 15 mmHg, 10 mmHg, or 5 mmHg, for example.

It should be understood, that a step of removing higher or lowing boiling materials with a distillation column by distillation is not expected to be 100% effective, and that residual amounts of higher or lower boiling materials can still be present in the product stream after a distillation procedure. When it is described that a material is removed by a distillation procedure, it is to be understood that the removal can mean greater that 50%, 60%, 70%, 80%, 90%, 95%, 96%, 97%, 98%, 99%, 99.5% or 99.9% of the material removed from the feed to a distillation column.

The mixture to be purified can be fed to a distillation column and, depending on the operating conditions, the higher boiling or lower boiling materials can be removed from the mixture. For example, if lower boiling materials are removed, the lower boiling materials are boiled up and removed from the top of the distillation column, and the product-containing stream with the lower boiling materials removed exits from the bottom of the distillation column. This bottom stream can be fed to a next distillation column where the high boiling materials are removed from the product-containing stream. In the next distillation column, the product-containing stream boils up and exits the distillation column from the top, and the higher boiling materials are removed from the bottom of the distillation column, thus providing a more pure product-containing stream. In another example, both the higher boiling and lower boiling materials can be removed from the product-containing stream, where in that case the lower boiling materials are boiled up and removed through the top of the column, the higher boiling materials are removed from the bottom of the column, and a product exits through a side-draw, which allows material to leave the column at an intermediate position between the top and bottom of the distillation column.

One embodiment of a distillation of a crude 1,4-BDO or target compound mixture includes (a) subjecting the crude 1,4-BDO or target compound mixture to a first distillation column procedure to remove materials with boiling points lower than 1,4-BDO or target compound from the crude 1,4-BDO or target compound mixture to produce a first 1,4-BDO or target compound product stream, and (b) subjecting the first 1,4-BDO or target compound-containing product stream to a second column distillation procedure to remove materials with boiling points lower than 1,4-BDO or target compound and to remove materials with boiling points higher than 1,4-BDO or target compound as a first high-boilers stream, to produce a purified 1,4-BDO or target compound product, where the purified 1,4-BDO or target compound product is collected from a side-draw of the of the second column distillation procedure.

In certain embodiments, materials with boiling points lower than 1,4-BDO from a first distillation column procedure are a majority water. In certain embodiments, materials with boiling points lower than 1,4-BDO from a first distillation column procedure are greater than 70%, 80%, 90%, 91%, 92%, 93%, 94%, 95%, 96%, 97%, 98% or 99% water by weight.

One embodiment of a distillation includes (a) subjecting a crude 1,4-BDO or target compound mixture to a first distillation column procedure to remove materials with boiling points higher than 1,4-BDO or target compound as a first high-boilers stream, from the crude 1,4-BDO or target compound mixture to produce a first 1,4-BDO or target compound-containing product stream, and (b) subjecting the first 1,4-BDO or target compound-containing product stream to a second column distillation procedure to remove materials with boiling points higher than 1,4-BDO or target compound as a second high boilers stream and to remove materials with boiling points lower than 1,4-BDO or target compound, to produce a purified 1,4-BDO or target compound product, where the purified 1,4-BDO or target compound product is collected from a side-draw of the second column distillation procedure.

In certain embodiments, the distillation includes subjecting the crude 1,4-BDO or target compound mixture to 3 distillation column procedures, for instance, including an intermediate distillation between the first distillation column procedure and second distillation column procedure.

For example, in certain embodiments in which distillation includes (a) subjecting a crude 1,4-BDO or target compound mixture to a first distillation column procedure to produce a first 1,4-BDO or target compound product stream, and (b) subjecting the first 1,4-BDO or target compound product stream to a second column distillation procedure, where purified 1,4-BDO or target compound product is collected from a side-draw of the second distillation procedure, distillation may further include (d) subjecting the first 1,4-BDO or target compound product stream produced from the first distillation column procedure to an intermediate column distillation procedure to remove materials with boiling points higher than 1,4-BDO or target compound as a second high-boilers stream, prior to step (b).

In certain embodiments, the distillation described herein, further includes (d) subjecting the first 1,4-BDO or target compound product stream to an intermediate column distillation procedure to remove materials with boiling points lower than 1,4-BDO or target compound, prior to subjecting the first 1,4-BDO or target compound product stream to the second column distillation procedure in step (b).

One embodiment of a distillation includes (a) subjecting a crude 1,4-BDO or target compound mixture to a first distillation column procedure to remove materials with boiling points lower than 1,4-BDO or target compound from the crude 1,4-BDO or target compound mixture to produce a first 1,4-BDO or target compound-containing product stream; (d) subjecting the first 1,4-BDO or target compound-containing product stream to an intermediate column distillation procedure to remove materials with boiling points higher than 1,4-BDO or target compound as a first high-boilers stream, to obtain a second 1,4-BDO or target compound-containing product stream; and (b) subjecting the second 1,4-BDO or target compound-containing product stream to a second column distillation procedure to remove materials with boiling points lower than 1,4-BDO or target compound and to remove materials with boiling points higher than 1,4-BDO or target compound as a second high-boilers stream, to produce a purified 1,4-BDO or target compound product, where the purified 1,4-BDO or target compound product is collected from a side-draw of the second column distillation procedure. In some embodiments, the second high boilers stream is subjected to the intermediate column distillation procedure and/or second column distillation procedure, the product of which can, for example, be included in the purified 1,4-BDO or target compound product. In some embodiments, the second high boilers stream is subjected to the intermediate column distillation procedure.

One embodiment of a distillation includes (a) subjecting a crude 1,4-BDO or target compound mixture to a first distillation column procedure to remove materials with boiling points higher than 1,4-BDO or target compound from the crude 1,4-BDO or target compound mixture as a first high-boilers stream, to produce a first 1,4-BDO or target compound-containing product stream, (d) subjecting the first 1,4-BDO or target compound-containing product stream to an intermediate column distillation procedure to remove materials with boiling points lower than 1,4-BDO or target compound to obtain a second 1,4-BDO or target compound-containing product stream and (b) subjecting the second 1,4-BDO or target compound-containing product stream to a second column distillation procedure to remove materials with boiling points lower than 1,4-BDO or target compound and to remove materials with boiling points higher than 1,4-BDO or target compound as a second high-boilers stream, to produce a purified 1,4-BDO or target compound product, where the purified 1,4-BDO or target compound product is collected from a side-draw of the second column distillation procedure. In some embodiments, the second high boilers stream is fed back into the distillation, for example, being mixed with the crude 1,4-BDO or target compound mixture and subjected to steps (a), (d) and (b). In certain embodiments, the second high boilers stream is subjected to the first column distillation procedure.

One embodiment of a distillation includes (a) subjecting a crude 1,4-BDO or target compound mixture to a first distillation column procedure to remove materials with boiling points lower than 1,4-BDO or target compound from the crude 1,4-BDO or target compound mixture to produce a first 1,4-BDO or target compound-containing product stream; (d) subjecting the first 1,4-BDO or target compound-containing product stream to a first intermediate column distillation procedure to remove materials with boiling points higher than 1,4-BDO or target compound as a first high-boilers stream, to obtain a second 1,4-BDO or target compound-containing product stream; (f) subjecting the second 1,4-BDO or target compound-containing product stream to a second intermediate distillation column procedure to remove materials with boiling points lower than 1,4-BDO or target compound, to produce a third 1,4-BDO or target compound-containing product stream and (b) subjecting the third 1,4-BDO or target compound-containing product stream to a second column distillation procedure to remove materials with boiling points higher than 1,4-BDO or target compound as a second high boilers stream, to produce a purified 1,4-BDO or target compound product. In some embodiments, the purified 1,4-BDO or target compound product is collected as a distillate of the second column distillation procedure. In some embodiments, the purified 1,4-BDO or target compound product is collected from a side-draw of the second column distillation procedure. In some embodiments, the second high boilers stream is subjected to the first intermediate column distillation procedure and/or second intermediate column distillation procedure, the product of which can, for example, be included in the purified 1,4-BDO or target compound product. In some embodiments, the second high boilers stream is subjected to the first intermediate column distillation procedure.

In certain embodiments, the purified 1,4-BDO or target compound product is greater than 90%, 91%, 92%, 93%, 94%, 95%, 96%, 97%, 98%, 99%, 99.5%, 99.6%, 99.7%, 99.8% or 99.9% 1,4-BDO or target compound on a weight/weight basis. In certain embodiments, the purified 1,4-BDO product is greater than 99% 1,4-BDO, 500 ppm to 1000 ppm 1,4-BDO monoacetate, 500 ppm to 1000 ppm 2-(4'-hydroxybutoxy)tetrahydrofuran and less than 10 ppm 2-pyrrolidone. In certain embodiments, the purified 1,4-BDO product is greater than 99% 1,4-BDO, 10 ppm to 100 ppm 1,4-BDO monoacetate, 100 ppm to 500 ppm 2-(4'-hydroxybutoxy)tetrahydrofuran and less than 5 ppm 2-pyrrolidone. In certain embodiments, the purified 1,4-BDO product is greater than 99% 1,4-BDO, 25 ppm to 75 ppm 1,4-BDO monoacetate, 200 ppm to 400 ppm 2-(4'-hydroxybutoxy)tetrahydrofuran and less than 5 ppm 2-pyrrolidone.

In the systems and processes provided herein that include distillation columns, the distillation columns have a number of stages. In some embodiments, the systems or processes of this disclosure have a distillation column with 3 to 80 stages. For example, the distillation column can have 3 to 25 stages, 25 to 50 stages or 50 to 80 stages. In some embodiments, the distillation column has 8 to 28 stages, e.g., 18 to 14 stages. In some embodiments, the distillation column has 4 stages, 8 stages, 10 stages, 11 stages, 17 stages, 22 stages, 18 stages, 23 stages, 30 stages or 67 stages.

In some embodiments, the first column in a two-column system has 50 to 80 stages. In some embodiments, the first column in a two-column system has 67 stages.

In some embodiments, the second column in a two-column system has 50 to 80 stages. In some embodiments, the second column in a two-column system has 67 stages.

In some embodiments of a two-column system, the first column has 67 stages and the second column has 67 stages.

In some embodiments, the first column in a three-column system has 5 to 15 stages. In some embodiments, the first column in a three-column system has 10 stages.

In some embodiments, the first intermediate column in a three-column system has 10 to 40 stages. In some embodiments, the first intermediate column in a three-column system has 18-28 stages. In some embodiments, the first intermediate column in a three-column system has 18 stages.

In some embodiments, the second column in a three-column system has 10 to 40 stages. In some embodiments, the second column in a three-column system has 18-28 stages. In some embodiments, the second column in a three-column system has 18 stages.

In some embodiments of a three-column system, the first column has 10 stages and the first intermediate column has 18 stages.

In some embodiments, the first column in a four-column system has 5 to 15 stages. In some embodiments, the first column in a four-column system has 10 stages.

In some embodiments, the first intermediate column in a four-column system has 10 to 40 stages. In some embodiments, the first intermediate column in a four-column system has 15 to 35 stages. In some embodiments, the first intermediate column in a four-column system has 18 stages. In some embodiments, the first intermediate column in a four-column system has 30 stages.

In some embodiments, the second intermediate column in a four-column system has 10 to 40 stages. In some embodiments, the second intermediate column in a four-column system has 15 to 35 stages. In some embodiments, the second intermediate column in a four-column system has 18 stages. In some embodiments, the second intermediate column in a four-column system has 30 stages.

In some embodiments the second column in a four-column system has 5 to 35 stages. In some embodiments, the second column in a four-column system has 10 to 30 stages. In some embodiments, the second column in a four-column system has 15 to 25 stages. In some embodiments, the second column in a four-column system has 18 stages. In some embodiments, the second column in a four column system has 23 stages.

In some embodiments of a four-column system, the first column has 10 stages, the first intermediate column has 30 stages, the second intermediate column has 30 stages and the second column has 23 stages.

In some embodiments of a four-column system, the first column has 8 stages, the first intermediate column has 18 stages, the second intermediate column has 18 stages and the second column has 18 stages.

Wiped-Film Evaporation

A wiped-film evaporation, also known as thin film evaporation, can be useful for relatively quickly separating volatile from less volatile components where components include those that are heat sensitive, viscous and tend to foul heated surfaces (e.g., amino acids, sugars and other components often found in fermentation broths). Typically in embodiments of the systems and processes described herein, the vaporizable component (distillate) from a wiped-film evaporator ("WFE") contains 1,4-BDO. Thus, as utilized in the systems and processes described herein, the WFE is a distillation component that increases product yields by recovery of 1,4-BDO or target compound from the heavies material that would otherwise be disposed. For example, in a column distillation system or process where a crude 1,4-BDO mixture (or a 1,4-BDO product stream from a first distillation column) is fed into a given distillation column from which 1,4-BDO is removed as a distillate ("low-boilers") and the bottoms purge ("high-boilers") from the distillation column (which would otherwise be disposed of) is subjected to wiped-film evaporation; the WFE's 1,4-BDO-containing distillate is put back into the column distillation system or process to increase the recovery of 1,4-BDO. Heat times in a wiped-film evaporator can be short to minimize decomposition.

In certain embodiments, the WFE is a short path distillator (SPD).

In some embodiments, the WFE is a vertical WFE.

In yet other embodiments, the WFE is a horizontal WFE.

Wiped-film evaporators can be operated under vacuum conditions, such as less than 50 mmHg, 25 mmHg, 10 mmHg, 1 mmHg, 0.1 mmHg, 0.01 mmHg or even lower.

Operating conditions for wiped-film evaporation can, for example, be with a pressure ranging from about 0.1 mmHg to 25 mmHg, about 1 mmHg to 10 mmHg, about 2 mmHg to 7.5 mmHg, about 4 mmHg to 7.5 mmHg, or about 4 mmHg to 15 mmHg, and a temperature range from about 100° C. to 150° C., 110° C. to 150° C., 115° C. to 150° C., 115° C. to 140° C., 115° C. to 130° C. or 125° C. to 150° C.

In some embodiments, the WFE can be operated at a temperature below 160° C. In some embodiments the WFE can be operated at a temperature between 145° C. and 155° C. In some embodiments, the WFE can be operated under vacuum. In some embodiments, operating conditions for wiped-film evaporators include a temperature from about 145° C. to 155° C. and a vacuum from about 4 mmHg to 15 mmHg.

In some embodiments of the two, three, or four-column distillation systems provided herein, a WFE is a component that is fed the high-boilers stream (i.e., bottoms purge, "heavies") from the second column in a two-column system or the first intermediate column in a three or four-column system. In some embodiments, the WFE distillate is recycled back into a two-column, three-column or four-column distillation system. In certain embodiments, the WFE distillate is recycled by adding it to the feed stream to the second column in a two-column system. In certain embodiments, the WFE distillate is added to the sump of the second column in a two-column system. In certain embodiments, the WFE distillate is added to the feed stream to the first intermediate column in a three or four-column system. In certain embodiments, the WFE distillate is added to the sump of the first intermediate column in a three- or four-column system. In certain embodiments, the WFE distillate is added to the feed stream to the hydrogenation unit in a three- or four-column distillation system.

In certain embodiments, the distillation includes (c) subjecting a first high-boilers stream from the distillation to wiped-film evaporation (WFE) to produce a WFE distillate. The WFE distillate can be further subjected to an intermediate column distillation procedure. In other embodiments, the WFE distillate can be further subjected step (d).

In certain embodiments, the distillation includes subjecting a first high-boilers stream from a distillation to wiped-film evaporation (WFE) to produce a WFE distillate, and subjecting the WFE distillate to a second column distillation procedure. In other embodiments, the WFE distillate can be further subjected step (b).

One embodiment of a distillation of a crude 1,4-BDO or target compound mixture includes (a) subjecting the crude 1,4-BDO or target compound mixture to a first distillation column procedure to remove materials with boiling points lower than 1,4-BDO or target compound from the crude 1,4-BDO or target compound mixture to produce a first 1,4-BDO or target compound product stream, and (b) subjecting the first 1,4-BDO or target compound-containing product stream to a second column distillation procedure to remove materials with boiling points lower than 1,4-BDO or target compound and to remove materials with boiling points higher than 1,4-BDO or target compound as a first high-boilers stream, to produce a purified 1,4-BDO or target compound product, where the purified 1,4-BDO or target compound product is collected from a side-draw of the of the second column distillation procedure, and (c) subjecting the first high-boilers stream to wiped-film evaporation (WFE) to produce a WFE distillate, and the WFE distillate is subjected to the first column distillation procedure.

In certain embodiments, the purified 1,4-BDO product from a distillation including a first distillation column procedure and a second column distillation is greater than 99% 1,4-BDO, 500 ppm to 1000 ppm 1,4-BDO monoacetate, 500 ppm to 1000 ppm 2-(4'-hydroxybutoxy)tetrahydrofuran and less than 10 ppm 2-pyrrolidone.

In certain embodiments, materials with boiling points lower than 1,4-BDO from a first distillation column procedure are a majority water. In certain embodiments, materials with boiling points lower than 1,4-BDO from a first distillation column procedure are greater than 70%, 80%, 90%, 91%, 92%, 93%, 94%, 95%, 96%, 97%, 98% or 99% water by weight.

In certain embodiments, materials with boiling points lower than 1,4-BDO from a first distillation column procedure are a majority water. In certain embodiments, materials with boiling points lower than 1,4-BDO from a first distillation column procedure are greater than 70%, 80%, 90%, 91%, 92%, 93%, 94%, 95%, 96%, 97%, 98% or 99% water by weight.

In certain embodiments, the purified 1,4-BDO product from a distillation including step (a), step (b) and step (c) is greater than 99% 1,4-BDO, 500 ppm to 1000 ppm 1,4-BDO monoacetate, 500 ppm to 1000 ppm 2-(4'-hydroxybutoxy)tetrahydrofuran and less than 10 ppm 2-pyrrolidone.

One embodiment of a distillation includes (a) subjecting a crude 1,4-BDO or target compound mixture to a first distillation column procedure to remove materials with boiling points lower than 1,4-BDO or target compound from the crude 1,4-BDO or target compound mixture to produce a first 1,4-BDO or target compound-containing product stream; (d) subjecting the first 1,4-BDO or target compound-containing product stream to an intermediate column distillation procedure to remove materials with boiling points higher than 1,4-BDO or target compound as a first high-boilers stream, to obtain a second 1,4-BDO or target compound-containing product stream; (c) subjecting the first high-boilers stream to wiped-film evaporation (WFE) to produce a WFE distillate, and the WFE distillate is subjected to the intermediate column distillation procedure and (b) subjecting the second 1,4-BDO or target compound-containing product stream to a second column distillation procedure to remove materials with boiling points lower than 1,4-BDO or target compound and to remove materials with boiling points higher than 1,4-BDO or target compound as a second high-boilers stream, to produce a purified 1,4-BDO or target compound product, where the purified 1,4-BDO or target compound product is collected from a side-draw of the second column distillation procedure.

In some embodiments, the second high boilers stream is subjected to the intermediate column distillation procedure and/or second column distillation procedure, the product of which can, for example, be included in the purified 1,4-BDO or target compound product. In some embodiments, the second high boilers stream is subjected to the intermediate column distillation procedure.

One embodiment of a distillation includes (a) subjecting a crude 1,4-BDO or target compound mixture to a first distillation column procedure to remove materials with boiling points lower than 1,4-BDO or target compound from the crude 1,4-BDO or target compound mixture to produce a first 1,4-BDO or target compound-containing product stream; (d) subjecting the first 1,4-BDO or target compound-containing product stream to a first intermediate column distillation procedure to remove materials with boiling points higher than 1,4-BDO or target compound as a first high-boilers stream, to obtain a second 1,4-BDO or target compound-containing product stream; (c) subjecting the first high-boilers stream to wiped-film evaporation (WFE) to produce a WFE distillate, and the WFE distillate is subjected to the first intermediate column distillation procedure; (f) subjecting the second 1,4-BDO or target compound-containing product stream to a second intermediate distillation column procedure to remove materials with boiling points lower than 1,4-BDO or target compound, to produce a third 1,4-BDO or target compound-containing product stream and (b) subjecting the third 1,4-BDO or target compound-containing product stream to a second column distillation procedure to remove materials with boiling points higher than 1,4-BDO or target compound as a second high boilers stream, to produce a purified 1,4-BDO or target compound product.

In some embodiments, the purified 1,4-BDO or target compound product is collected as a distillate of the second column distillation procedure. In some embodiments, the purified 1,4-BDO or target compound product is collected from a side-draw of the second column distillation procedure.

In some embodiments, the second high boilers stream is subjected to the first intermediate column distillation procedure and/or second intermediate column distillation procedure, the product of which can, for example, be included in the purified 1,4-BDO or target compound product. In some embodiments, the second high boilers stream is subjected to the first intermediate column distillation procedure.

One embodiment of the distillation system includes a first distillation column receiving a crude 1,4-BDO or target compound mixture generating a first stream of materials with boiling points lower than 1,4-BDO or target compound and a first 1,4-BDO or target compound-containing product stream, an intermediate distillation column receiving the first 1,4-BDO or target compound-containing product stream generating a first stream of materials with a boiling points higher than 1,4-BDO or target compound, and a second 1,4-BDO or target compound-containing product stream, and a wiped-film evaporator receiving the first stream of materials with a boiling points higher than 1,4-BDO or target compound and generating a distillate, and the distillate feeding the intermediate distillation column. The system also includes a second distillation column receiving the second 1,4-BDO or target compound-containing product stream at a feed point and generating a second stream of materials with boiling points lower than 1,4-BDO or target compound, a second stream of materials with a boiling points higher than 1,4-BDO or target compound, and a purified 1,4-BDO or target compound product from a side-draw.

In certain embodiments, a first stream of materials with boiling points lower than 1,4-BDO generated by a first distillation column is a majority water. In certain embodiments, a first stream of materials with boiling points lower than 1,4-BDO generated by a first distillation column is greater than 70%, 80%, 90%, 91%, 92%, 93%, 94%, 95%, 96%, 97%, 98% or 99% water by weight.

One embodiment of the distillation system includes a first distillation column receiving a crude 1,4-BDO or target compound mixture generating a first stream of materials with boiling points lower than 1,4-BDO or target compound and a 1,4-BDO or target compound-containing product stream, a second distillation column receiving the 1,4 BDO-containing product stream at a feed point and generating a second stream of materials with boiling points lower than 1,4-BDO or target compound, a first stream of materials with a boiling points higher than 1,4-BDO or target compound, and a purified 1,4-BDO or target compound product from a side-draw and a wiped-film evaporator receiving the first stream of materials with a boiling points higher than 1,4-BDO or target compound and generating a distillate, and the distillate feeding the second distillation column.

One embodiment of the distillation system includes a first distillation column receiving a crude 1,4-BDO or target compound mixture generating a first stream of materials with boiling points higher than 1,4-BDO or target compound and a first 1,4-BDO or target compound-containing product stream, a wiped-film evaporator receiving the first stream of materials with a boiling points higher than 1,4-BDO or target compound and generating a distillate, and the distillate feeding the first distillation column, and an intermediate distillation column receiving the first 1,4 BDO-containing product stream generating a first stream of materials with a boiling points lower than 1,4-BDO or target compound, and a second 1,4 BDO-containing product stream. The system also includes a second distillation column receiving the second 1,4 BDO-containing product stream at a feed point and generating a second stream of materials with boiling points lower than 1,4-BDO or target compound, a second stream of materials with a boiling points higher than 1,4-BDO or target compound, and a purified 1,4-BDO or target compound product generated from a side-draw.

One embodiment of the distillation system includes a first distillation column receiving a crude 1,4-BDO or target compound mixture generating a first stream of materials with boiling points lower than 1,4-BDO or target compound and a first 1,4-BDO or target compound-containing product stream, a first intermediate distillation column receiving the first 1,4-BDO or target compound-containing product stream generating a first stream of materials with a boiling points higher than 1,4-BDO or target compound, and a second 1,4-BDO or target compound-containing product stream, and a wiped-film evaporator receiving the first stream of materials with a boiling points higher than 1,4-BDO or target compound and generating a distillate, and the distillate feeding the first intermediate distillation column. The system also includes a second intermediate distillation column receiving the second 1,4-BDO or target compound-containing product stream and generating a second stream of materials with boiling points lower than 1,4-BDO or target compound and a third 1,4-BDO or target compound-containing product stream; and a second distillation column receiving the third 1,4-BDO or target compound-containing product stream at a feed point and generating, a second stream of materials with a boiling points higher than 1,4-BDO or target compound, and a purified 1,4-BDO or target compound product. In certain embodiments, the purified 1,4-BDO or target compound product is generated from the top of the second distillate column. In certain embodiments, the purified 1,4-BDO or target compound product is generated from a side-draw.

Hydrogenation

A hydrogenation unit can be used to react hydrogen with a material using a catalyst under pressure and heat. Hydrogenation units can be operated, for example, in batch mode or continuously. Some types of catalysts used can be metals on a support. Non-limiting examples of metals useful for hydrogenation include palladium, platinum, nickel, and ruthenium. Non-limiting examples of supports for the metal catalysts include carbon, alumina, and silica. The catalyst can also be, for example, a sponge metal type, such a RANEY-Nickel. Other nickel catalysts are available from commercial vendors, for example, NISAT 310™, E-3276 (BASF, Ludwigshafen, Germany), RANEY® 2486, or E-474 TR (Mallinckrodt Co., Calsicat Division, PA, USA). Pressures can include at least 50 psig, 100 psig, 200 psig, 300 psig, 400 psig, 500 psig, 600 psig or 1000 psig of hydrogen pressure, or from about 100 psig to 1000 psig, from about 200 psig to 600 psig, or from about 400 psig to 600 psig, of hydrogen pressure. Temperatures can be from ambient to 200° C., from about 50° C. to 200° C., from about 80° C. to 150° C., from about 90° C. to 120° C., from about 100° C. to 130° C., or from about 125° C. to 130° C. Unless otherwise described herein hydrogenation occurs after a distillation procedure that includes a substantially removing material with boiling points higher than 1,4-BDO or target compound (heavies), e.g. unfermented sugars, nitrogen-containing compounds, otherwise the heavies can foul the hydrogenation catalyst.

In certain embodiments, the distillation includes (e) treating a 1,4-BDO or target compound-containing product stream with a hydrogenation reaction prior to a second column distillation procedure. In other embodiments, the distillation includes (e) treating a 1,4-BDO or target compound-containing product stream with a hydrogenation reaction prior to performing step (b). In other embodiments, the (e) treating of the 1,4-BDO or target compound-containing product stream with a hydrogenation reaction occurs after an intermediate column distillation procedure. In other embodiments, the distillation includes (e) treating the first 1,4-BDO or target compound-containing product stream with a hydrogenation reaction prior to performing a second column distillation procedure. In other embodiments, the distillation includes (e) treating the second 1,4-BDO or target compound-containing product stream with a hydrogenation reaction prior to performing a second column distillation procedure. In other embodiments, the distillation includes (e) treating the first 1,4-BDO or target compound-containing product stream with a hydrogenation reaction prior to performing step (d). In other embodiments, the distillation includes (e) treating the second 1,4-BDO or target compound-containing product stream with a hydrogenation reaction prior to performing step (b).

In certain embodiments, the distillation includes treating a 1,4-BDO or target compound product stream with a hydrogenation reaction prior to a first intermediate column distillation procedure. In certain embodiments, the distillation includes treating a 1,4-BDO or target compound product stream with a hydrogenation reaction after a first column distillation procedure.

In further embodiments, the process for purifying 1,4-BDO or target compound includes treating the purified 1,4-BDO or target compound product with a hydrogenation reaction.

One embodiment of a distillation includes (a) subjecting a crude 1,4-BDO or target compound mixture to a first distillation column procedure to remove materials with boiling points lower than 1,4-BDO or target compound from the crude 1,4-BDO or target compound mixture to produce a first 1,4-BDO or target compound-containing product stream; (b) subjecting the first 1,4-BDO or target compound-containing product stream to a first intermediate column distillation procedure to remove materials with boiling points higher than 1,4-BDO or target compound as a first high-boilers stream, to obtain a second 1,4-BDO or target compound-containing product stream; (c) subjecting the first high-boilers stream to wiped-film evaporation (WFE) to produce a WFE distillate, and the WFE distillate is subjected to the first intermediate column distillation procedure; (f) treating the second 1,4-BDO product stream with a hydrogenation reaction prior to performing step (d); (d) subjecting the second 1,4-BDO or target compound-containing product stream to a second intermediate distillation column procedure to remove materials with boiling points lower than 1,4-BDO or target compound, to produce a third 1,4-BDO or target compound-containing product stream and (e) subjecting the third 1,4-BDO or target compound-containing product stream to a second column distillation procedure to remove materials with boiling points higher than 1,4-BDO or target compound as a second high boilers stream, to produce a purified 1,4-BDO or target compound product.

In some embodiments, the purified 1,4-BDO or target compound product is collected as a distillate of the second column distillation procedure. In some embodiments, the purified 1,4-BDO or target compound product is collected from a side-draw of the second column distillation procedure.

In some embodiments, the second high boilers stream is subjected to the first intermediate column distillation procedure and/or second intermediate column distillation procedure. In some embodiments, when the purified 1,4-BDO or target compound can be collected from a side-draw of the second column distillation procedure, materials with boiling points lower than 1,4-BDO or target compound from the second column distillation procedure can be subjected to the first and/or second intermediate column distillation procedure.

In certain embodiments, the purified 1,4-BDO product from a distillation including a first distillation column procedure, an intermediate distillation column procedure, treating a 1,4-BDO-containing product stream with a hydrogenation reaction, and a second column distillation procedure is greater than 99% 1,4-BDO, 500 ppm to 1000 ppm 1,4-BDO monoacetate, 500 ppm to 1000 ppm 2-(4'-hydroxybutoxy)tetrahydrofuran and less than 10 ppm 2-pyrrolidone.

In certain embodiments, the purified 1,4-BDO product from a distillation including step (a), step (b), step (c), step (d) and step (e) is greater than 99% 1,4-BDO, 25 ppm to 75 ppm 1,4-BDO monoacetate, 200 ppm to 400 ppm 2-(4'-hydroxybutoxy)tetrahydrofuran, less than 5 ppm 2-pyrrolidone and less than 500 ppm water. In certain embodiments, the water content is less than 100 ppm.

In one embodiment, a distillation system includes a first distillation column receiving a crude 1,4-BDO or target compound mixture generating a first stream of materials with boiling points lower than 1,4-BDO or target compound and a 1,4-BDO or target compound-containing product stream, a second distillation column receiving the 1,4 BDO-containing product stream at a feed point and generating a second stream of materials with boiling points lower than 1,4-BDO or target compound, a first stream of materials with a boiling points higher than 1,4-BDO or target compound, and a purified 1,4-BDO or target compound product collected from a side-draw, a wiped-film evaporator receiving the first stream of materials with a boiling points higher than 1,4-BDO or target compound and generating a distillate, and the distillate feeding the second distillation column and a hydrogenation reactor constructed to treat the purified 1,4-BDO or target compound product generated by the second distillation column.

In one embodiment, a distillation system includes a first distillation column receiving a crude 1,4-BDO or target compound mixture generating a first stream of materials with boiling points lower than 1,4-BDO or target compound and a 1,4-BDO or target compound-containing product stream, a second distillation column receiving the 1,4 BDO-containing product stream at a feed point and generating a second stream of materials with boiling points lower than 1,4-BDO or target compound, a first stream of materials with a boiling points higher than 1,4-BDO or target compound, and a purified 1,4-BDO or target compound product collected from a side-draw, a wiped-film evaporator receiving the first stream of materials with a boiling points higher than 1,4-BDO or target compound and generating a distillate, and the distillate feeding the second distillation column and a hydrogenation reactor constructed to treat the 1,4-BDO or target compound-containing product stream prior to the 1,4-BDO or target compound-containing product stream being received by the second distillation column.

In one embodiment, a distillation system includes a first distillation column receiving a crude 1,4-BDO or target compound mixture generating a first stream of materials with boiling points lower than 1,4-BDO or target compound and a first 1,4-BDO or target compound-containing product stream, an intermediate distillation column receiving the first 1,4-BDO or target compound-containing product stream generating a first stream of materials with a boiling points higher than 1,4-BDO or target compound, and a second 1,4-BDO or target compound-containing product stream, a wiped-film evaporator receiving the first stream of materials with a boiling points higher than 1,4-BDO or target compound and generating a distillate, and the distillate feeding the intermediate distillation column; a second distillation column receiving the second 1,4 BDO-containing product stream at a feed point and generating a second stream of materials with boiling points lower than 1,4-BDO or target compound, a second stream of materials with a boiling points higher than 1,4-BDO or target compound, and a distilled 1,4-BDO or target compound product collected from a side-draw and a hydrogenation reactor constructed to treat the second 1,4-BDO or target compound-containing product stream prior to the second 1,4-BDO or target compound-containing product stream being received by the second distillation column.

In certain embodiments, the purified 1,4-BDO product from a distillation system including a first distillation column, an intermediate distillation column, a second distillation column, a wiped film evaporator and a hydrogenation unit is greater than 99% 1,4-BDO, 25 ppm to 75 ppm 1,4-BDO monoacetate, 200 ppm to 400 ppm 2-(4'-hydroxybutoxy)tetrahydrofuran and less than 5 ppm 2-pyrrolidone.

One embodiment of the distillation system includes a first distillation column receiving a crude 1,4-BDO or target compound mixture generating a first stream of materials with boiling points lower than 1,4-BDO or target compound and a first 1,4-BDO or target compound-containing product stream, a first intermediate distillation column receiving the first 1,4-BDO or target compound-containing product stream generating a first stream of materials with a boiling points higher than 1,4-BDO or target compound, and a second 1,4-BDO or target compound-containing product stream, and a wiped-film evaporator receiving the first stream of materials with a boiling points higher than 1,4-BDO or target compound (i.e., high boilers stream or bottoms purge) and generating a distillate, and the distillate feeding the first intermediate distillation column.

The system also includes a second intermediate distillation column receiving the second 1,4-BDO or target compound-containing product stream and generating a second stream of materials with boiling points lower than 1,4-BDO or target compound and a third 1,4-BDO or target compound-containing product stream; a second distillation column receiving the third 1,4-BDO or target compound-containing product stream at a feed point and generating, a second stream of materials with a boiling points higher than 1,4-BDO or target compound, and a purified 1,4-BDO or target compound product and a hydrogenation reactor constructed to treat the second 1,4-BDO or target compound-containing product stream prior to the second 1,4-BDO or target compound-containing product stream being received by the second intermediate distillation column. In certain embodiments, the purified 1,4-BDO or target compound product is generated from the top of the second distillate column. In certain embodiments, the purified 1,4-BDO or target compound product is generated from a side-draw.

Process and Systems

An example of the process for purifying 1,4-BDO or target compound derived from fermentation can include the steps of culturing a non-naturally occurring microbial organism to produce a 1,4-BDO or target compound in a fermentation broth, and subjecting the fermentation broth to one or more of the following procedures: biomass deactivation, centrifugation, microfiltration, ultrafiltration, nanofiltration, primary ion exchange, reverse osmosis, evaporation, crystallization, polishing, column distillation, wiped-film evaporation and hydrogenation.

In one embodiment, the process of purifying 1,4-BDO or target compound includes culturing a non-naturally occurring microbial organism to produce a 1,4-BDO or target compound in a fermentation broth, optionally subjecting the fermentation broth to biomass deactivation, and subjecting the fermentation broth to a separation procedure to produce a 1,4-BDO or target compound product. In certain embodiments, the separation procedure to produce a 1,4-BDO or target compound product includes centrifugation or filtration. In certain embodiments, the separation procedure to produce a 1,4-BDO or target compound product is centrifugation. In certain embodiments, the separation procedure to produce a 1,4-BDO or target compound product is centrifugation and filtration. In certain embodiments, the separation procedure to produce a 1,4-BDO or target compound product is filtration. In certain embodiments, where the separation procedure to produce a 1,4-BDO or target compound product is filtration, the filtration includes microfiltration, ultrafiltration, or nanofiltration; includes microfiltration and ultrafiltration; includes microfiltration and nanofiltration; includes ultrafiltration and nanofiltration. The filtration of the invention can be the recited steps with and without additional steps.

The process of purifying 1,4-BDO or target compound can further include subjecting the 1,4-BDO or target compound product to salt removal. The salt removal is primary ion exchange, as described above, in combination with any or all of the embodiments of the invention.

In one embodiment, the process of purifying 1,4-BDO or target compound includes culturing a non-naturally occurring microbial organism to produce a 1,4-BDO or target compound in a fermentation broth, optionally subjecting the fermentation broth to biomass deactivation, subjecting the fermentation broth to a separation procedure to produce a 1,4-BDO or target compound product, and subjecting the 1,4-BDO or target compound product to salt removal, where the salt removal is a primary ion exchange. In certain embodiments, the primary ion exchange includes cation exchange, anion exchange or mixed cation-anion exchange; cation exchange and anion exchange in any order; cation exchange or anion exchange. The separation includes centrifugation or filtration, and where the separation is filtration, the filtration includes microfiltration, ultrafiltration, or nanofiltration; includes microfiltration and ultrafiltration; includes microfiltration and nanofiltration; includes ultrafiltration and nanofiltration. The filtration of the invention can be the recited steps with and without additional steps.

For example, in one embodiment, the process of purifying 1,4-BDO or target compound includes culturing a non-naturally occurring microbial organism to produce a 1,4-BDO or target compound in a fermentation broth; subjecting the fermentation broth to biomass deactivation; subjecting the fermentation broth to a separation procedure to produce a 1,4-BDO or target compound product, where the separation procedure is filtration, and the filtration includes microfiltration and nanofiltration; and subjecting the 1,4-BDO or target compound product to ion exchange, where the ion exchange includes cation exchange, anion exchange or mixed cation-anion exchange.

The process of purifying 1,4-BDO or target compound can further include subjecting the 1,4-BDO or target compound product to water removal. The water removal is evaporation, as described above, in combination with any or all of the embodiments of the invention.

In one embodiment, the process of purifying 1,4-BDO or target compound includes culturing a non-naturally occurring microbial organism to produce a 1,4-BDO or target compound in a fermentation broth, optionally subjecting the fermentation broth to biomass deactivation, subjecting the fermentation broth to a separation procedure to produce a 1,4-BDO or target compound product, and subjecting the 1,4-BDO or target compound product to evaporation. Further, the primary ion exchange includes cation exchange, anion exchange or mixed cation-anion exchange; cation exchange and anion exchange in any order; anion exchange; or cation exchange. Further, the separation includes centrifugation or filtration, and where the separation is filtration, the filtration includes microfiltration, ultrafiltration, or nanofiltration; includes microfiltration and ultrafiltration; includes microfiltration and nanofiltration; includes ultrafiltration and nanofiltration. The filtration of the invention can be the recited steps with and without additional steps.

In one embodiment, the process of purifying 1,4-BDO or target compound includes culturing a non-naturally occurring microbial organism to produce a 1,4-BDO or target compound in a fermentation broth, optionally subjecting the fermentation broth to biomass deactivation, subjecting the fermentation broth to a separation procedure to produce a 1,4-BDO or target compound product, and subjecting the 1,4-BDO or target compound product to evaporation. Further, the separation includes centrifugation or filtration, and where the separation is filtration, the filtration includes microfiltration, ultrafiltration, or nanofiltration; includes microfiltration and ultrafiltration; includes microfiltration and nanofiltration; includes ultrafiltration and nanofiltration. The filtration of the invention can be the recited steps with and without additional steps.

For example, in one embodiment, the process of purifying 1,4-BDO or target compound includes culturing a non-naturally occurring microbial organism to produce a 1,4-BDO or target compound in a fermentation broth; subjecting the fermentation broth to biomass deactivation; subjecting the fermentation broth to a separation procedure to produce a 1,4-BDO or target compound product, where the separation procedure is filtration, and the filtration includes microfiltration and nanofiltration. The process further includes subjecting the 1,4-BDO or target compound product to ion exchange, where the ion exchange includes cation exchange, anion exchange or mixed cation-anion exchange; and further subjecting the 1,4-BDO or target compound product to evaporation.

The process of purifying 1,4-BDO or target compound can further include subjecting the 1,4-BDO or target compound product to salt removal. The salt removal can be crystallization, as described above, in combination with any or all of the embodiments of the invention.

In one embodiment, the process of purifying 1,4-BDO or target compound includes culturing a non-naturally occurring microbial organism to produce a 1,4-BDO or target compound in a fermentation broth, optionally subjecting the fermentation broth to biomass deactivation, subjecting the fermentation broth to a separation procedure to produce a 1,4-BDO or target compound product, subjecting the 1,4-BDO or target compound product to a primary ion exchange, subjecting the 1,4-BDO or target compound product to evaporation and subjecting the 1,4-BDO or target compound product to crystallization. Further, the primary ion exchange includes cation exchange, anion exchange or mixed cation-anion exchange; cation exchange and anion exchange in any order; anion exchange; or cation exchange. Further, the separation includes centrifugation or filtration, and where the separation is filtration, the filtration includes microfiltration, ultrafiltration, or nanofiltration; includes microfiltration and ultrafiltration; includes microfiltration and nanofiltration; includes ultrafiltration and nanofiltration. The filtration of the invention can be the recited steps with and without additional steps.

In one embodiment, the process of purifying 1,4-BDO or target compound includes culturing a non-naturally occurring microbial organism to produce a 1,4-BDO or target compound in a fermentation broth, optionally subjecting the fermentation broth to biomass deactivation, subjecting the fermentation broth to a separation procedure to produce a 1,4-BDO or target compound product, subjecting the 1,4-BDO or target compound product to evaporation and subjecting the 1,4-BDO or target compound product to crystallization. Further the separation includes centrifugation or filtration, and where the separation is filtration, the filtration includes microfiltration, ultrafiltration, or nanofiltration; includes microfiltration and ultrafiltration; includes microfiltration and nanofiltration; includes ultrafiltration and nanofiltration. The filtration of the invention can be the recited steps with and without additional steps.

In one embodiment, the process of purifying 1,4-BDO or target compound includes culturing a non-naturally occurring microbial organism to produce a 1,4-BDO or target compound in a fermentation broth, optionally subjecting the fermentation broth to biomass deactivation, subjecting the fermentation broth to a separation procedure to produce a 1,4-BDO or target compound product and subjecting the 1,4-BDO or target compound product to crystallization. Further, the separation includes centrifugation or filtration, and where the separation is filtration, the filtration includes microfiltration, ultrafiltration, or nanofiltration; includes microfiltration and ultrafiltration; includes microfiltration and nanofiltration; includes ultrafiltration and nanofiltration. The filtration of the invention can be the recited steps with and without additional steps.

The process of purifying 1,4-BDO or target compound can further include polishing, as described above, in combination with any or all of the embodiments of the invention.

In one embodiment, the process of purifying 1,4-BDO or target compound includes culturing a non-naturally occurring microbial organism to produce a 1,4-BDO or target compound in a fermentation broth, optionally subjecting the fermentation broth to biomass deactivation, subjecting the fermentation broth to a separation procedure to produce a 1,4-BDO or target compound product, subjecting the 1,4-BDO or target compound product to evaporation, subjecting the 1,4-BDO or target compound product to crystallization and subjecting the 1,4-BDO or target compound product to polishing. Further, the polishing includes polishing ion exchange and the polishing ion exchange includes cation exchange, anion exchange or a mixed cation-anion exchange; anion exchange; or cation exchange. Further, the separation includes centrifugation or filtration, and where the separation is filtration, the filtration includes microfiltration, ultrafiltration, or nanofiltration; includes microfiltration and ultrafiltration; includes microfiltration and nanofiltration; includes ultrafiltration and nanofiltration. The filtration of the invention can be the recited steps with and without additional steps.

In one embodiment, the process of purifying 1,4-BDO or target compound includes culturing a non-naturally occurring microbial organism to produce a 1,4-BDO or target compound in a fermentation broth, optionally subjecting the fermentation broth to biomass deactivation, subjecting the fermentation broth to a separation procedure to produce a 1,4-BDO or target compound product, subjecting the 1,4-BDO or target compound product to a primary ion exchange, subjecting the 1,4-BDO or target compound product to crystallization and subjecting the 1,4-BDO or target compound product to polishing. Further, the polishing includes polishing ion exchange and the polishing ion exchange includes cation exchange, anion exchange or a mixed cation-anion exchange; anion exchange; or cation exchange. Further, the primary ion exchange includes cation exchange, anion exchange or mixed cation-anion exchange; cation exchange and anion exchange in any order; anion exchange; or cation exchange. Further, the separation includes centrifugation or filtration, and where the separation is filtration, the filtration includes microfiltration, ultrafiltration, or nanofiltration; includes microfiltration and ultrafiltration; includes microfiltration and nanofiltration; includes ultrafiltration and nanofiltration. The filtration of the invention can be the recited steps with and without additional steps.

In one embodiment, the process of purifying 1,4-BDO or target compound includes culturing a non-naturally occurring microbial organism to produce a 1,4-BDO or target compound in a fermentation broth, optionally subjecting the fermentation broth to biomass deactivation, subjecting the fermentation broth to a separation procedure to produce a 1,4-BDO or target compound product, subjecting the 1,4-BDO or target compound product to a primary ion exchange, subjecting the 1,4-BDO or target compound product to evaporation and subjecting the 1,4-BDO or target compound product to polishing. Further, the polishing includes polishing ion exchange and the polishing ion exchange includes cation exchange, anion exchange or a mixed cation-anion exchange; anion exchange; or cation exchange. Further, the primary ion exchange includes cation exchange, anion exchange or mixed cation-anion exchange; cation exchange and anion exchange in any order; anion exchange; or cation exchange; where the separation includes centrifugation or filtration, and where the separation is filtration, the filtration includes microfiltration, ultrafiltration, or nanofiltration; includes microfiltration and ultrafiltration; includes microfiltration and nanofiltration; includes ultrafiltration and nanofiltration. The filtration of the invention can be the recited steps with and without additional steps.

In one embodiment, the process of purifying 1,4-BDO or target compound includes culturing a non-naturally occurring microbial organism to produce a 1,4-BDO or target compound in a fermentation broth, optionally subjecting the fermentation broth to biomass deactivation, subjecting the fermentation broth to a separation procedure to produce a 1,4-BDO or target compound product, subjecting the 1,4-BDO or target compound product to a primary ion exchange and subjecting the 1,4-BDO or target compound product to polishing. Further, the polishing includes polishing ion exchange and the polishing ion exchange includes cation exchange, anion exchange or a mixed cation-anion exchange; anion exchange; or cation exchange. Further, the primary ion exchange includes cation exchange, anion exchange or mixed cation-anion exchange; cation exchange and anion exchange in any order; anion exchange; or cation exchange; where the separation includes centrifugation or filtration, and where the separation is filtration, the filtration includes microfiltration, ultrafiltration, or nanofiltration; includes microfiltration and ultrafiltration; includes microfiltration and nanofiltration; includes ultrafiltration and nanofiltration. The filtration of the invention can be the recited steps with and without additional steps.

For example, in one embodiment, the process of purifying 1,4-BDO or target compound includes culturing a non-naturally occurring microbial organism to produce a 1,4-BDO or target compound in a fermentation broth; subjecting the fermentation broth to biomass deactivation; subjecting the fermentation broth to a separation procedure to produce a 1,4-BDO or target compound product, where the separation procedure is filtration, and the filtration includes microfiltration and nanofiltration. The process further includes subjecting the 1,4-BDO or target compound product to ion exchange, where the ion exchange includes cation exchange, anion exchange or mixed cation-anion exchange; and further subjecting the 1,4-BDO or target compound product to evaporation. The process further includes subjecting the 1,4-BDO or target compound product to polishing to produce a crude 1,4-BDO or target compound mixture, where the polishing is polishing ion exchange and the ion exchange is a strong base anion exchange.

For example, in one embodiment, the process of purifying 1,4-BDO or target compound includes culturing a non-naturally occurring microbial organism to produce a 1,4-BDO or target compound in a fermentation broth; subjecting the fermentation broth to biomass deactivation; subjecting the fermentation broth to a separation procedure to produce a 1,4-BDO or target compound product, where the separation procedure is filtration, and the filtration includes microfiltration and nanofiltration. The process further includes subjecting the 1,4-BDO or target compound product to ion exchange, where the ion exchange includes cation exchange, anion exchange or mixed cation-anion exchange; and further subjecting the 1,4-BDO or target compound product to evaporation. The process further includes subjecting the 1,4-BDO or target compound product to polishing to produce a crude 1,4-BDO or target compound mixture, where the polishing is polishing ion exchange and the ion exchange is a strong acid cation exchange and a strong base anion exchange.

The process of purifying 1,4-BDO or target compound can further includes distillation, as described above, in combination with any or all of the embodiments of the invention.

In one embodiment, the process of purifying 1,4-BDO or target compound includes culturing a non-naturally occurring microbial organism to produce a 1,4-BDO or target compound in a fermentation broth, optionally subjecting the fermentation broth to biomass deactivation, subjecting the fermentation broth to a separation procedure to produce a 1,4-BDO or target compound product, subjecting the 1,4-BDO or target compound product to a primary ion exchange, subjecting the 1,4-BDO or target compound product to evaporation, subjecting the 1,4-BDO or target compound product to crystallization, subjecting the 1,4-BDO or target compound product to polishing, and subjecting the 1,4-BDO or target compound product to distillation to produce a purified 1,4-BDO or target compound product, a first 1,4-BDO or target compound-containing product stream and a first high-boilers stream. Further, the polishing includes polishing ion exchange and the polishing ion exchange includes cation exchange, anion exchange or a mixed cation-anion exchange; anion exchange; or cation exchange. Further, the primary ion exchange includes cation exchange, anion exchange or mixed cation-anion exchange; cation exchange and anion exchange in any order; anion exchange; or cation exchange; where the separation includes centrifugation or filtration, and where the separation is filtration, the filtration includes microfiltration, ultrafiltration, or nanofiltration; includes microfiltration and ultrafiltration; includes microfiltration and nanofiltration; includes ultrafiltration and nanofiltration. The filtration of the invention can be the recited steps with and without additional steps.

In one embodiment, the process of purifying 1,4-BDO or target compound includes culturing a non-naturally occurring microbial organism to produce a 1,4-BDO or target compound in a fermentation broth, optionally subjecting the fermentation broth to biomass deactivation, subjecting the fermentation broth to a separation procedure to produce a 1,4-BDO or target compound product, subjecting the 1,4-BDO or target compound product to a primary ion exchange, subjecting the 1,4-BDO or target compound product to crystallization, subjecting the 1,4-BDO or target compound product to polishing and subjecting the 1,4-BDO or target compound product to distillation to produce a purified 1,4-BDO or target compound product, a first 1,4-BDO or target compound-containing product stream and a first high-boilers stream. Further, the polishing includes polishing ion exchange and the polishing ion exchange includes cation exchange, anion exchange or a mixed cation-anion exchange; anion exchange; or cation exchange. Further, the primary ion exchange includes cation exchange, anion exchange or mixed cation-anion exchange; cation exchange and anion exchange in any order; anion exchange; or cation exchange; where the separation includes centrifugation or filtration, and where the separation is filtration, the filtration includes microfiltration, ultrafiltration, or nanofiltration; includes microfiltration and ultrafiltration; includes microfiltration and nanofiltration; includes ultrafiltration and nanofiltration. The filtration of the invention can be the recited steps with and without additional steps.

In one embodiment, the process of purifying 1,4-BDO or target compound includes culturing a non-naturally occurring microbial organism to produce a 1,4-BDO or target compound in a fermentation broth, optionally subjecting the fermentation broth to biomass deactivation, subjecting the fermentation broth to a separation procedure to produce a 1,4-BDO or target compound product, subjecting the 1,4-BDO or target compound product to a primary ion exchange, subjecting the 1,4-BDO or target compound product to evaporation, subjecting the 1,4-BDO or target compound product to polishing and subjecting the 1,4-BDO or target compound product to distillation to produce a purified 1,4-BDO or target compound product, a first 1,4-BDO or target compound-containing product stream and a first high-boilers stream. Further, the polishing includes polishing ion exchange and the polishing ion exchange includes cation exchange, anion exchange or a mixed cation-anion exchange; anion exchange; or cation exchange. Further, the primary ion exchange includes cation exchange, anion exchange or mixed cation-anion exchange; cation exchange and anion exchange in any order; anion exchange; or cation exchange; where the separation includes centrifugation or filtration, and where the separation is filtration, the filtration includes microfiltration, ultrafiltration, or nanofiltration; includes microfiltration and ultrafiltration; includes microfiltration and nanofiltration; includes ultrafiltration and nanofiltration. The filtration of the invention can be the recited steps with and without additional steps.

In one embodiment, the process of purifying 1,4-BDO or target compound includes culturing a non-naturally occurring microbial organism to produce a 1,4-BDO or target compound in a fermentation broth, optionally subjecting the fermentation broth to biomass deactivation, subjecting the fermentation broth to a separation procedure to produce a 1,4-BDO or target compound product, subjecting the 1,4-BDO or target compound product to a primary ion exchange, subjecting the 1,4-BDO or target compound product to polishing and subjecting the 1,4-BDO or target compound product to distillation to produce a purified 1,4-BDO or target compound product, a first 1,4-BDO or target compound-containing product stream and a first high-boilers stream. Further, the polishing includes polishing ion exchange and the polishing ion exchange includes cation exchange, anion exchange or a mixed cation-anion exchange; anion exchange; or cation exchange. Further, the primary ion exchange includes cation exchange, anion exchange or mixed cation-anion exchange; cation exchange and anion exchange in any order; anion exchange; or cation exchange; where the separation includes centrifugation or filtration, and where the separation is filtration, the filtration includes microfiltration, ultrafiltration, or nanofiltration; includes microfiltration and ultrafiltration; includes microfiltration and nanofiltration; includes ultrafiltration and nanofiltration. The filtration of the invention can be the recited steps with and without additional steps.

In one embodiment, the process of purifying 1,4-BDO or target compound includes culturing a non-naturally occurring microbial organism to produce a 1,4-BDO or target compound in a fermentation broth, optionally subjecting the fermentation broth to biomass deactivation, subjecting the fermentation broth to a separation procedure to produce a 1,4-BDO or target compound product, subjecting the 1,4-BDO or target compound product to a primary ion exchange, subjecting the 1,4-BDO or target compound product to evaporation, subjecting the 1,4-BDO or target compound product to crystallization, and subjecting the 1,4-BDO or target compound product to distillation to produce a purified 1,4-BDO or target compound product, a first 1,4-BDO or target compound-containing product stream and a first high-boilers stream. Further, the primary ion exchange includes cation exchange, anion exchange or mixed cation-anion exchange; cation exchange and anion exchange in any order; anion exchange; or cation exchange; where the separation includes centrifugation or filtration, and where the separation is filtration, the filtration includes microfiltration, ultrafiltration, or nanofiltration; includes microfiltration and ultrafiltration; includes microfiltration and nanofiltration; includes ultrafiltration and nanofiltration. The filtration of the invention can be the recited steps with and without additional steps.

In one embodiment, the process of purifying 1,4-BDO or target compound includes culturing a non-naturally occurring microbial organism to produce a 1,4-BDO or target compound in a fermentation broth, optionally subjecting the fermentation broth to biomass deactivation, subjecting the fermentation broth to a separation procedure to produce a 1,4-BDO or target compound product, subjecting the 1,4-BDO or target compound product to a primary ion exchange, subjecting the 1,4-BDO or target compound product to crystallization, and subjecting the 1,4-BDO or target compound product to distillation to produce a purified 1,4-BDO or target compound product, a first 1,4-BDO or target compound-containing product stream and a first high-boilers stream. Further, the primary ion exchange includes cation exchange, anion exchange or mixed cation-anion exchange; cation exchange and anion exchange in any order; anion exchange; or cation exchange; where the separation includes centrifugation or filtration, and where the separation is filtration, the filtration includes microfiltration, ultrafiltration, or nanofiltration; includes microfiltration and ultrafiltration; includes microfiltration and nanofiltration; includes ultrafiltration and nanofiltration. The filtration of the invention can be the recited steps with and without additional steps.

In one embodiment, the process of purifying 1,4-BDO or target compound includes culturing a non-naturally occurring microbial organism to produce a 1,4-BDO or target compound in a fermentation broth, optionally subjecting the fermentation broth to biomass deactivation, subjecting the fermentation broth to a separation procedure to produce a 1,4-BDO or target compound product, subjecting the 1,4-BDO or target compound product to a primary ion exchange, subjecting the 1,4-BDO or target compound product to evaporation and subjecting the 1,4-BDO or target compound product to distillation to produce a purified 1,4-BDO or target compound product, a first 1,4-BDO or target compound-containing product stream and a first high-boilers stream. Further, the primary ion exchange includes cation exchange, anion exchange or mixed cation-anion exchange; cation exchange and anion exchange in any order; anion exchange; or cation exchange; where the separation includes centrifugation or filtration, and where the separation is filtration, the filtration includes microfiltration, ultrafiltration, or nanofiltration; includes microfiltration and ultrafiltration; includes microfiltration and nanofiltration; includes ultrafiltration and nanofiltration. The filtration of the invention can be the recited steps with and without additional steps.

In one embodiment, the process of purifying 1,4-BDO or target compound includes culturing a non-naturally occurring microbial organism to produce a 1,4-BDO or target compound in a fermentation broth, optionally subjecting the fermentation broth to biomass deactivation, subjecting the fermentation broth to a separation procedure to produce a 1,4-BDO or target compound product, subjecting the 1,4-BDO or target compound product to a primary ion exchange and subjecting the 1,4-BDO or target compound product to distillation to produce a purified 1,4-BDO or target compound product, a first 1,4-BDO or target compound-containing product stream and a first high-boilers stream. Further, the primary ion exchange includes cation exchange, anion exchange or mixed cation-anion exchange; cation exchange and anion exchange in any order; anion exchange; or cation exchange; where the separation includes centrifugation or filtration, and where the separation is filtration, the filtration includes microfiltration, ultrafiltration, or nanofiltration; includes microfiltration and ultrafiltration; includes microfiltration and nanofiltration; includes ultrafiltration and nanofiltration. The filtration of the invention can be the recited steps with and without additional steps.

For example, in one embodiment, the process of purifying 1,4-BDO or target compound includes culturing a non-naturally occurring microbial organism to produce a 1,4-BDO or target compound in a fermentation broth; subjecting the fermentation broth to biomass deactivation and subjecting the fermentation broth to a separation procedure to produce a 1,4-BDO or target compound product, where the separation procedure is filtration, and the filtration includes microfiltration and nanofiltration. The process further includes subjecting the 1,4-BDO or target compound product to ion exchange, where the ion exchange includes cation exchange, anion exchange or mixed cation-anion exchange. The process further includes subjecting the 1,4-BDO or target compound product to evaporation. The process further includes subjecting the 1,4-BDO or target compound product to polishing to produce a crude 1,4-BDO or target compound mixture, where the polishing is polishing ion exchange and the ion exchange is a strong base anion exchange. The process further includes subjecting the crude 1,4-BDO or target compound mixture to distillation, where the distillation includes subjecting crude 1,4-BDO or target compound mixture to a first column distillation procedure to remove materials with a boiling point lower than 1,4-BDO or target compound from the crude 1,4-BDO or target compound mixture to produce a first 1,4-BDO or target compound-containing product stream and subjecting the first 1,4-BDO or target compound-containing product stream to a second column distillation procedure to remove materials with boiling points higher than 1,4-BDO or target compound as a first high-boilers stream, to produce a purified 1,4-BDO or target compound product. Further, the purified 1,4-BDO or target compound product is collected from a side-draw of the second column distillation procedure.

For example, in one embodiment, the process of purifying 1,4-BDO or target compound includes culturing a non-naturally occurring microbial organism to produce a 1,4-BDO or target compound in a fermentation broth; subjecting the fermentation broth to biomass deactivation; subjecting the fermentation broth to a separation procedure to produce a 1,4-BDO or target compound product, where the separation procedure is filtration, and the filtration includes microfiltration and nanofiltration; subjecting the 1,4-BDO or target compound product to ion exchange, where the ion exchange includes cation exchange, anion exchange or mixed cation-anion exchange; further subjecting the 1,4-BDO or target compound product to evaporation. The process further includes subjecting the 1,4-BDO or target compound product to polishing to produce a crude 1,4-BDO or target compound mixture, where the polishing is polishing ion exchange and the ion exchange is a strong base anion exchange. The process further includes subjecting the crude 1,4-BDO or target compound mixture to distillation where the distillation includes subjecting crude 1,4-BDO or target compound mixture to a first column distillation procedure to remove materials with a boiling point lower than 1,4-BDO or target compound from the crude 1,4-BDO or target compound mixture to produce a first 1,4-BDO or target compound-containing product stream, subjecting the first 1,4-BDO or target compound-containing product stream to an intermediate column distillation procedure to remove materials with boiling points higher than 1,4-BDO or target compound as a second high-boilers stream, prior to performing the final distillation procedure, and subjecting the first 1,4-BDO or target compound-containing product stream to a second column distillation procedure to remove materials with boiling points higher than 1,4-BDO or target compound as a second high-boilers stream, to produce a purified 1,4-BDO or target compound product. Further, the purified 1,4-BDO or target compound product is collected from a side-draw of the second column distillation procedure.

The process of purifying 1,4-BDO or target compound can further includes wiped-film evaporation, as described above, in combination with any or all of the embodiments of the invention.

In one embodiment, the process of purifying 1,4-BDO or target compound includes culturing a non-naturally occurring microbial organism to produce a 1,4-BDO or target compound in a fermentation broth, optionally subjecting the fermentation broth to biomass deactivation, subjecting the fermentation broth to a separation procedure to produce a 1,4-BDO or target compound product, subjecting the 1,4-BDO or target compound product to a primary ion exchange, subjecting the 1,4-BDO or target compound product to evaporation, subjecting the 1,4-BDO or target compound product to crystallization, subjecting the 1,4-BDO or target compound product to polishing, and subjecting the 1,4-BDO or target compound product to distillation to produce a purified 1,4-BDO or target compound product, a first 1,4-BDO or target compound-containing product stream, a first high-boilers stream, and subjecting the first high-boilers stream to wiped-film evaporation to produce a wiped-film distillate. Further, the polishing includes polishing ion exchange and the polishing ion exchange includes cation exchange, anion exchange or a mixed cation-anion exchange; anion exchange; or cation exchange. Further, the primary ion exchange includes cation exchange, anion exchange or mixed cation-anion exchange; cation exchange and anion exchange in any order; anion exchange; or cation exchange; where the separation includes centrifugation or filtration, and where the separation is filtration, the filtration includes microfiltration, ultrafiltration, or nanofiltration; includes microfiltration and ultrafiltration; includes microfiltration and nanofiltration; includes ultrafiltration and nanofiltration. The filtration of the invention can be the recited steps with and without additional steps.

In one embodiment, the process of purifying 1,4-BDO or target compound includes culturing a non-naturally occurring microbial organism to produce a 1,4-BDO or target compound in a fermentation broth, optionally subjecting the fermentation broth to biomass deactivation, subjecting the fermentation broth to a separation procedure to produce a 1,4-BDO or target compound product, subjecting the 1,4-BDO or target compound product to a primary ion exchange, subjecting the 1,4-BDO or target compound product to crystallization, subjecting the 1,4-BDO or target compound product to polishing, subjecting the 1,4-BDO or target compound product to distillation to produce a purified 1,4-BDO or target compound product, a first 1,4-BDO or target compound-containing product stream and a first high-boilers stream and subjecting the first high-boilers stream to wiped-film evaporation to produce a wiped-film distillate. Further, the polishing includes polishing ion exchange and the polishing ion exchange includes cation exchange, anion exchange or a mixed cation-anion exchange; anion exchange; or cation exchange. Further, the primary ion exchange includes cation exchange, anion exchange or mixed cation-anion exchange; cation exchange and anion exchange in any order; anion exchange; or cation exchange; where the separation includes centrifugation or filtration, and where the separation is filtration, the filtration includes microfiltration, ultrafiltration, or nanofiltration; includes microfiltration and ultrafiltration; includes microfiltration and nanofiltration; includes ultrafiltration and nanofiltration. The filtration of the invention can be the recited steps with and without additional steps.

In one embodiment, the process of purifying 1,4-BDO or target compound includes culturing a non-naturally occurring microbial organism to produce a 1,4-BDO or target compound in a fermentation broth, optionally subjecting the fermentation broth to biomass deactivation, subjecting the fermentation broth to a separation procedure to produce a 1,4-BDO or target compound product, subjecting the 1,4-BDO or target compound product to a primary ion exchange, subjecting the 1,4-BDO or target compound product to evaporation, subjecting the 1,4-BDO or target compound product to polishing, subjecting the 1,4-BDO or target compound product to distillation to produce a purified 1,4-BDO or target compound product and subjecting the first high-boilers stream to wiped-film evaporation to produce a wiped-film distillate, a first 1,4-BDO or target compound-containing product stream and a first high-boilers stream. Further, the polishing includes polishing ion exchange and the polishing ion exchange includes cation exchange, anion exchange or a mixed cation-anion exchange; anion exchange; or cation exchange. Further, the primary ion exchange includes cation exchange, anion exchange or mixed cation-anion exchange; cation exchange and anion exchange in any order; anion exchange; or cation exchange; where the separation includes centrifugation or filtration, and where the separation is filtration, the filtration includes microfiltration, ultrafiltration, or nanofiltration; includes microfiltration and ultrafiltration; includes microfiltration and nanofiltration; includes ultrafiltration and nanofiltration. The filtration of the invention can be the recited steps with and without additional steps.

In one embodiment, the process of purifying 1,4-BDO or target compound includes culturing a non-naturally occurring microbial organism to produce a 1,4-BDO or target compound in a fermentation broth, optionally subjecting the fermentation broth to biomass deactivation, subjecting the fermentation broth to a separation procedure to produce a 1,4-BDO or target compound product, subjecting the 1,4-BDO or target compound product to a primary ion exchange, subjecting the 1,4-BDO or target compound product to polishing subjecting the 1,4-BDO or target compound product to distillation to produce a purified 1,4-BDO or target compound product, a first 1,4-BDO or target compound-containing product stream and a first high-boilers stream and subjecting the first high-boilers stream to wiped-film evaporation to produce a wiped-film distillate. Further, the polishing includes polishing ion exchange and the polishing ion exchange includes cation exchange, anion exchange or a mixed cation-anion exchange; anion exchange; or cation exchange. Further, the primary ion exchange includes cation exchange, anion exchange or mixed cation-anion exchange; cation exchange and anion exchange in any order; anion exchange; or cation exchange; where the separation includes centrifugation or filtration, and where the separation is filtration, the filtration includes microfiltration, ultrafiltration, or nanofiltration; includes microfiltration and ultrafiltration; includes microfiltration and nanofiltration; includes ultrafiltration and nanofiltration. The filtration of the invention can be the recited steps with and without additional steps.

In one embodiment, the process of purifying 1,4-BDO or target compound includes culturing a non-naturally occurring microbial organism to produce a 1,4-BDO or target compound in a fermentation broth, optionally subjecting the fermentation broth to biomass deactivation, subjecting the fermentation broth to a separation procedure to produce a 1,4-BDO or target compound product, subjecting the 1,4-BDO or target compound product to a primary ion exchange, subjecting the 1,4-BDO or target compound product to evaporation, subjecting the 1,4-BDO or target compound product to crystallization, subjecting the 1,4-BDO or target compound product to distillation to produce a purified 1,4-BDO or target compound product, a first 1,4-BDO or target compound-containing product stream and a first high-boilers stream and subjecting the first high-boilers stream to wiped-film evaporation to produce a wiped-film distillate. Further, the primary ion exchange includes cation exchange, anion exchange or mixed cation-anion exchange; cation exchange and anion exchange in any order; anion exchange; or cation exchange; where the separation includes centrifugation or filtration, and where the separation is filtration, the filtration includes microfiltration, ultrafiltration, or nanofiltration; includes microfiltration and ultrafiltration; includes microfiltration and nanofiltration; includes ultrafiltration and nanofiltration. The filtration of the invention can be the recited steps with and without additional steps.

In one embodiment, the process of purifying 1,4-BDO or target compound includes culturing a non-naturally occurring microbial organism to produce a 1,4-BDO or target compound in a fermentation broth, optionally subjecting the fermentation broth to biomass deactivation, subjecting the fermentation broth to a separation procedure to produce a 1,4-BDO or target compound product, subjecting the 1,4-BDO or target compound product to a primary ion exchange, subjecting the 1,4-BDO or target compound product to crystallization, subjecting the 1,4-BDO or target compound product to distillation to produce a purified 1,4-BDO or target compound product, a first 1,4-BDO or target compound-containing product stream and a first high-boilers stream and subjecting the first high-boilers stream to wiped-film evaporation to produce a wiped-film distillate. Further, the primary ion exchange includes cation exchange, anion exchange or mixed cation-anion exchange; cation exchange and anion exchange in any order; anion exchange; or cation exchange; where the separation includes centrifugation or filtration, and where the separation is filtration, the filtration includes microfiltration, ultrafiltration, or nanofiltration; includes microfiltration and ultrafiltration; includes microfiltration and nanofiltration; includes ultrafiltration and nanofiltration. The filtration of the invention can be the recited steps with and without additional steps.

In one embodiment, the process of purifying 1,4-BDO or target compound includes culturing a non-naturally occurring microbial organism to produce a 1,4-BDO or target compound in a fermentation broth, optionally subjecting the fermentation broth to biomass deactivation, subjecting the fermentation broth to a separation procedure to produce a 1,4-BDO or target compound product, subjecting the 1,4-BDO or target compound product to a primary ion exchange, subjecting the 1,4-BDO or target compound product to evaporation, subjecting the 1,4-BDO or target compound product to distillation to produce a purified 1,4-BDO or target compound product, a first 1,4-BDO or target compound-containing product stream and a first high-boilers stream and subjecting the first high-boilers stream to wiped-film evaporation to produce a wiped-film distillate. Further, the primary ion exchange includes cation exchange, anion exchange or mixed cation-anion exchange; cation exchange and anion exchange in any order; anion exchange; or cation exchange; where the separation includes centrifugation or filtration, and where the separation is filtration, the filtration includes microfiltration, ultrafiltration, or nanofiltration; includes microfiltration and ultrafiltration; includes microfiltration and nanofiltration; includes ultrafiltration and nanofiltration. The filtration of the invention can be the recited steps with and without additional steps.

In one embodiment, the process of purifying 1,4-BDO or target compound includes culturing a non-naturally occurring microbial organism to produce a 1,4-BDO or target compound in a fermentation broth, optionally subjecting the fermentation broth to biomass deactivation, subjecting the fermentation broth to a separation procedure to produce a 1,4-BDO or target compound product, subjecting the 1,4-BDO or target compound product to a primary ion exchange, subjecting the 1,4-BDO or target compound product to distillation to produce a purified 1,4-BDO or target compound product, a first 1,4-BDO or target compound-containing product stream and a first high-boilers stream and subjecting the first high-boilers stream to wiped-film evaporation to produce a wiped-film distillate. Further, the primary ion exchange includes cation exchange, anion exchange or mixed cation-anion exchange; cation exchange and anion exchange in any order; anion exchange; or cation exchange; where the separation includes centrifugation or filtration, and where the separation is filtration, the filtration includes microfiltration, ultrafiltration, or nanofiltration; includes microfiltration and ultrafiltration; includes microfiltration and nanofiltration; includes ultrafiltration and nanofiltration. The filtration of the invention can be the recited steps with and without additional steps.

For example, in one embodiment, the process of purifying 1,4-BDO or target compound includes culturing a non-naturally occurring microbial organism to produce a 1,4-BDO or target compound in a fermentation broth; subjecting the fermentation broth to biomass deactivation; subjecting the fermentation broth to a separation procedure to produce a 1,4-BDO or target compound product. Further, the separation procedure is filtration, where the filtration includes microfiltration and nanofiltration. The process further includes subjecting the 1,4-BDO or target compound product to ion exchange, where the ion exchange includes cation exchange, anion exchange or mixed cation-anion exchange. The process further includes subjecting the 1,4-BDO or target compound product to evaporation. The process further includes subjecting the 1,4-BDO or target compound product to polishing to produce a crude 1,4-BDO or target compound mixture, where the polishing is polishing ion exchange and the ion exchange is a strong base anion exchange. The process further includes subjecting the crude 1,4-BDO or target compound mixture, to distillation where the distillation includes subjecting crude 1,4-BDO or target compound mixture to a first column distillation procedure to remove materials with a boiling point lower than 1,4-BDO or target compound from the crude 1,4-BDO or target compound mixture to produce a first 1,4-BDO or target compound-containing product stream and subjecting the first 1,4-BDO or target compound-containing product stream to a second column distillation procedure to remove materials with boiling points higher than 1,4-BDO or target compound as a first high-boilers stream, to produce a purified 1,4-BDO or target compound product, where the purified 1,4-BDO or target compound product is collected from a side-draw of the second column distillation procedure and subjecting the first high-boilers stream to wiped-film evaporation (WFE) to produce a WFE distillate and subjecting the WFE distillate to the second column distillation procedure.

For example, in one embodiment, the process of purifying 1,4-BDO or target compound includes culturing a non-naturally occurring microbial organism to produce a 1,4-BDO or target compound in a fermentation broth; subjecting the fermentation broth to biomass deactivation; subjecting the fermentation broth to a separation procedure to produce a 1,4-BDO or target compound product, where the separation procedure is filtration, and the filtration includes microfiltration and nanofiltration. The process further includes subjecting the 1,4-BDO or target compound product to ion exchange, where the ion exchange includes cation exchange, anion exchange or mixed cation-anion exchange. The process further includes subjecting the 1,4-BDO or target compound product to evaporation. The process further includes subjecting the 1,4-BDO or target compound product to polishing to produce a crude 1,4-BDO or target compound mixture, where the polishing is polishing ion exchange and the ion exchange is a strong base anion exchange. The process further includes subjecting the crude 1,4-BDO or target compound mixture, to distillation where the distillation includes subjecting crude 1,4-BDO or target compound mixture to a first column distillation procedure to remove materials with a boiling point lower than 1,4-BDO or target compound from the crude 1,4-BDO or target compound mixture to produce a first 1,4-BDO or target compound-containing product stream, subjecting the first 1,4-BDO or target compound-containing product stream to an intermediate column distillation procedure to remove materials with boiling points higher than 1,4-BDO or target compound as a second high-boilers stream, prior to performing the final distillation procedure, and subjecting the first 1,4-BDO or target compound-containing product stream to a second column distillation procedure to remove materials with boiling points higher than 1,4-BDO or target compound as a second high-boilers stream, to produce a purified 1,4-BDO or target compound product, where the purified 1,4-BDO or target compound product is collected from a side-draw of the second column distillation procedure and subjecting the first high-boilers stream to wiped-film evaporation (WFE) to produce a WFE distillate and subjecting the WFE distillate to the intermediate column distillation procedure.

The process of purifying 1,4-BDO or target compound can further include hydrogenation, as described above, in combination with any or all of the embodiments of the invention.

In one embodiment, the process of purifying 1,4-BDO or target compound includes culturing a non-naturally occurring microbial organism to produce a 1,4-BDO or target compound in a fermentation broth, optionally subjecting the fermentation broth to biomass deactivation, subjecting the fermentation broth to a separation procedure to produce a 1,4-BDO or target compound product, subjecting the 1,4-BDO or target compound product to a primary ion exchange, subjecting the 1,4-BDO or target compound product to evaporation, subjecting the 1,4-BDO or target compound product to crystallization, subjecting the 1,4-BDO or target compound product to polishing, and subjecting the 1,4-BDO or target compound product to distillation to produce a purified 1,4-BDO or target compound product, a first 1,4-BDO or target compound-containing product stream, a first high-boilers stream, subjecting the first high-boilers stream to wiped-film evaporation to produce a wiped-film distillate and treating the first 1,4-BDO or target compound-containing product stream with a hydrogenation reaction. Further, the polishing includes polishing ion exchange and the polishing ion exchange includes cation exchange, anion exchange or a mixed cation-anion exchange; anion exchange; or cation exchange. Further, the primary ion exchange includes cation exchange, anion exchange or mixed cation-anion exchange; cation exchange and anion exchange in any order; anion exchange; or cation exchange; where the separation includes centrifugation or filtration, and where the separation is filtration, the filtration includes microfiltration, ultrafiltration, or nanofiltration; includes microfiltration and ultrafiltration; includes microfiltration and nanofiltration; includes ultrafiltration and nanofiltration. The filtration of the invention can be the recited steps with and without additional steps.

In one embodiment, the process of purifying 1,4-BDO or target compound includes culturing a non-naturally occurring microbial organism to produce a 1,4-BDO or target compound in a fermentation broth, optionally subjecting the fermentation broth to biomass deactivation, subjecting the fermentation broth to a separation procedure to produce a 1,4-BDO or target compound product, subjecting the 1,4-BDO or target compound product to a primary ion exchange, subjecting the 1,4-BDO or target compound product to crystallization, subjecting the 1,4-BDO or target compound product to polishing, subjecting the 1,4-BDO or target compound product to distillation to produce a purified 1,4-BDO or target compound product, a first 1,4-BDO or target compound-containing product stream and a first high-boilers stream, subjecting the first high-boilers stream to wiped-film evaporation to produce a wiped-film distillate and treating the first 1,4-BDO or target compound-containing product stream with a hydrogenation reaction. Further, the polishing includes polishing ion exchange and the polishing ion exchange includes cation exchange, anion exchange or a mixed cation-anion exchange; anion exchange; or cation exchange. Further, the primary ion exchange includes cation exchange, anion exchange or mixed cation-anion exchange; cation exchange and anion exchange in any order; anion exchange; or cation exchange; where the separation includes centrifugation or filtration, and where the separation is filtration, the filtration includes microfiltration, ultrafiltration, or nanofiltration; includes microfiltration and ultrafiltration; includes microfiltration and nanofiltration; includes ultrafiltration and nanofiltration. The filtration of the invention can be the recited steps with and without additional steps.

In one embodiment, the process of purifying 1,4-BDO or target compound includes culturing a non-naturally occurring microbial organism to produce a 1,4-BDO or target compound in a fermentation broth, optionally subjecting the fermentation broth to biomass deactivation, subjecting the fermentation broth to a separation procedure to produce a 1,4-BDO or target compound product, subjecting the 1,4-BDO or target compound product to a primary ion exchange, subjecting the 1,4-BDO or target compound product to evaporation, subjecting the 1,4-BDO or target compound product to polishing, subjecting the 1,4-BDO or target compound product to distillation to produce a purified 1,4-BDO or target compound product, subjecting the first high-boilers stream to wiped-film evaporation to produce a wiped-film distillate, a first 1,4-BDO or target compound-containing product stream and a first high-boilers stream and treating the first 1,4-BDO or target compound-containing product stream with a hydrogenation reaction. Further, the polishing includes polishing ion exchange and the polishing ion exchange includes cation exchange, anion exchange or a mixed cation-anion exchange; anion exchange; or cation exchange. Further, the primary ion exchange includes cation exchange, anion exchange or mixed cation-anion exchange; cation exchange and anion exchange in any order; anion exchange; or cation exchange; where the separation includes centrifugation or filtration, and where the separation is filtration, the filtration includes microfiltration, ultrafiltration, or nanofiltration; includes microfiltration and ultrafiltration; includes microfiltration and nanofiltration; includes ultrafiltration and nanofiltration. The filtration of the invention can be the recited steps with and without additional steps.

In one embodiment, the process of purifying 1,4-BDO or target compound includes culturing a non-naturally occurring microbial organism to produce a 1,4-BDO or target compound in a fermentation broth, optionally subjecting the fermentation broth to biomass deactivation, subjecting the fermentation broth to a separation procedure to produce a 1,4-BDO or target compound product, subjecting the 1,4-BDO or target compound product to a primary ion exchange, subjecting the 1,4-BDO or target compound product to polishing subjecting the 1,4-BDO or target compound product to distillation to produce a purified 1,4-BDO or target compound product, a first 1,4-BDO or target compound-containing product stream and a first high-boilers stream, subjecting the first high-boilers stream to wiped-film evaporation to produce a wiped-film distillate and treating the first 1,4-BDO or target compound-containing product stream with a hydrogenation reaction. Further, the polishing includes polishing ion exchange and the polishing ion exchange includes cation exchange, anion exchange or a mixed cation-anion exchange; anion exchange; or cation exchange. Further, the primary ion exchange includes cation exchange, anion exchange or mixed cation-anion exchange; cation exchange and anion exchange in any order; anion exchange; or cation exchange; where the separation includes centrifugation or filtration, and where the separation is filtration, the filtration includes microfiltration, ultrafiltration, or nanofiltration; includes microfiltration and ultrafiltration; includes microfiltration and nanofiltration; includes ultrafiltration and nanofiltration. The filtration of the invention can be the recited steps with and without additional steps.

In one embodiment, the process of purifying 1,4-BDO or target compound includes culturing a non-naturally occurring microbial organism to produce a 1,4-BDO or target compound in a fermentation broth, optionally subjecting the fermentation broth to biomass deactivation, subjecting the fermentation broth to a separation procedure to produce a 1,4-BDO or target compound product, subjecting the 1,4-BDO or target compound product to a primary ion exchange, subjecting the 1,4-BDO or target compound product to evaporation, subjecting the 1,4-BDO or target compound product to crystallization, subjecting the 1,4-BDO or target compound product to distillation to produce a purified 1,4-BDO or target compound product, a first 1,4-BDO or target compound-containing product stream and a first high-boilers stream, subjecting the first high-boilers stream to wiped-film evaporation to produce a wiped-film distillate and treating the first 1,4-BDO or target compound-containing product stream with a hydrogenation reaction. Further, the primary ion exchange includes cation exchange, anion exchange or mixed cation-anion exchange; cation exchange and anion exchange in any order; anion exchange; or cation exchange; where the separation includes centrifugation or filtration, and where the separation is filtration, the filtration includes microfiltration, ultrafiltration, or nanofiltration; includes microfiltration and ultrafiltration; includes microfiltration and nanofiltration; includes ultrafiltration and nanofiltration. The filtration of the invention can be the recited steps with and without additional steps.

In one embodiment, the process of purifying 1,4-BDO or target compound includes culturing a non-naturally occurring microbial organism to produce a 1,4-BDO or target compound in a fermentation broth, optionally subjecting the fermentation broth to biomass deactivation, subjecting the fermentation broth to a separation procedure to produce a 1,4-BDO or target compound product, subjecting the 1,4-BDO or target compound product to a primary ion exchange, subjecting the 1,4-BDO or target compound product to crystallization, subjecting the 1,4-BDO or target compound product to distillation to produce a purified 1,4-BDO or target compound product, a first 1,4-BDO or target compound-containing product stream and a first high-boilers stream, subjecting the first high-boilers stream to wiped-film evaporation to produce a wiped-film distillate and treating the first 1,4-BDO or target compound-containing product stream with a hydrogenation reaction. Further, the primary ion exchange includes cation exchange, anion exchange or mixed cation-anion exchange; cation exchange and anion exchange in any order; anion exchange; or cation exchange; where the separation includes centrifugation or filtration, and where the separation is filtration, the filtration includes microfiltration, ultrafiltration, or nanofiltration; includes microfiltration and ultrafiltration; includes microfiltration and nanofiltration; includes ultrafiltration and nanofiltration. The filtration of the invention can be the recited steps with and without additional steps.

In one embodiment, the process of purifying 1,4-BDO or target compound includes culturing a non-naturally occurring microbial organism to produce a 1,4-BDO or target compound in a fermentation broth, optionally subjecting the fermentation broth to biomass deactivation, subjecting the fermentation broth to a separation procedure to produce a 1,4-BDO or target compound product, subjecting the 1,4-BDO or target compound product to a primary ion exchange, subjecting the 1,4-BDO or target compound product to evaporation, subjecting the 1,4-BDO or target compound product to distillation to produce a purified 1,4-BDO or target compound product, a first 1,4-BDO or target compound-containing product stream and a first high-boilers stream, subjecting the first high-boilers stream to wiped-film evaporation to produce a wiped-film distillate and treating the first 1,4-BDO or target compound-containing product stream with a hydrogenation reaction. Further, the primary ion exchange includes cation exchange, anion exchange or mixed cation-anion exchange; cation exchange and anion exchange in any order; anion exchange; or cation exchange; where the separation includes centrifugation or filtration, and where the separation is filtration, the filtration includes microfiltration, ultrafiltration, or nanofiltration; includes microfiltration and ultrafiltration; includes microfiltration and nanofiltration; includes ultrafiltration and nanofiltration. The filtration of the invention can be the recited steps with and without additional steps.

In one embodiment, the process of purifying 1,4-BDO or target compound includes culturing a non-naturally occurring microbial organism to produce a 1,4-BDO or target compound in a fermentation broth, optionally subjecting the fermentation broth to biomass deactivation, subjecting the fermentation broth to a separation procedure to produce a 1,4-BDO or target compound product, subjecting the 1,4-BDO or target compound product to a primary ion exchange, subjecting the 1,4-BDO or target compound product to distillation to produce a purified 1,4-BDO or target compound product, a first 1,4-BDO or target compound-containing product stream and a first high-boilers stream, subjecting the first high-boilers stream to wiped-film evaporation to produce a wiped-film distillate and treating the first 1,4-BDO or target compound-containing product stream with a hydrogenation reaction. Further, the primary ion exchange includes cation exchange, anion exchange or mixed cation-anion exchange; cation exchange and anion exchange in any order; anion exchange; or cation exchange; where the separation includes centrifugation or filtration, and where the separation is filtration, the filtration includes microfiltration, ultrafiltration, or nanofiltration; includes microfiltration and ultrafiltration; includes microfiltration and nanofiltration; includes ultrafiltration and nanofiltration. The filtration of the invention can be the recited steps with and without additional steps.

For example, in one embodiment, the process of purifying 1,4-BDO or target compound includes culturing a non-naturally occurring microbial organism to produce a 1,4-BDO or target compound in a fermentation broth; subjecting the fermentation broth to biomass deactivation; subjecting the fermentation broth to a separation procedure to produce a 1,4-BDO or target compound product, where the separation procedure is filtration, and the filtration includes microfiltration and nanofiltration. The process further includes subjecting the 1,4-BDO or target compound product to ion exchange, where the ion exchange includes cation exchange, anion exchange or mixed cation-anion exchange. The process further includes subjecting the 1,4-BDO or target compound product to evaporation. The process further includes subjecting the 1,4-BDO or target compound product to polishing to produce a crude 1,4-BDO or target compound mixture, where the polishing is polishing ion exchange and the ion exchange is a strong base anion exchange. The process further includes distillation where the distillation includes subjecting crude 1,4-BDO or target compound mixture to a first column distillation procedure to remove materials with a boiling point lower than 1,4-BDO or target compound from the crude 1,4-BDO or target compound mixture to produce a first 1,4-BDO or target compound-containing product stream and subjecting the first 1,4-BDO or target compound-containing product stream to a second column distillation procedure to remove materials with boiling points higher than 1,4-BDO or target compound as a first high-boilers stream, to produce a purified 1,4-BDO or target compound product, where the purified 1,4-BDO or target compound product is collected from a side-draw of the second column distillation procedure, subjecting the first high-boilers stream to wiped-film evaporation (WFE) to produce a WFE distillate and subjecting the WFE distillate to the second column distillation procedure and treating the purified 1,4-BDO or target compound product with a hydrogenation.

For example, in one embodiment, the process of purifying 1,4-BDO or target compound includes culturing a non-naturally occurring microbial organism to produce a 1,4-BDO or target compound in a fermentation broth; subjecting the fermentation broth to biomass deactivation; subjecting the fermentation broth to a separation procedure to produce a 1,4-BDO or target compound product. Further, the separation procedure is filtration, where the filtration includes microfiltration and nanofiltration. The process further includes subjecting the 1,4-BDO or target compound product to ion exchange, where the ion exchange includes cation exchange, anion exchange or mixed cation-anion exchange. The process further includes subjecting the 1,4-BDO or target compound product to evaporation. The process further includes subjecting the 1,4-BDO or target compound product to polishing to produce a crude 1,4-BDO or target compound mixture, where the polishing is polishing ion exchange and the ion exchange is a strong base anion exchange. The process further includes distillation where the distillation includes subjecting crude 1,4-BDO or target compound mixture to a first column distillation procedure to remove materials with a boiling point lower than 1,4-BDO or target compound from the crude 1,4-BDO or target compound mixture to produce a first 1,4-BDO or target compound-containing product stream, subjecting the first 1,4-BDO or target compound-containing product stream to an intermediate column distillation procedure to remove materials with boiling points higher than 1,4-BDO or target compound as a second high-boilers stream, prior to performing the final distillation procedure, and subjecting the first 1,4-BDO or target compound-containing product stream to a second column distillation procedure to remove materials with boiling points higher than 1,4-BDO or target compound as a second high-boilers stream, to produce a purified 1,4-BDO or target compound product, where the purified 1,4-BDO or target compound product is collected from a side-draw of the second column distillation procedure, subjecting the first high-boilers stream to wiped-film evaporation (WFE) to produce a WFE distillate and subjecting the WFE distillate to the intermediate column distillation procedure and treating the 1,4-BDO or target compound-containing product stream with a hydrogenation reaction prior to performing the final distillation procedure.

In certain embodiments of the process and systems described herein, the amount of fermentation broth is at least 20 L, at least 25 L, at least 80 L, at least 1000 L, at least 13,000 L, at least 50,000 L, at least 100,000 L, at least 600,000 L at least, 1,200,000 L, or at least 2,000,000 L or more.

Figure 1B:
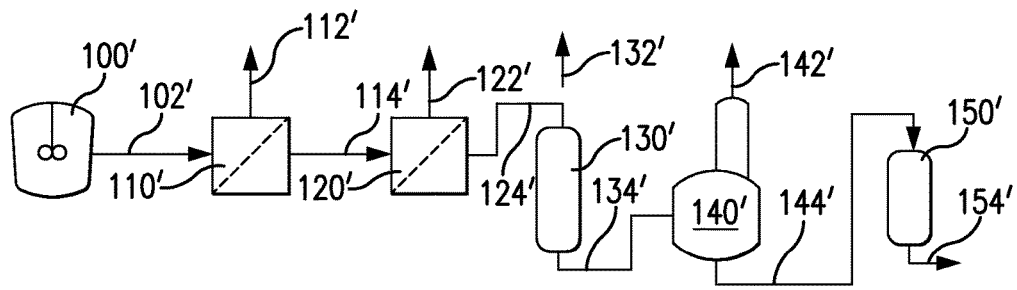
FIG. 1B depicts an exemplary system for producing a crude 1,4-BDO mixture from 1,4-BDO in a fermentation broth with two filtrations, primary ion exchange, evaporation and polishing ion exchange.

An example system to produce crude 1,4-BDO mixture is depicted in FIG. 1A. A fermentor 100 produces a 1,4-BDO in a fermentation broth 102 which is fed to a first filtration unit 110. The first filtration unit removes the biomass and other solids 112 from a 1,4-BDO product 114. The 1,4-BDO product 114 is then fed to a nanofiltration unit 120, where a retentate 122 is removed from the 1,4-BDO product 124. The 1,4-BDO product 124 is next fed to a primary ion exchange unit 130, where it is treated with a cation exchange resin and treatment with an anion exchange resin to remove salts 132 from the 1,4-BDO product 134. The 1,4-BDO product 134 is then fed to an evaporation unit 140 to remove excess water 142 to produce crude 1,4-BDO mixture 144, which is about 80% 1,4-BDO and about 20% water, with minor amounts of a number of other materials. Another example is depicted in FIG. 1B, which adds a polishing ion exchange unit 150' to example of FIG. 1A. The polishing ion exchange 150' unit is added after the evaporator 140', producing the crude 1,4-BDO mixture 154'. In one example, the first filtration unit 110 or 110' is microfiltration, and in other examples the first filtration unit 110 or 110' is ultrafiltration.

Figure 2A:
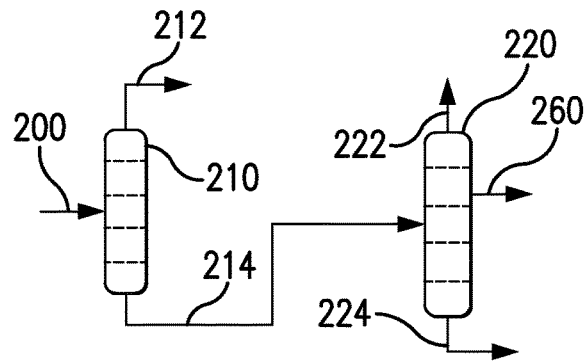
FIG. 2A depicts an exemplary two-column distillation system with a side-draw.

An example of a two column distillation system is depicted in FIG. 2A. The crude 1,4-BDO mixture 200 is fed to the first distillation column 210, where light materials 212 (materials with boiling points lower than 1,4-BDO) are removed from the top of the first column 210. A 1,4-BDO-containing product stream 214 exits the bottom of the first column and is fed to an second distillation column 220. Heavy materials 224 (materials with boiling points higher than 1,4-BDO) are removed from the bottom of the second column 220, and light materials 222 are removed from the top of the second column 220. The purified 1,4-BDO product 260 is collected from a side-draw of column 220.

Figure 2B:
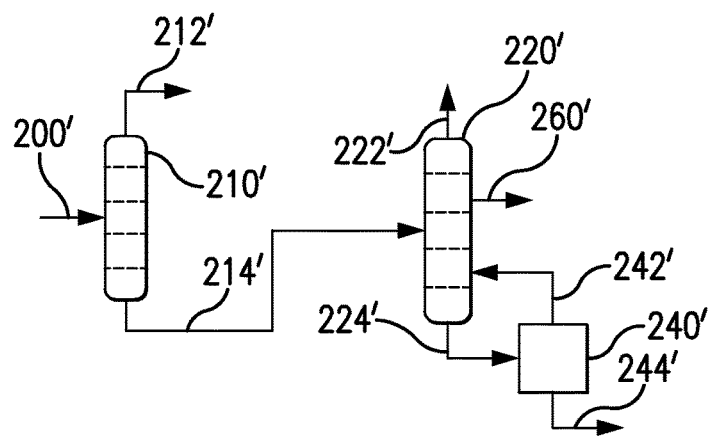
FIG. 2B depicts an exemplary two-column distillation system with a side-draw and a wiped-film evaporator.

An example depicted in FIG. 2B adds to the example of FIG. 2A, a wiped-film evaporator 240'. The heavy material 224' is fed to a wiped-film evaporator 240', where a distillate 242' and heavy material 244' are produced. The distillate 242' is fed to the second distillation column 220'.

Figure 2C:
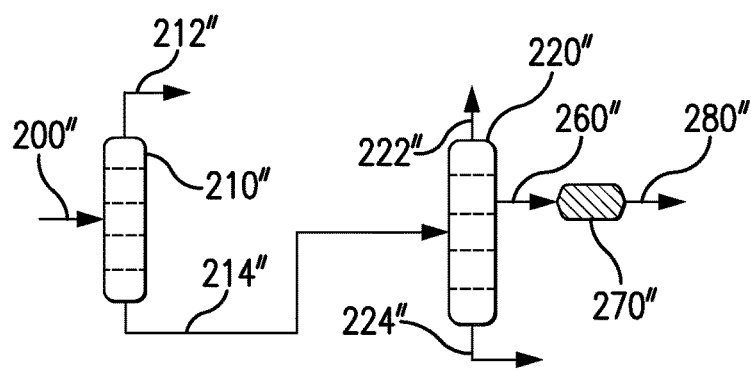
FIG. 2C depicts an exemplary two-column distillation system with a side-draw and hydrogenation unit.

An example depicted in FIG. 2C adds to the example of FIG. 2A, a hydrogenation unit 270". The purified 1,4-BDO product 260" is fed to the hydrogenation unit 270" and produces a purified 1,4-BDO product 280".

Figure 2D:
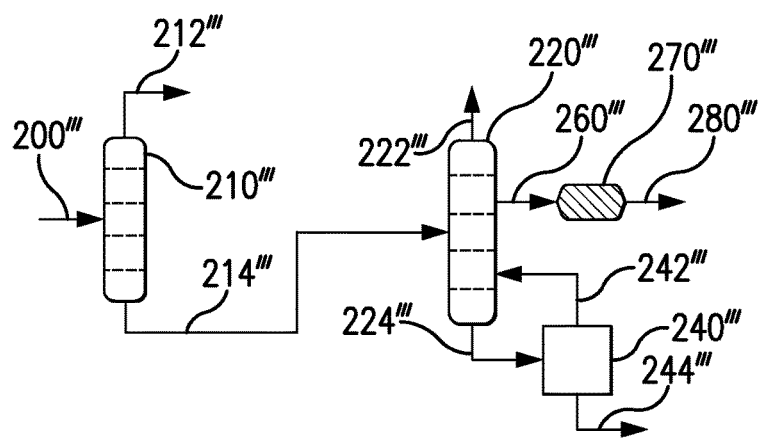
FIG. 2D depicts an exemplary two-column distillation system with a side-draw, a wiped-film evaporator and hydrogenation unit.

An example depicted in FIG. 2D adds to the example of FIG. 2C, a wiped-film evaporator 240'''. The heavy material 224''' is fed to a wiped-film evaporator 240''', where a distillate 242''' and heavy material 244''' are produced. The distillate 242''' is fed to the second distillation column 220'''.

Figure 2E:
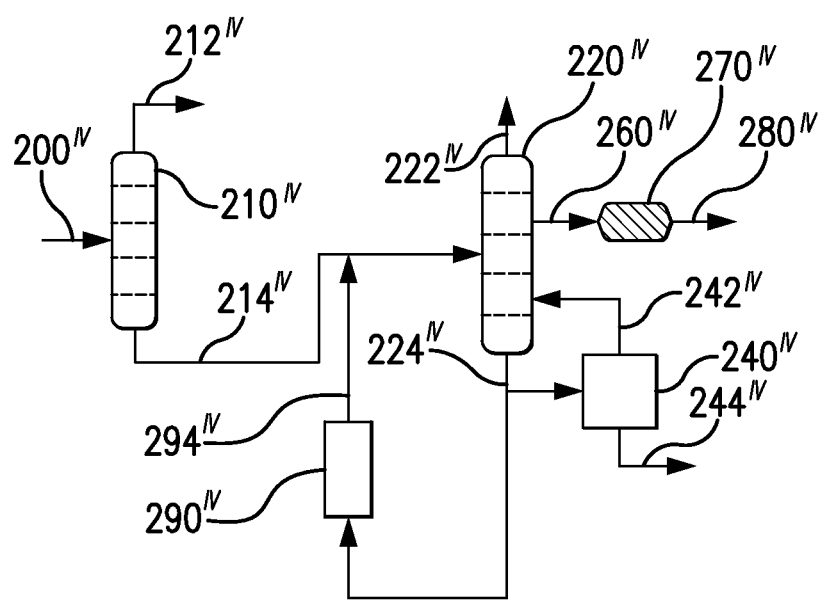
FIG. 2E depicts an exemplary two-column distillation system with a side-draw, a wiped-film evaporator, hydrogenation unit, and a forced recirculation reboiler.

An example depicted in FIG. 2E adds to the example of FIG. 2D, a forced recirculation reboiler $290^{IV}$. The heavy material $224^{IV}$ from the second distillation column $220^{IV}$ is fed to a forced recirculation reboiler $290^{IV}$, where a vapor $294^{IV}$ is produced. The vapor $294^{IV}$ is fed, at least in part, to the second column $220^{IV}$. As shown in FIG. 2E, the vapor $294^{IV}$ is fed to the feed $214^{IV}$. However, in other embodiments (not shown in FIG. 2D), the vapor $294^{IV}$ can be fed to the sump of column $220^{IV}$.

In yet other embodiments, the heavy material from the second column of a two column distillation system (such as shown, for instance, in any of FIGS. 2A to 2D) is fed to a forced recirculation reboiler. The forced recirculation reboiler can produce a vapor that is fed, at least in part, back into the second column (e.g., sump) or to the feed to the second column.

Figure 3A:
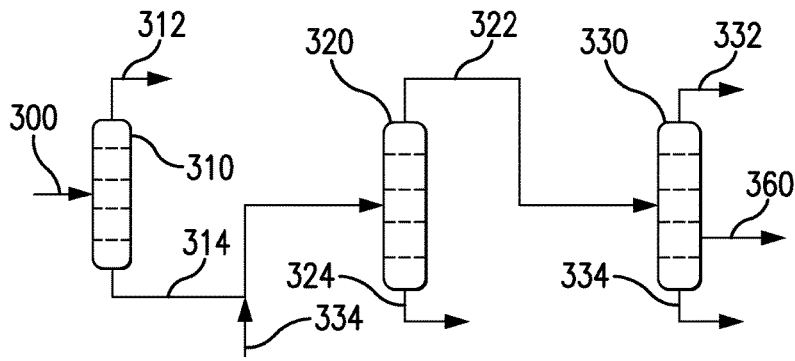
FIG. 3A depicts an exemplary three-column distillation system with a side-draw.

An example of a three column distillation system is depicted in FIG. 3A. The crude 1,4-BDO mixture 300 is fed to the first distillation column 310, where light materials 312 (materials with boiling points lower than 1,4-BDO) are removed from the top of the first column 310. A 1,4-BDO-containing product stream 314 exits the bottom of the first column and is fed to a second distillation column 320. Heavy materials 324 (materials with boiling points higher than 1,4-BDO) are removed from the bottom of the second column 320, and a second 1,4-BDO-containing product stream 322 exits from the top of the second column 320. The second 1,4-BDO-containing product stream 322 is fed to a third distillation column 330. The third distillation column 330 removes light materials 332 from the top of the column 330 and heavy materials 334 from the bottom of column 330, with the heavy materials 334 being fed to the second distillation column 320. The purified 1,4-BDO product 360 is collected from a side-draw of column 330.

Figure 3B:
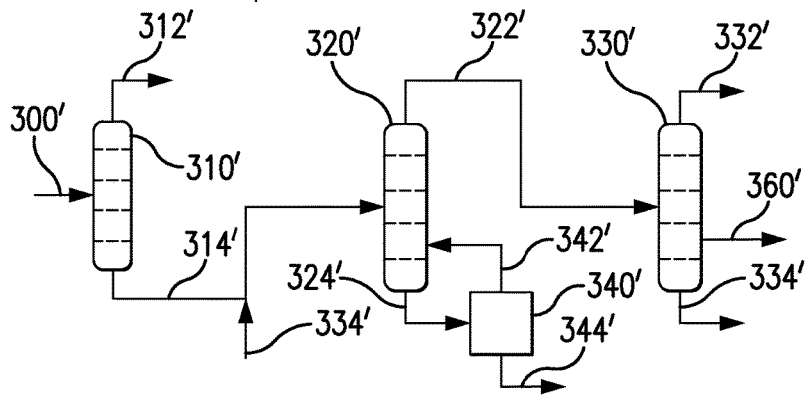
FIG. 3B depicts an exemplary three-column distillation system with a side-draw and a wiped-film evaporator.

An example depicted in FIG. 3B adds to the example of FIG. 3A, a wiped-film evaporator 340'. The heavy material 324' is fed to a wiped-film evaporator 340', where a distillate 342' and heavy material 344' are produced. The distillate 342' is fed to the second distillation column 320'.

Figure 3C:
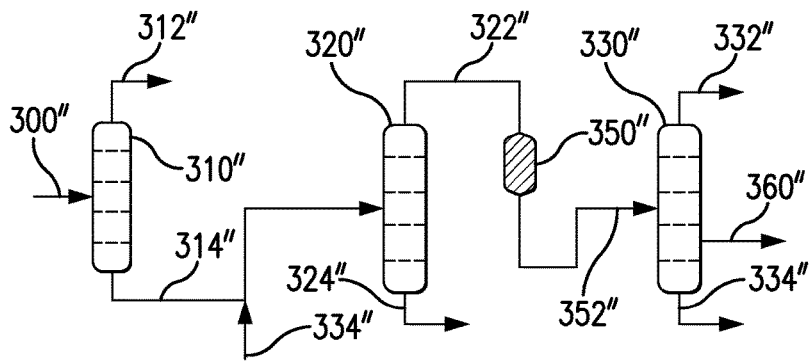
FIG. 3C depicts an exemplary three-column distillation system with a side-draw and hydrogenation unit.

An example depicted in FIG. 3C adds to the example of FIG. 3A, a hydrogenation unit 350". The 1,4-BDO-containing product stream 322" is fed to the hydrogenation unit 350" and sends the stream 352" to the third distillation column 330".

Figure 3D:
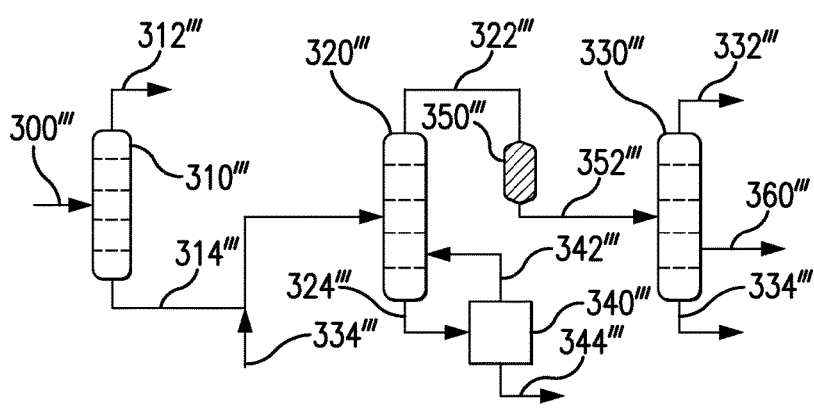
FIG. 3D depicts an exemplary three-column distillation system with a side-draw, a wiped-film evaporator and hydrogenation unit.

An example depicted in FIG. 3D adds to the example of FIG. 3C, a wiped-film evaporator 340'''. The heavy material 324''' is fed to a wiped-film evaporator 340''', where a distillate 342''' and heavy material 344''' are produced. The distillate 342''' is fed to the second distillation column 320'''.

Figure 3E:
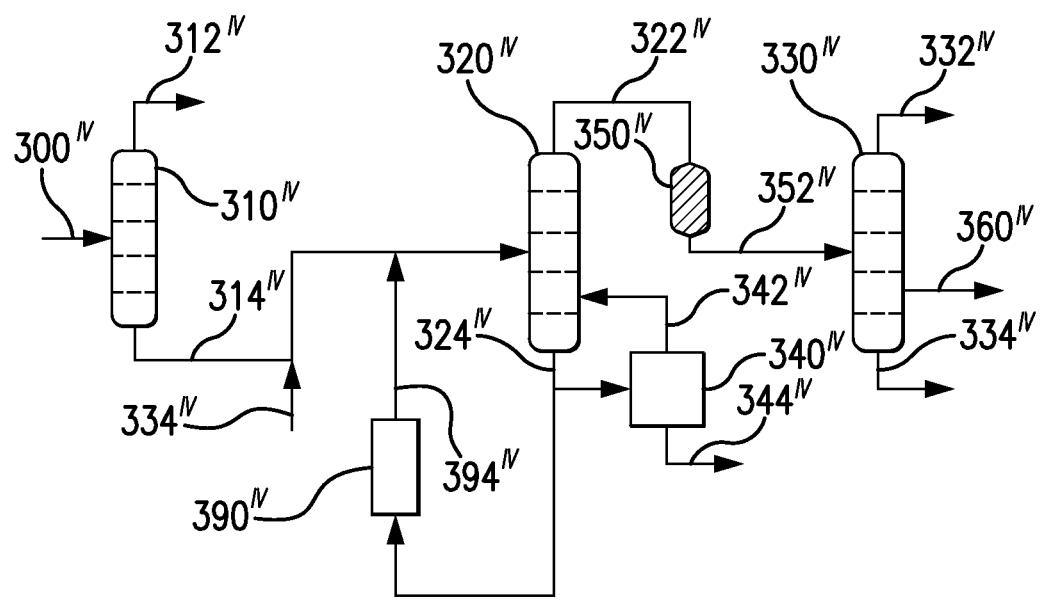
FIG. 3E depicts an exemplary three-column distillation system with a side-draw, a wiped-film evaporator, a hydrogenation unit, and a forced recirculation reboiler.

An example depicted in FIG. 3E adds to the examples of FIG. 3D, a forced recirculation reboiler $390^{IV}$. The heavy material $324^{IV}$ from the second distillation column $320^{IV}$ is fed to a forced recirculation reboiler $390^{IV}$, where a vapor $394^{IV}$ is produced. The vapor $394^{IV}$ is fed, at least in part, to the second distillation column $320^{IV}$. As shown in FIG. 3E, the vapor $394^{IV}$ is fed to the feed $314^{IV}$. In certain other embodiments, the vapor $394^{IV}$ is fed to the sump of column $320^{IV}$.

In yet other embodiments of a three column distillation system provided herein, the heavy material purged from an intermediate column (such as, for instance, any of heavy material 324, 324', 324" or 324''' as shown in FIGS. 3A to 3D, respectively) is fed to a forced recirculation reboiler. The forced recirculation reboiler can produce a vapor that is fed, at least in part, back into the intermediate column (e.g., sump) or to the feed to the intermediate column.

Figure 4A:
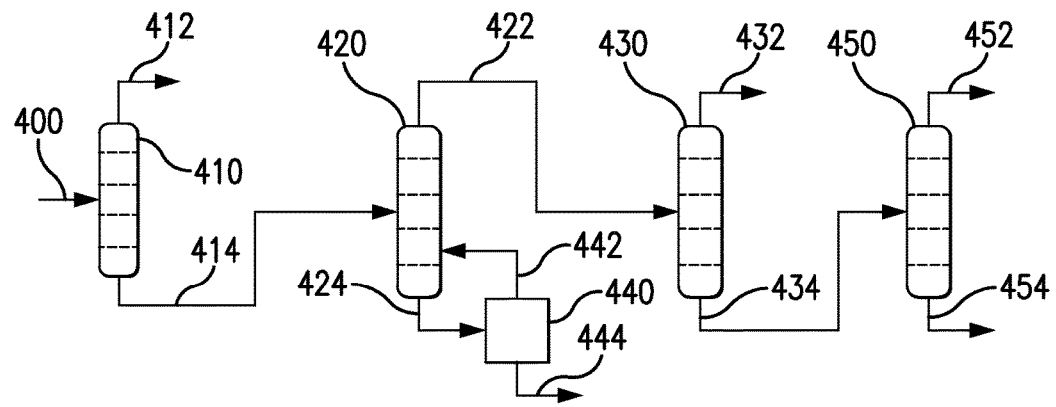
FIG. 4A depicts an exemplary four-column distillation system with a wiped film evaporator.

An example of a four column distillation system is depicted in FIG. 4A. The crude 1,4-BDO mixture 400 is fed to the first distillation column 410, where light materials 412 (materials with boiling points lower than 1,4-BDO) are removed from the top of the first column 410. A 1,4-BDO-containing product stream 414 exits the bottom of the first column and is fed to an intermediate distillation column 420. Heavy materials 424 (materials with boiling points higher than 1,4-BDO) are removed from the bottom of the second column 420, and a 1,4 BDO-containing product stream 422 exits from the top of the second column 420. The heavy material 424 is fed to a wiped-film evaporator 440, where a distillate 442 and heavy material 444 are produced. The distillate 442 is fed to the second distillation column 420. The 1,4-BDO-containing product stream 422 is fed to a third distillation column 430. Distillation column 430 removes light materials 432 from the top of the column 430 and a third 1,4-BDO-containing product stream 434 from the bottom of column 430. The third 1,4-BDO-containing product stream 434 is fed to a fourth distillation column 450. The purified 1,4-BDO product 452 is collected from the top of column 450, and heavy materials 454 exit from the bottom of column 450.

Figure 4B:
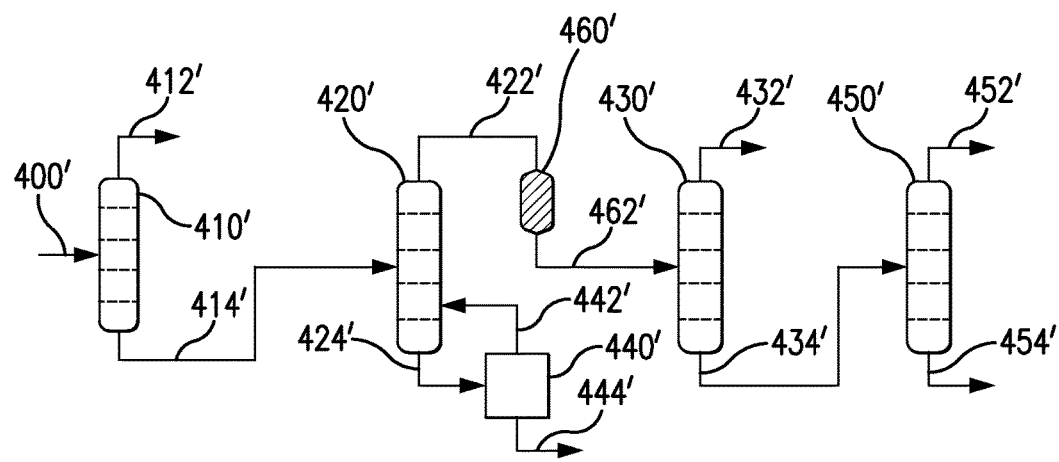
FIG. 4B depicts an exemplary four-column distillation system with a hydrogenation unit and a wiped-film evaporator.

An example depicted in FIG. 4B adds a hydrogenation unit 460' to the system of FIG. 4A. The 1,4-BDO-containing product stream 422' is fed to the hydrogenation unit 460' and sends the stream 462" to the third distillation column 430'.

Figure 4C:
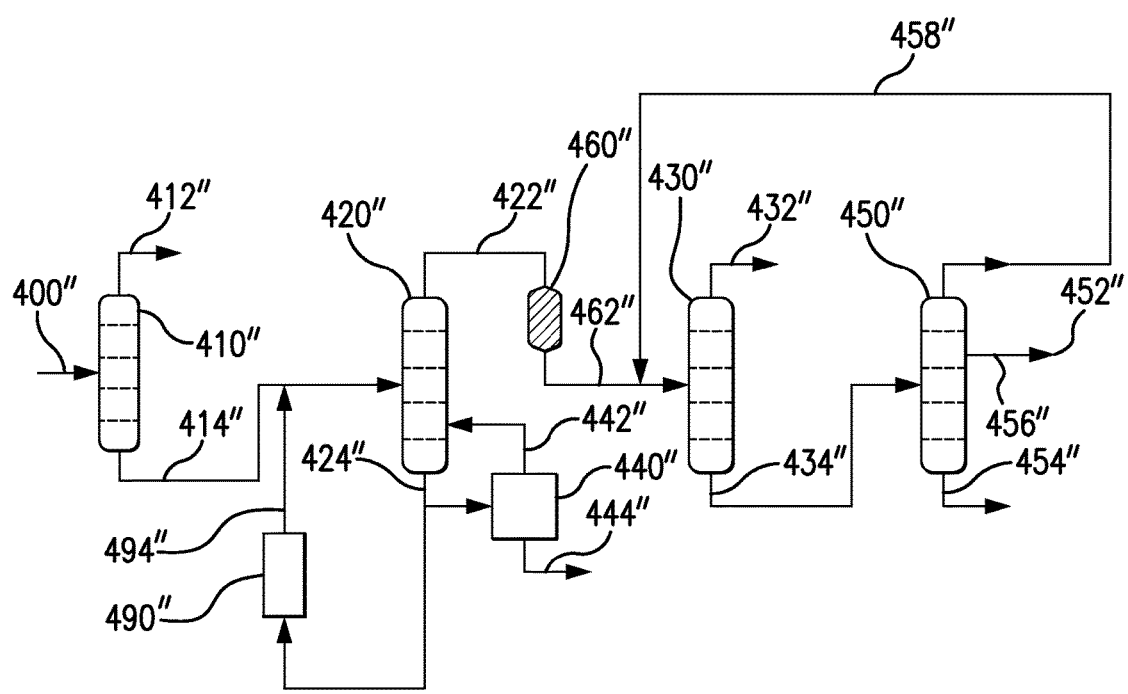
FIG. 4C depicts an exemplary four-column distillation system with a side draw, a hydrogenation unit, a wiped-film evaporator, a forced recirculation reboiler and a BDO recovery stream recycling the distillate of column four into the feed stream of column three.

An example depicted in FIG. 4C adds a forced recirculation reboiler 490" to the system of FIG. 4B. The heavy material 424" from the second column 420" is fed to a forced recirculation reboiler 490", where a vapor 494" is produced. The vapor 494" is fed, at least in part, to the second distillation column 420". As shown in FIG. 4C, the vapor 494" is fed to the feed 414". However, a person of ordinary skill will understand that the vapor 494" can be fed to the sump of column 420".

In yet other embodiments of a four column distillation system provided herein, the heavy material purged from an intermediate column (such as, for instance, any of heavy material 424 or 424' as shown in FIGS. 4A to 4B, respectively) is fed to a forced recirculation reboiler. The forced recirculation reboiler can produce a vapor that is fed, at least in part, back into the intermediate column (e.g., sump) or to the feed to the intermediate column.

In certain embodiments of a two, three or four column distillation system provided herein, a forced recirculation reboiler is used in the absence of a hydrogenation unit and/or wiped film evaporator.

In the example depicted in FIG. 4C, the purified 1,4-BDO product 452" is collected from a side draw 456". The distillate 458" is fed to the stream 462" to the third distillation column 430". In certain other embodiments of a four column system, the distillate 458" can be fed to the feed-stream of the first column 410", the second column 420", or the fourth column 450".

The last column of a two, three, or four-column distillation system of as provided herein can have a side draw. The side draw can be positioned above the feed to the last column, or the side draw can be positioned below the feed to the last column.

In some embodiments, the purified 1,4-BDO product is collected from a side draw from the last column of a two column system. In certain embodiments, the side draw from the last column of a two column system is positioned above the feed to the column, such as depicted, for example, in FIG. 2A where side draw 260 is above the feed to the second column.

In some embodiments, the purified 1,4-BDO product is collected from a side draw from the last column of a three column system. In certain embodiments, the side draw from the last column of a three column system is positioned below the feed to the column, such as depicted, for example, in FIG. 3A where side draw 360 is below the feed to the last column.

In some embodiments, the purified 1,4-BDO product is collected from a side draw from the last column of a four column system. In certain embodiments, the side draw from the last column of a four column system is positioned above the feed to the column. For example, a side draw from the fourth column of a four-column distillation system is depicted as side draw 456" in FIG. 4C that is above the feed to the last column.

An example of an embodiment of the present disclosure can be any of the examples of FIG. 1A or FIG. 1B combined with any of the examples of FIGS. 2A to 2E, of FIGS. 3A to 3E, or of FIGS. 4A to 4C. For example, an embodiment can the combination of FIG. 1B with FIG. 2B, or FIG. 1B with FIG. 3D.

Each column in a two-column, three-column, or four-column distillation system of this disclosure can optionally be combined with a condenser. The condenser can be an air-cooled condenser, such as an air condenser, a Snyder column or a Widmer column, or a water-cooled condenser, such as a Liebig condenser, a West condenser, an Allihn condenser, a Davies condenser, a Graham condenser, a Coil condenser, a Dimroth condenser, a Spiral condenser, a Friedrichs condenser or any other condenser known in the art. The condenser receives the low-boilers stream from a column in a two-column, three-column, or four-column distillation system of this disclosure and generates a condensate. In some embodiments, the condensate is at last in part recycled back into the column ("reflux"). The recycled condensate can be added to the feed to a column or it can be added to a column directly, e.g., to the sump of a column.

Each column in a two-column, three-column, or four-column distillation system of this disclosure can optionally be combined with a reboiler. The reboiler can, for example, be a forced recirculation reboiler, a kettle reboiler, a thermosyphon reboiler, a fired reboiler or any other type of reboiler known in the art. The reboiler receives the bottom purge of a column in a two-column, three-column, or four-column distillation system of this disclosure and generates a vapor. In certain embodiments, the vapor is, at least in part, recycled back into a column of the system. The recycled vapor can be added to the feed to a column or it can be added to a column directly, e.g., to the sump of the column.

In some embodiments, the bottom purge of the second column of a two-column distillation system or the first intermediate column of a three or four-column distillation system is fed into a forced recirculation reboiler, which generates a vapor. In certain embodiments, the vapor is, at least in part, recycled back into the system. In certain embodiments, the vapor is recycled back into the second column in a two-column system or the first intermediate column in a three or four-column system.

In some embodiments, the bottom purge of the second column of a two-column distillation system or the first intermediate column of a three or four-column distillation system is fed into a wiped-film evaporator, which generates a distillate. In certain embodiments, the distillate is, at least in part, recycled back into the system. In certain embodiments, the distillate is recycled back into the second column of a two-column system or the first intermediate column of a three of four-column system. In certain other embodiments, the distillate is recycled into the feed to a hydrogenation unit in a three or four-column system.

In some embodiments, at least a part of the bottom purge of the second column of a two-column distillation system or of the first intermediate column of a three or four-column distillation system is fed into a forced recirculation reboiler, which generates a vapor, and another part is fed into a wiped-film evaporator, which generates a distillate. In certain embodiments, the vapor is recycled back into the second column in a two-column system or into the first intermediate column in a three or four-column system. In certain embodiments, the distillate is recycled back into the second column in a two-column system or into the first intermediate column in a three or four-column system. In certain embodiments, the distillate generated is recycled into the feed to the hydrogenation unit in a three- or four column system.

UV absorbance is a measure of the quality of the 1,4-BDO product indicative of the amount of impurities present. UV absorbance can also be measured of 1,4-BDO containing process streams at various points in a given distillation system.

In some embodiments of the processes of this disclosure 1,4-BDO samples obtained from the distillate of the fourth distillation column of a four column distillation system has a UV absorbance at 270 nm (UV270 absorbance) of less than 0.20, 0.12, 0.11, 0.10, 0.09, 0.08 or 0.05 absorbance units. In some embodiments, 1,4-BDO samples obtained from the distillate of the second distillation column of a four column distillation system has a UV270 absorbance of more than 1.0, 2.0, 3.0 or 4.0. In some embodiments, 1,4-BDO samples obtained from the distillate of the second column of a four column distillation system have at least 10-fold, 20-fold, 30-fold, 40-fold, 50-fold, 60-fold, 70-fold, 80-fold, 90-fold or 100-fold higher UV270 absorbance than 1,4-BDO samples of obtained from the distillate of the fourth column of a four column distillation.

In the systems and processes provided herein that include distillation columns, there can be a column (termed "heavies column") in which a 1,4-BDO product stream is removed in a distillate or a side-draw, while the bottoms purge stream (high boilers) is disposed of (or, as explained above, subjected to a wiped film evaporation and/or a reboiler). The bottoms purge stream from a heavies column typically contains amino acids, salts, sugars, etc., that may foul later processing units (e.g., a hydrogenation unit). In certain embodiments, the second column in a two-column system is a heavies column. In certain embodiments, the first intermediate column in a three or four-column system is a heavies column. The feed rate, bottoms purge rate, and ratio of purge rate to feed rate of the heavies column can, for example, be within the parameters explained below.

In some embodiments, the purge rate of the heavies column is between about 0.04 kg/hr and about 1,000 kg/hr. For instance, the purge can be between about 0.04 kg/hr and 2.0 kg/hr; between about 30 kg/hr to 130 kg/hr; or between about 200 kg/hr to 1,000. kg/hr. In some embodiments, the purge rate is 0.8 kg/hr. In some embodiments, the purge rate is between about 0.8 kg/hr and 245 kg/hr; between about 0.8 kg/hr and 490 kg/hr; between about 0.8 kg/hr and 620 kg/hr; or between 0.8 kg/hr and 1,000 kg/hr.

In some embodiments, the feed rate of the heavies column is between about 5.0 kg/hr to about 10,000 kg/hr. For example, the feed rate can be between about 5.0 kg/hr to about 13 kg/hr; between about 1,475 kg/hr to 2,500 kg/hr; about 2,500 kg/hr to 5,000 kg/hr; or about 5,000 kg/hr to 10,000 kg/hr.

In some embodiments, the ratio between the purge rate and the feed rate of a heavies column is between about 0.003 to about 0.30, about 0.03 to about 2.0, or about 0.07 to about 0.154. In certain embodiments, the ratio between the purge rate and the feed rate of the heavies column is about 0.1.

While the process and systems described herein are, in certain instances, discussed with respect to obtaining 1,4-BDO, in separate embodiments the process and systems described herein can be employed for the purification of other compounds of interest, where such compounds are present in a fermentation broth, are water miscible, and have a boiling point higher than that for water. Such compounds of interest include, for example, 1,3-butanediol (1,3-BDO), 2,3-butanediol (2,3-BDO), 1,3-propanediol (1,3-PDO), 1,2-propanediol (1,2-PDO methyl ethyl glycol), 1,2-ethanediol (ethylene glycol), gamma-butyrolactone (GBL), 1,5-pentanediol, 1,6-hexanediol.

Applications

The purity of 1,4-BDO product can reflect the application for which the 1,4-BDO is to be used. For example, 1,4-BDO for use in brown plastic, poly(butylene adipate-co-terephthalates or to produce THF can be able to have more colored impurities than a 1,4-BDO product that will be used in clear plastic, for example, in many polyurethane or copolyester ethers products, which can require a nearly colorless 1,4-BDO product. Accordingly, the 1,4-BDO product useful for brown or other colored plastic products can not need as many purification steps as a 1,4-BDO product for another application, such as clear plastic products or polymer. The purity of the 1,4-BDO product can be selected to be a crude 1,4-BDO mixture of at least 80% or 85%, or can be a purified 1,4-BDO product of at least 90%, 91%, 92%, 93%, 94%, 95%, 96%, 96%, 97%, 98%, 99%, 99.1%, 99.2%, 99.3%, 99.4%, 99.5%, 99.6%, 99.7%, 99.8% or 99.9%, on a weight/weight basis, and depending the desired 1,4-BDO end product. The color of the 1,4-BDO product can have an APHA color less than 10, 20, 30, 40, 50, 60, 70, 80, 90 or 100. The 1,4-BDO product can have an absorbance at 270 nm of less than 0.01, 0.05, 0.1, 0.2, 0.3, 0.4, 0.5, 0.6, 0.8, 1.0, 2.0, 5, 10.0 or 20.0.

The 1,4-BDO product produced as described herein can, for example, be free or have low amounts of certain compounds, such as those described in Table I below. In certain embodiments, the 1,4-BDO product can, for example, be greater than 99% 1,4-BDO, can have no or less than 0.01 percent 2-methyl-3-buten-1-ol, and/or no or less than 0.01 percent 1,6-hexanediol, and/or less than 0.04 percent butanoic acid, propyl ester and/or less than 0.04 percent 2-(4-hydroxybutoxy) tetrahydrofuran.

TABLE i

Analysis of 1,4-BDO product

| Compound | Structure | Amount |
|---|---|---|
| 1,4-butanediol | 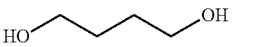 | 99.95 |
| 2-methyl-3-buten-1-ol | 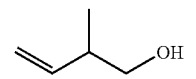 | <0.1 |
| 1,4-butanediol, monoacetate | 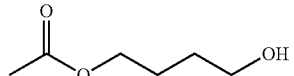 | <0.01 |
| 1,6-hexanediol | 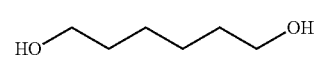 | <0.04 |

1,4-BDO is a valuable chemical for the production of high performance solvent, fine chemicals, cosmetics, personal care products and polymers, including plastics, elastic fibers, polyurethanes, and polyesters. It is the basis for producing other high value chemicals including tetrahydrofuran (THF) and gamma-butyrolactone (GBL). In the case of polymers, 1,4-BDO is a co-monomer for polybutylene terephthalate (PBT) production. PBT is a medium performance engineering thermoplastic used in automotive, electrical, water systems, and small appliance applications. 1,4-BDO is a co-monomer for polyurethane and polyurethane-polyurea copolymers. 1,4-BDO is a co-monomer for biodegradable polymers, including PBAT (poly(butylene adipate-co-terephthalate)) and PBS (poly(butylene succinate)). Conversion of 1,4-BDO to THF, and subsequently to polytetramethylene ether glycol (PTMEG) (also referred to as PTMO, polytetramethylene oxide and PTHF, poly(tetrahydrofuran)), provides an intermediate used to manufacture elastic fibers, e.g. spandex fiber, used in products such as LYCRA® fibers or elastane, for example when combined with polyurethane-polyurea copolymers. THF also finds use as an industrial solvent and in pharmaceutical production. PTMEG is also combined with in the production of specialty thermoplastic elastomers (TPE), including thermoplastic elastomer polyester (TPE-E or TPEE) and copolyester ethers (COPE). COPEs are high modulus elastomers with excellent mechanical properties and oil/environmental resistance, allowing them to operate at high and low temperature extremes. PTMEG and 1,4-BDO also make thermoplastic polyurethanes (e.g. TPE-U or TPEU) processed on standard thermoplastic extrusion, calendaring, and molding equipment, and are characterized by their outstanding toughness and abrasion resistance. The GBL produced from 1,4-BDO finds uses including in solvents, paint stripper and glue removers, and as a pharmaceutical and in making pharmaceuticals. The GBL produced from 1,4-BDO provides the feedstock for making pyrrolidones, including N-methyl-2-pyrrolidone (NMP) and 2-pyrrolidone, which in turn is used to produce N-vinyl-2-pyrrolidone (NVP) and polyvinyl pyrrolidone (PVP), as well as serving the agrochemical market. The pyrrolidones are used as high performance solvents for extraction processes of increasing use, including for example, in the electronics industry and in pharmaceutical production. NMP use and compositions include a coating, an extractant for processing or recovering industrial chemicals and an excipient for formulation of pharmaceuticals, cosmetics and personal care products. PP finds use as an industrial solvent and in the production of NVP and PVP. PVP use and compositions include a coating, an excipient in pharmaceutical formulations, cosmetics and personal care products, a solvent or solubility enhancer, and a thickening agent. NVP use and compositions include a UV protectant and viscosity enhancer. Accordingly, provided herein is bioderived 1,4-BDO produced according to the methods described herein and biobased products comprising or obtained using the bioderived 1,4-BDO.

The biobased product can comprise 1,4-BDO, a polymer, THF or a THF derivative, or GBL or a GBL derivative; or the biobased product can comprise 1,4-BDO, a polymer, a plastic, elastic fiber, polyurethane, polyester, polyhydroxyalkanoate, poly-4-hydroxybutyrate, co-polymer of poly-4-hydroxybutyrate, poly(tetramethylene ether) glycol, polyurethane, polyurethane-polyurea copolymer, spandex, elastane, LYCRA®, nylon or a biodegradable plastic including PBAT and PBS; or the biobased product can comprise polybutylene terephthalate (PBT) polymer; or the biobased product can comprise a PBT, PBAT, PBS, or PU polymer, and preferably a PBT polymer, that comprises a resin, a fiber, a bead, a granule, a pellet, a chip, a plastic, a polyester, a thermoplastic polyester, a molded article, an injection-molded article, an injection-molded part, an automotive part, an extrusion resin, an electrical part and a casing, optionally where the biobased product is reinforced or filled, for example glass-filled or mineral-filled; or the biobased product is THF or a THF derivative, and the THF can be an industrial solvent and used in pharmaceutical production, and the THF derivative can be polytetramethylene ether glycol (PTMEG), a polyester ether (COPE), a thermoplastic polyurethane, a fiber, an elastic fiber, a thermoplastic elastomer, a spandex fiber, or a thermoplastic elastomer polyester; or the biobased product comprises GBL or a GBL derivative. The GBL comprising composition includes a solvent, a paint stripper, a glue remover, or a pharmaceutical, and also where the GBL derivative is a pyrrolidone, including N-methyl-2-pyrrolidone (NMP), 2-pyrrolidone, N-vinyl-2-pyrrolidone (NVP) and polyvinyl pyrrolidone (PVP). The pyrrolidone can be used as high performance solvent, as a high performance solvent for chemical extraction, and as pharmaceutical excipient or in pharmaceutical production; the NMP comprising compositions and uses include NMP as a coating, an extractant for processing or recovering industrial chemicals and an excipient for formulation of pharmaceuticals, cosmetics and personal care products; PP comprising compositions and uses include PP as an industrial solvent and production of NVP and PVP; PVP compositions and uses include PVP as a coating, an excipient in pharmaceutical formulations, cosmetics and personal care products, a solvent or solubility enhancer and a thickening agent; and NVP comprising compositions and uses include NVP as a UV protectant and viscosity enhancer.

The biobased product can comprise at least 5%, at least 10%, at least 20%, at least 30%, at least 40% or at least 50% bioderived 1,4-BDO. The biobased product can comprise a portion of said bioderived 1,4-BDO as a repeating unit. The biobased product can be a molded product obtained by molding the biobased product. In certain embodiments, the biobased product comprises at least 5% or at least 10% bioderived 1,4-BDO. In some embodiments, the biobased product comprises at least 20% bioderived 1,4-BDO. In other embodiments, the biobased product comprises at least 30% bioderived 1,4-BDO. In some embodiments, the biobased product comprises at least 40% bioderived 1,4-BDO. In other embodiments, the biobased product comprises at least 50% bioderived 1,4-BDO. In one embodiment, the biobased product comprises a portion of said bioderived 1,4-BDO as a repeating unit. In another embodiment, provided herein is a molded product obtained by molding the biobased product provided herein. In other embodiments, provided herein is a process for producing a biobased product provided herein, comprising chemically reacting said bioderived 1,4-BDO with itself or another compound in a reaction that produces said biobased product. In certain embodiments, provided herein is a polymer comprising or obtained by converting the bioderived 1,4-BDO. In other embodiments, provided herein is a method for producing a polymer, comprising chemically of enzymatically converting the bioderived 1,4-BDO to the polymer. In yet other embodiments, provided herein is a composition comprising the bioderived 1,4-BDO, or a cell lysate or culture supernatant thereof.

For example, a biobased 1,4-BDO, a polymer, THF or a THF derivative, or GBL or a GBL derivative; or the biobased product can comprise 1,4-BDO, a polymer, a plastic, elastic fiber, polyurethane, polyester, polyhydroxyalkanoate, poly-4-hydroxybutyrate, co-polymer of poly-4-hydroxybutyrate, poly(tetramethylene ether) glycol, polyurethane, polyurethane-polyurea copolymer, spandex, elastane, LYCRA®, nylon or a biodegradable plastic including PBAT and PBS; or the biobased product can comprise polybutylene terephthalate (PBT) polymer; or the biobased product can comprise a PBT, PBAT, PBS, or PU polymer, and a PBT polymer, that comprises a resin, a fiber, a bead, a granule, a pellet, a chip, a plastic, a polyester, a thermoplastic polyester, a molded article, an injection-molded article, an injection-molded part, an automotive part, an extrusion resin, an electrical part and a casing, optionally where the biobased product is reinforced or filled, for example glass-filled or mineral-filled; or the biobased product is THF or a THF derivative, and the THF can be an industrial solvent and used in pharmaceutical production, and the THF derivative can be polytetramethylene ether glycol (PTMEG), a polyester ether (COPE), a thermoplastic polyurethane, a fiber, an elastic fiber, a thermoplastic elastomer, a spandex fiber, or a thermoplastic elastomer polyester; or the biobased product comprises GBL or a GBL derivative, where the GBL comprising composition includes a solvent, a paint stripper, a glue remover, or a pharmaceutical, and also where the GBL derivative is a pyrrolidone, including N-methyl-2-pyrrolidone (NMP), 2-pyrrolidone, N-vinyl-2-pyrrolidone (NVP) and polyvinyl pyrrolidone (PVP), and the pyrrolidone can be used as high performance solvent, as a high performance solvent for chemical extraction, and as pharmaceutical excipient or in pharmaceutical production; the NMP comprising compositions and uses include NMP as a coating, an extractant for processing or recovering industrial chemicals and an excipient for formulation of pharmaceuticals, cosmetics and personal care products; PP comprising compositions and uses include PP as an industrial solvent and production of NVP and PVP; PVP compositions and uses include PVP as a coating, an excipient in pharmaceutical formulations, cosmetics and personal care products, a solvent or solubility enhancer and a thickening agent; and NVP comprising compositions and uses include NVP as a UV protectant and viscosity enhancer can be produced using 50% bioderived 1,4-BDO and 50% petroleum derived 1,4-BDO or other desired ratios such as 60%/40%, 70%/30%, 80%/20%, 90%/10%, 95%/5%, 100%/0%, 40%/60%, 30%/70%, 20%/80%, 10%/90% of bioderived/petroleum derived precursors, so long as at least a portion of the product comprises a bioderived product produced by the microbial organisms disclosed herein. It is understood that methods for producing 1,4-BDO, a polymer, THF or a THF derivative, or GBL or a GBL derivative; or the biobased product can comprise 1,4-BDO, a polymer, a plastic, elastic fiber, polyurethane, polyester, polyhydroxyalkanoate, poly-4-hydroxybutyrate, co-polymer of poly-4-hydroxybutyrate, poly(tetramethylene ether) glycol, polyurethane, polyurethane-polyurea copolymer, spandex, elastane, LYCRA®, nylon or a biodegradable plastic including PBAT and PBS; or the biobased product can comprise polybutylene terephthalate (PBT) polymer; or the biobased product can comprise a PBT, PBAT, PBS, or PU polymer, and a PBT polymer, that comprises a resin, a fiber, a bead, a granule, a pellet, a chip, a plastic, a polyester, a thermoplastic polyester, a molded article, an injection-molded article, an injection-molded part, an automotive part, an extrusion resin, an electrical part and a casing, optionally where the biobased product is reinforced or filled, for example glass-filled or mineral-filled; or the biobased product is THF or a THF derivative, and the THF can be an industrial solvent and used in pharmaceutical production, and the THF derivative can be polytetramethylene ether glycol (PTMEG), a polyester ether (COPE), a thermoplastic polyurethane, a fiber, an elastic fiber, a thermoplastic elastomer, a spandex fiber, or a thermoplastic elastomer polyester; or the biobased product comprises GBL or a GBL derivative, where the GBL comprising composition includes a solvent, a paint stripper, a glue remover, or a pharmaceutical, and also where the GBL derivative is a pyrrolidone, including N-methyl-2-pyrrolidone (NMP), 2-pyrrolidone, N-vinyl-2-pyrrolidone (NVP) and polyvinyl pyrrolidone (PVP), and the pyrrolidone can be used as high performance solvent, as a high performance solvent for chemical extraction, and as pharmaceutical excipient or in pharmaceutical production; the NMP comprising compositions and uses include NMP as a coating, an extractant for processing or recovering industrial chemicals and an excipient for formulation of pharmaceuticals, cosmetics and personal care products; PP comprising compositions and uses include PP as an industrial solvent and production of NVP and PVP; PVP compositions and uses include PVP as a coating, an excipient in pharmaceutical formulations, cosmetics and personal care products, a solvent or solubility enhancer and a thickening agent; and NVP comprising compositions and uses include NVP as a UV protectant and viscosity enhancer using the bioderived 1,4-BDO or bioderived 1,4-BDO pathway intermediate of the invention are well known in the art.

Bioderived 1,4-BDO or target compound has a carbon-12, carbon-13 and carbon-14 isotope ratio that reflects an atmospheric carbon dioxide source, wherein the bioderived 1,4-BDO or target compound is produced by the any of the embodiments of the present disclosure. Renewable carbon sources can have a carbon-12, carbon-13 and carbon-14 isotope ratio that reflects an atmospheric carbon dioxide source. Other sources of carbon, not from renewable resources can have carbon-12, carbon-13 and carbon-14 isotope ratio that does not reflects an atmospheric carbon dioxide source In some embodiments, the carbon feedstock and other cellular uptake sources such as phosphate, ammonia, sulfate, chloride and other halogens can be chosen to alter the isotopic distribution of the atoms present in 1,4-BDO or any 1,4-BDO pathway intermediate. The various carbon feedstock and other uptake sources enumerated above will be referred to herein, collectively, as "uptake sources." Uptake sources can provide isotopic enrichment for any atom present in the product 1,4-BDO or 1,4-BDO pathway intermediate, or for side products generated in reactions diverging away from a 1,4-BDO pathway. Isotopic enrichment can be achieved for any target atom including, for example, carbon, hydrogen, oxygen, nitrogen, sulfur, phosphorus, chloride or other halogens.

In some embodiments, the uptake sources can be selected to alter the carbon-12, carbon-13, and carbon-14 ratios. In some embodiments, the uptake sources can be selected to alter the oxygen-16, oxygen-17, and oxygen-18 ratios. In some embodiments, the uptake sources can be selected to alter the hydrogen, deuterium, and tritium ratios. In some embodiments, the uptake sources can be selected to alter the nitrogen-14 and nitrogen-15 ratios. In some embodiments, the uptake sources can be selected to alter the sulfur-32, sulfur-33, sulfur-34, and sulfur-35 ratios. In some embodiments, the uptake sources can be selected to alter the phosphorus-31, phosphorus-32, and phosphorus-33 ratios. In some embodiments, the uptake sources can be selected to alter the chlorine-35, chlorine-36, and chlorine-37 ratios.

In some embodiments, the isotopic ratio of a target atom can be varied to a desired ratio by selecting one or more uptake sources. An uptake source can be derived from a natural source, as found in nature, or from a man-made source, and one skilled in the art can select a natural source, a man-made source, or a combination thereof, to achieve a desired isotopic ratio of a target atom. An example of a man-made uptake source includes, for example, an uptake source that is at least partially derived from a chemical synthetic reaction. Such isotopically enriched uptake sources can be purchased commercially or prepared in the laboratory and/or optionally mixed with a natural source of the uptake source to achieve a desired isotopic ratio. In some embodiments, a target atom isotopic ratio of an uptake source can be achieved by selecting a desired origin of the uptake source as found in nature. For example, as discussed herein, a natural source can be a biobased derived from or synthesized by a biological organism or a source such as petroleum-based products or the atmosphere. In some such embodiments, a source of carbon, for example, can be selected from a fossil fuel-derived carbon source, which can be relatively depleted of carbon-14, or an environmental or atmospheric carbon source, such as $CO_2$, which can possess a larger amount of carbon-14 than its petroleum-derived counterpart.

The unstable carbon isotope carbon-14 or radiocarbon makes up for roughly 1 in 1012 carbon atoms in the earth's atmosphere and has a half-life of about 5700 years. The stock of carbon is replenished in the upper atmosphere by a nuclear reaction involving cosmic rays and ordinary nitrogen ($^{14}N$). Fossil fuels contain no carbon-14, as it decayed long ago. Burning of fossil fuels lowers the atmospheric carbon-14 fraction, the so-called "Suess effect".

Methods of determining the isotopic ratios of atoms in a compound are well known to those skilled in the art. Isotopic enrichment is readily assessed by mass spectrometry using techniques known in the art such as accelerated mass spectrometry (AMS), Stable Isotope Ratio Mass Spectrometry (SIRMS) and Site-Specific Natural Isotopic Fractionation by Nuclear Magnetic Resonance (SNIF-NMR). Such mass spectral techniques can be integrated with separation techniques such as liquid chromatography (LC), high performance liquid chromatography (HPLC) and/or gas chromatography, and the like.

In the case of carbon, ASTM D6866 was developed in the United States as a standardized analytical method for determining the biobased content of solid, liquid, and gaseous samples using radiocarbon dating by the American Society for Testing and Materials (ASTM) International. The standard is based on the use of radiocarbon dating for the determination of a product's biobased content. ASTM D6866 was first published in 2004, and the current active version of the standard is ASTM D6866-11 (effective Apr. 1, 2011). Radiocarbon dating techniques are well known to those skilled in the art, including those described herein.

The biobased content of a compound is estimated by the ratio of carbon-14 ($^{14}C$) to carbon-12 ($^{12}C$). Specifically, the Fraction Modern (Fm) is computed from the expression: Fm=(S−B)/(M−B), where B, S and M represent the $^{14}C/^{12}C$ ratios of the blank, the sample and the modern reference, respectively. Fraction Modern is a measurement of the deviation of the $^{14}C/^{12}C$ ratio of a sample from "Modern." Modern is defined as 95% of the radiocarbon concentration (in AD 1950) of National Bureau of Standards (NBS) Oxalic Acid I (i.e., standard reference materials (SRM) 4990b) normalized to δ13CVPDB=−19 per mil (Olsson, The use of Oxalic acid as a Standard. in, Radiocarbon Variations and Absolute Chronology, Nobel Symposium, 12th Proc., John Wiley & Sons, New York (1970)). Mass spectrometry results, for example, measured by ASM, are calculated using the internationally agreed upon definition of 0.95 times the specific activity of NBS Oxalic Acid I (SRM 4990b) normalized to δ13CVPDB=−19 per mil. This is equivalent to an absolute (AD 1950) 14C/12C ratio of 1.176±0.010×10−12 (Karlen et al., Arkiv Geofysik, 4:465-471 (1968)). The standard calculations take into account the differential uptake of one isotope with respect to another, for example, the preferential uptake in biological systems of $^{12}C$ over $^{13}C$ over $^{14}C$, and these corrections are reflected as a Fm corrected for δ13.

An oxalic acid standard (SRM 4990b or HOx 1) was made from a crop of 1955 sugar beet. Although there were 1000 lbs made, this oxalic acid standard is no longer commercially available. The Oxalic Acid II standard (HOx 2; N.I.S.T designation SRM 4990 C) was made from a crop of 1977 French beet molasses. In the early 1980's, a group of 12 laboratories measured the ratios of the two standards. The ratio of the activity of Oxalic acid II to 1 is 1.2933±0.001 (the weighted mean). The isotopic ratio of HOx II is −17.8 per mille. ASTM D6866-11 suggests use of the available Oxalic Acid II standard SRM 4990 C (Hox2) for the modern standard (see discussion of original vs. currently available oxalic acid standards in Mann, Radiocarbon, 25(2):519-527 (1983)). A Fm=0% represents the entire lack of carbon-14 atoms in a material, thus indicating a fossil (for example, petroleum based) carbon source. A Fm=100%, after correction for the post-1950 injection of carbon-14 into the atmosphere from nuclear bomb testing, indicates an entirely modern carbon source. As described herein, such a "modern" source includes biobased sources.

As described in ASTM D6866, the percent modern carbon (pMC) can be greater than 100% because of the continuing but diminishing effects of the 1950s nuclear testing programs, which resulted in a considerable enrichment of carbon-14 in the atmosphere as described in ASTM D6866-11. Because all sample carbon-14 activities are referenced to a "pre-bomb" standard, and because nearly all new biobased products are produced in a post-bomb environment, all pMC values (after correction for isotopic fraction) must be multiplied by 0.95 (as of 2010) to better reflect the true biobased content of the sample. A biobased content that is greater than 103% suggests that either an analytical error has occurred, or that the source of biobased carbon is more than several years old.

ASTM D6866 quantifies the biobased content relative to the material's total organic content and does not consider the inorganic carbon and other non-carbon containing substances present. For example, a product that is 50% starch-based material and 50% water would be considered to have a Biobased Content=100% (50% organic content that is 100% biobased) based on ASTM D6866. In another example, a product that is 50% starch-based material, 25% petroleum-based, and 25% water would have a Biobased Content=66.7% (75% organic content but only 50% of the product is biobased). In another example, a product that is 50% organic carbon and is a petroleum-based product would be considered to have a Biobased Content=0% (50% organic carbon but from fossil sources). Thus, based on the well known methods and known standards for determining the biobased content of a compound or material, one skilled in the art can readily determine the biobased content and/or prepared downstream products that utilize of the invention having a desired biobased content.

Applications of carbon-14 dating techniques to quantify bio-based content of materials are known in the art (Currie et al., Nuclear Instruments and Methods in Physics Research B, 172:281-287 (2000)). For example, carbon-14 dating has been used to quantify bio-based content in terephthalate-containing materials (Colonna et al., Green Chemistry, 13:2543-2548 (2011)). Notably, polypropylene terephthalate (PPT) polymers derived from renewable 1,3-propanediol and petroleum-derived terephthalic acid resulted in Fm values near 30% (i.e., since 3/11 of the polymeric carbon derives from renewable 1,3-propanediol and 8/11 from the fossil end member terephthalic acid) (Currie et al., supra, 2000). In contrast, polybutylene terephthalate polymer derived from both renewable 1,4-butanediol and renewable terephthalic acid resulted in bio-based content exceeding 90% (Colonna et al., supra, 2011).

Accordingly, in some embodiments, the present invention provides 1,4-BDO or a 1,4-BDO pathway intermediate that has a carbon-12, carbon-13, and carbon-14 ratio that reflects an atmospheric carbon, also referred to as environmental carbon, uptake source. For example, in some aspects the 1,4-BDO or a 1,4-BDO pathway intermediate can have an Fm value of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98% or as much as 100%. In some embodiments, the uptake source is $CO_2$. In some embodiments, the present invention provides 1,4-BDO or a 1,4-BDO pathway intermediate that has a carbon-12, carbon-13, and carbon-14 ratio that reflects petroleum-based carbon uptake source. In this aspect, the 1,4-BDO or a 1,4-BDO pathway intermediate can have an Fm value of less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, less than 5%, less than 2% or less than 1%. In some embodiments, the present invention provides 1,4-BDO or a 1,4-BDO pathway intermediate that has a carbon-12, carbon-13, and carbon-14 ratio that is obtained by a combination of an atmospheric carbon uptake source with a petroleum-based uptake source. Using such a combination of uptake sources is one way by which the carbon-12, carbon-13, and carbon-14 ratio can be varied, and the respective ratios would reflect the proportions of the uptake sources.

Further, the present invention relates to the biologically produced 1,4-BDO or 1,4-BDO pathway intermediate as disclosed herein, and to the products derived therefrom, wherein the 1,4-BDO or a 1,4-BDO pathway intermediate has a carbon-12, carbon-13, and carbon-14 isotope ratio of about the same value as the CO2 that occurs in the environment. For example, in some aspects the invention provides bioderived 1,4-BDO or a bioderived 1,4-BDO intermediate having a carbon-12 versus carbon-13 versus carbon-14 isotope ratio of about the same value as the $CO_2$ that occurs in the environment, or any of the other ratios disclosed herein. It is understood, as disclosed herein, that a product can have a carbon-12 versus carbon-13 versus carbon-14 isotope ratio of about the same value as the $CO_2$ that occurs in the environment, or any of the ratios disclosed herein, wherein the product is generated from bioderived 1,4-BDO or a bioderived 1,4-BDO pathway intermediate as disclosed herein, wherein the bioderived product is chemically modified to generate a final product. Methods of chemically modifying a bioderived product of 1,4-BDO, or an intermediate thereof, to generate a desired product are well known to those skilled in the art, as described herein. The invention further provides 1,4-BDO, a polymer, THF or a THF derivative, or GBL or a GBL derivative; or the biobased product can comprise 1,4-BDO, a polymer, a plastic, elastic fiber, polyurethane, polyester, polyhydroxyalkanoate, poly-4-hydroxybutyrate, co-polymer of poly-4-hydroxybutyrate, poly(tetramethylene ether) glycol, polyurethane, polyurethane-polyurea copolymer, spandex, elastane, LYCRA®, nylon or a biodegradable plastic including PBAT and PBS; or the biobased product can comprise polybutylene terephthalate (PBT) polymer; or the biobased product can comprise a PBT, PBAT, PBS, or PU polymer, and a PBT polymer, that comprises a resin, a fiber, a bead, a granule, a pellet, a chip, a plastic, a polyester, a thermoplastic polyester, a molded article, an injection-molded article, an injection-molded part, an automotive part, an extrusion resin, an electrical part and a casing, optionally where the biobased product is reinforced or filled, for example glass-filled or mineral-filled; or the biobased product is THF or a THF derivative, and the THF can be an industrial solvent and used in pharmaceutical production, and the THF derivative can be polytetramethylene ether glycol (PTMEG), a polyester ether (COPE), a thermoplastic polyurethane, a fiber, an elastic fiber, a thermoplastic elastomer, a spandex fiber, or a thermoplastic elastomer polyester; or the biobased product comprises GBL or a GBL derivative, where the GBL comprising composition includes a solvent, a paint stripper, a glue remover, or a pharmaceutical, and also where the GBL derivative is a pyrrolidone, including N-methyl-2-pyrrolidone (NMP), 2-pyrrolidone, N-vinyl-2-pyrrolidone (NVP) and polyvinyl pyrrolidone (PVP), and the pyrrolidone can be used as high performance solvent, as a high performance solvent for chemical extraction, and as pharmaceutical excipient or in pharmaceutical production; the NMP comprising compositions and uses include NMP as a coating, an extractant for processing or recovering industrial chemicals and an excipient for formulation of pharmaceuticals, cosmetics and personal care products; PP comprising compositions and uses include PP as an industrial solvent and production of NVP and PVP; PVP compositions and uses include PVP as a coating, an excipient in pharmaceutical formulations, cosmetics and personal care products, a solvent or solubility enhancer and a thickening agent; and NVP comprising compositions and uses include NVP as a UV protectant and viscosity enhancer having a carbon-12 versus carbon-13 versus carbon-14 isotope ratio of about the same value as the $CO_2$ that occurs in the environment, wherein the 1,4-BDO, a polymer, THF or a THF derivative, or GBL or a GBL derivative; or the biobased product can comprise 1,4-BDO, a polymer, a plastic, elastic fiber, polyurethane, polyester, polyhydroxyalkanoate, poly-4-hydroxybutyrate, co-polymer of poly-4-hydroxybutyrate, poly(tetramethylene ether) glycol, polyurethane, polyurethane-polyurea copolymer, spandex, elastane, LYCRA®, nylon or a biodegradable plastic including PBAT and PBS; or the biobased product can comprise polybutylene terephthalate (PBT) polymer; or the biobased product can comprise a PBT, PBAT, PBS, or PU polymer, and a PBT polymer, that comprises a resin, a fiber, a bead, a granule, a pellet, a chip, a plastic, a polyester, a thermoplastic polyester, a molded article, an injection-molded article, an injection-molded part, an automotive part, an extrusion resin, an electrical part and a casing, optionally where the biobased product is reinforced or filled, for example glass-filled or mineral-filled; or the biobased product is THF or a THF derivative, and the THF can be an industrial solvent and used in pharmaceutical production, and the THF derivative can be polytetramethylene ether glycol (PTMEG), a polyester ether (COPE), a thermoplastic polyurethane, a fiber, an elastic fiber, a thermoplastic elastomer, a spandex fiber, or a thermoplastic elastomer polyester; or the biobased product comprises GBL or a GBL derivative, where the GBL comprising composition includes a solvent, a paint stripper, a glue remover, or a pharmaceutical, and also where the GBL derivative is a pyrrolidone, including N-methyl-2-pyrrolidone (NMP), 2-pyrrolidone, N-vinyl-2-pyrrolidone (NVP) and polyvinyl pyrrolidone (PVP), and the pyrrolidone can be used as high performance solvent, as a high performance solvent for chemical extraction, and as pharmaceutical excipient or in pharmaceutical production; the NMP comprising compositions and uses include NMP as a coating, an extractant for processing or recovering industrial chemicals and an excipient for formulation of pharmaceuticals, cosmetics and personal care products; PP comprising compositions and uses include PP as an industrial solvent and production of NVP and PVP; PVP compositions and uses include PVP as a coating, an excipient in pharmaceutical formulations, cosmetics and personal care products, a solvent or solubility enhancer and a thickening agent; and NVP comprising compositions and uses include NVP as a UV protectant and viscosity enhancer are generated directly from or in combination with bioderived 1,4-BDO or a bioderived 1,4-BDO pathway intermediate as disclosed herein.

Example 1

Filtration with and without an Ultrafiltration Procedure

A procedure was carried out to determine the effect of ultrafiltration in a series of filtrations that included an ultrafiltration or bypassed the ultrafiltration between microfiltration and nanofiltration. A modified non-naturally occurring organism was cultured to produce a 1,4-BDO in a fermentation broth. The fermentation broth was subjected to microfiltration with a ceramic membrane of 0.05 micron pore size. A portion of the filtrate of the microfiltration step was then subjected to ultrafiltration utilizing an ultrafiltration membrane of 5000 Daltons MWCO. The filtrate of the ultrafiltration was then subjected to nanofiltration using a nanofiltration membrane with about a 200 Daltons MWCO. Another portion of the filtrate of the microfiltration step that was not subjected to ultrafiltration, was subjected to the same nanofiltration procedure. The filtration membranes were routinely cleaned throughout the processing of the fermentation broth. The rate at which clean water passes through the membrane after cleaning was recorded, and calculated as a percent of the rate expected when the membrane is new and is called the clean water flux (CWF). The experiment was repeated but using a polymeric microfiltration membrane with a MWCO of 20,000 Dalton in place of the ceramic microfiltration membrane. Results of the performance of the nanofiltration after microfiltration with and without ultrafiltration demonstrate that the nanofiltration can be successfully performed on a microfiltration filtrate without an intervening ultrafiltration step, and it was discovered that surprisingly, there was not a significant loss of process efficiency from nanofiltration membrane fouling or flux rate as evidenced by the clean water flux measurements.

TABLE 1

Results of the effect of ultrafiltration on subsequent nanofiltration.

| Filtration steps before nanofiltration | No. of Batches processed | Clean Water Flux of Nanofiltration Membrane |
| --- | --- | --- |
| Ceramic Microfiltration Ultrafiltration | 10 | 86% |
| Ceramic Microfiltration | 13 | 77% |
| Polymeric Microfiltration Ultrafiltration | 30 | 94% |
| Polymeric Microfiltration | 6 | 88% |

Example 2

Polishing Ion Exchange Step with Only an Anion Exchange Resin

This example demonstrates that polishing anion exchange removes undesirable components from a 1,4-BDO containing mixture, whereas little or no effect was observed with polishing cation exchange. A modified non-naturally occurring organism was cultured to produce a 1,4-BDO in a fermentation broth. The fermentation broth was subjected to filtration and evaporation to give a crude 1,4-BDO mixture that was approximately 80% 1,4-BDO/20% water, which was used in these experiments. The resins used were DOWEX™ 22 strong base anion exchange resin and DOWEX™ MS 88 strongly acidic cation exchange resin. All resins were freshly regenerated by usually procedures before use. The crude 1,4-BDO mixture was treated isothermally with various resins and the UV absorbance at 270 nm was monitored. Results were determined by measuring the UV absorbance at 270 nm in the 1,4-BDO product after treatment with the ion exchange resins, which gives a measure of the amount of certain species removed by the ion exchange.

It was found that treatment with strong base anion exchange produced similar results to mixed cation-anion exchange, both removing a majority of the species as indicated by the decrease in absorbance at 270 nm. Cation exchange did not remove any of the monitored species (see Table 2). The results indicate that anion exchange resin in the absence of cation exchange resin can remove a majority of the undesirable species absorbing at 270 nm from 1,4-BDO in a crude 1,4-BDO mixture.

TABLE 2

Results of treating a crude 1,4-BDO
mixture with Ion Exchange.

| Treatment | UV 270 Absorbance |
|---|---|
| None | 39.5 |
| Anion Exchange | 5.2 |
| Cation Exchange | 41.9 |
| Mixed Bed | 4.5 |

Examples 3-6

Two Distillation Column System

The following examples describe 2-column distillation systems simulating a 2-column system with a product from a side-draw of the second column to produce a purified 1,4-BDO product.

A demonstration distillation was carried out using available distillation equipment which consisted of 3 columns and associated hardware such as reboilers, condensers and vacuum system. A number of options were evaluated to best approximate the operation of a side-draw to recover product. ASPEN PLUS® simulation program was used to model the two column system with side draw using a three column configuration, and predict the best layout and operating parameters for producing a purified 1,4-BDO product.

Three columns were used to simulate the side draw product option. The vapor side-draw was simulated by using the third demonstration column. The distillate from the top of the second demonstration column was fed into the base of the third column. The bottom of the third column represented the purified 1,4 BDO product. In the demonstration distillation, the product was a liquid that represented a condensed vapor side draw stream.

A modified non-naturally occurring organism was cultured to produce 1,4-BDO in a fermentation broth. The fermentation broth was passed through three filtrations: microfiltration followed by ultrafiltration and finally nanofiltration to produce a separated 1,4-BDO product. The separated 1,4-BDO product was then subjected to ion-exchange (strongly acidic cation and weakly basic anion exchange resins) to remove salts, followed by evaporation to remove water, and then subjected to a polishing ion-exchange (mixed cation-anion exchange) to produce the crude 1,4-BDO mixture. This crude 1,4-BDO mixture was used in Examples 3-6.

Example 3

In the demonstration distillation a first distillation column with 10 stages was set up to receive as feed the crude 1,4-BDO mixture at stage 6. In some experiments, distillation columns with 8 to 14 stages were used. The feed rate of 8 liters/hr was used during the distillation. The column was operated at a top pressure of 80 mmHg, with a base temperature of 170° C., and a molar reflux ratio of 1 to 1.75. Water and light materials (material with boiling points lower than 1,4-BDO) were removed from the crude 1,4-BDO mixture from the top of the column. A 1,4-BDO-containing product stream was removed from the bottom of the column.

A second distillation column with 18 stages was set up to receive at stage 11 as feed, the 1,4-BDO-containing product stream that was obtained from the bottom of the first column. The column was operated at 25 mmHg with a base temperature of 160° C., and a molar reflux ratio of 1.25. Materials with boiling points higher than 1,4-BDO were removed from the 1,4-BDO-containing product stream from the bottom of the column, and a distillate was removed from the top of the column.

The third distillation column was configured to receive the distillate from the previous step in the base of the column, and for purified 1,4-BDO product to be removed as a liquid stream from the bottom of the column. This configuration would simulate a side-draw from a single distillation column. The 1,4-BDO product represents the condensed vapor product.

The feed rate was 7 liters/hr during the distillation. The column was operated at a pressure of 25 mmHg with a base temperature of 155° C. The purified 1,4-BDO product was collected by condensing the vapor stream from the bottom of the column.

Example 4

The distillation of Example 3 was repeated, but the column pressure of the second column was reduced to 10 mmHg.

Example 5

In Example 5, the third distillation column was used second time and used the purified 1,4-BDO product obtained from the distillation of Example 4. The added distillation simulates more stages in the second column of a two column distillation system. The column for the additional distillation is set up with the purified 1,4-BDO product of Example 4 as the feed at stage 11. The column was operated at 10 mmHg with a base temperature of 140° C. Materials with boiling points higher than 1,4-BDO were removed from the bottom of the column, and the second purified 1,4-BDO product was collected from the top of the column.

Example 6

Example 6 adds a hydrogenation treatment to the second purified 1,4-BDO product obtained from Example 5. The hydrogenation reaction used a RANEY-Ni catalyst and operated at 125° C. to 130° C. and a pressure of 400 psig to 600 psig ° C. The purified 1,4-BDO product is collected at the exit of the hydrogenation reactor.

Results of each of the Examples 3-6 are provided in Table 3. The purity of the purified 1,4-BDO product is >99.7% w/w in all examples. Examples 3 and 4 purified 1,4-BDO products had color. Examples 5 and 6 purified 1,4-BDO products were water clear. Other color bodies in the purified 1,4-BDO product are present in Examples 3-5 as indicated in the UV measurement at 270 nm, which are above the target of 0.1. The second purified 1,4-BDO product from Example 5 is the expected product of a 2 distillation column system with a side-draw to collect purified 1,4-BDO product from the second column. The purified 1,4-BDO product of Example 6 will be inherently lower in quality because light components such as THF are formed in the hydrogenation step. The results of the two column system provide a means to produce high purity 1,4 BDO product that is acceptable for many applications.

TABLE 3

Results of the Distillation Examples 3-6.

| Parameter | Example 3 | Example 4 | Example 5 | Example 6 | Target |
|---|---|---|---|---|---|
| UV at 270 nm | 0.88-1.5 | 0.18 | 0.4 | 0.013 | <0.1 |
| UV at 288 nm | 0.77-1.41 | 0.69 | — | 0.006 | — |
| UV at 308 nm | 0.55-1.02 | 0.43 | — | 0.002 | — |
| Appearance | Dark brown | Light yellow | Colorless | Colorless | <10 APHA |
| Water, ppm | 237 | 259 | — | — | <500 |
| 1,4-BDO, % | 99.83 | 99.87 | 99.86 | 99.73 | >99.7 |
| γ-butyrolactone, ppm | 14 | 4 | 7 | 490 | <100 |
| Unknowns, ppm | 188 | 249 | 257 | 364 | — |
| 1,4-BDO monoacetate, ppm | 70 | 21 | 32 | 24 | <300 |
| 2-(4'-hydroxybutoxy) tetrahydrofuran, ppm | 1037 | 828 | 816 | 1123 | <500 |
| 2-pyrrolidone, ppm | 5 | 9 | 9 | 8 | 2-5 |
| Tetrahydrofuran, ppm | 23 | 3 | 62 | 504 | — |

Examples 7-10

Modeling Two and Three Column Distillation Systems

In Examples 7-10, two and three column distillation systems were modeled using ASPEN-PLUS® simulation program.

Example 7

In ASPEN-PLUS® simulation program, a two-column distillation with side-draw was simulated. A first distillation column with 67 stages was set up to receive as feed the crude 1,4-BDO mixture at stage 1. A feed rate 2750 kg/hr was used in the model. The column was operated at a top pressure of 80 mmHg, a top temperature of 46.5-47° C., a base temperature of 169° C., with a reflux ratio of 1. Water and light materials (material with boiling points lower than 1,4-BDO) were removed from the crude 1,4-BDO mixture from the top of the first column. A 1,4-BDO-containing product stream was removed from the base of the first column.

A second distillation column with 67 stages was set up to receive as feed at stage 54 the 1,4-BDO-containing mixture that was obtained from the base of the first column. The second distillation column was operated at a top pressure of 22.5 mmHg, a top temperature of 134-137° C., a base temperature of 165° C., and a reflux ration of 37. Materials with boiling points higher than 1,4-BDO were removed from the 1,4-BDO-containing product stream from the bottom of the second distillation column, materials with boiling points lower than 1,4-BDO were removed from the top of the second distillation column and the distilled 1,4-BDO product was removed as a vapor and condensed from a side-draw located above the feed location of the second distillation column.

The two column distillation system with side-draw was then modeled in ASPEN-PLUS® simulation program using the feed composition given in Table 4 and produced the results presented in Table 4.

TABLE 4

Simulated results for a two column distillation system with side-draw.

| PARAMETERS | FEED | COLUMN 1 TOP | COLUMN 1 BASE | COLUMN 1 SIDE-DRAW |
|---|---|---|---|---|
| | | | | 1,4-BDO Containing Stream |
| Temp, deg C. | | 47-46.5 | 169 | |
| Press, mmHg | | 80 | 95 | |
| Mass Flow, kg/hr | 2750 | 418 (dist) | 2332 | |
| Reflux Ratio | | 1 | | |
| Mass Fraction | | | | |
| Water | 0.152 | | Trace | |
| 1,4-BDO | 0.825 | | 0.973 | |
| γ-butyrolactone | 0.001 | | 892 ppm | |
| Heavies | 0.02 | | 0.024 | |
| 1,4-BDO monoacetate | 0.001 | | 0.001 | |
| 2-(4'-hydroxybutoxy)THF | 0.001 | | 0.001 | |
| 2-pyrrolidone | 120 ppm | | 141 ppm | |
| Butanetriol | 50 ppm | | 59 ppm | |
| THF | 150 ppm | | trace | |
| 1,3-PDO | 100 ppm | | 0.275 | |

| | | COLUMN 2 | | |
|---|---|---|---|---|
| | | | | Product |
| Temp | 169 | 137-134 | 165.2 | 137 |
| Press, mmHg | | 22.5 | 37.5 | 23 |
| Mass Flow, kg/hr | 2332 | 58 (dist) | 79 | 2195 |
| Reflux Ratio | | 37 | | |
| Mass Fraction | | | | |
| Water | Trace | | | |
| 1,4-BDO | 0.973 | 0.952 | 0.293 | 0.998 |
| γ-butyrolactone | 892 ppm | 0.017 | Trace | 510 ppm |
| Heavies | 0.024 | Trace | 0.702 | Trace |
| 1,4-BDO monoacetate | 0.001 | 0.015 | 331 ppb | 869 ppm |
| 2-(4'-hydroxybutoxy)THF | 0.001 | 0.015 | 198 ppb | 879 ppm |
| 2-pyrrolidone | 141 ppm | Trace | 0.004 | 2 ppm |
| Butanetriol | 59 ppm | Trace | 0.002 | Trace |
| THF | Trace | | | |
| 1,3-PDO | 0.275 | 0.002 | 1 ppb | 81 ppb |

Example 8

The simulation in ASPEN-PLUS® simulation program of Example 7 was reconfigured to a two distillation column system and wiped-film evaporator, with the purified 1,4-BDO collected as a distillate from the second column. The wiped-film evaporator took as feed the materials with boiling points higher than 1,4-BDO along with 1,4-BDO from the bottom of the second distillation column. The wiped-film evaporator has a 1,4-BDO content from 70 to 95 wt % 1,4-BDO. The wiped-film evaporator was operated at a pressure of 4 mmHg to 7.5 mmHg and a temperature of 115° C. to 130° C. The distillate from the wiped-film evaporator was fed to the second distillation column feed stream or bottom to recovery the 1,4-BDO, and the high boiling residue was removed from the distillation system from the bottom of the wiped-film evaporator. Modeling of a two-column distillation system with a wiped-film evaporator was then carried out in ASPEN-PLUS® simulation program using a similar composition as in Example 7 without the 1,3 PDO. The simulation results indicated that recovery of 1,4-BDO from the crude 1,4-BDO mixture by the distillation system including the wiped-film evaporator will be greater than 99%.

Example 9

The simulation in ASPEN-PLUS® simulation program of Example 8 was reconfigured to a three distillation column with side-draw and wiped-film evaporator. A third distillation column was added to the end of the set-up described in Example 8 for a two distillation column system, and the third distillation column received as feed the 1,4-BDO-containing product stream from the distillate of the second distillation column, and a purified 1,4-BDO product was produced from a vapor side draw of the third distillation column. The side draw is located below the feed point of the third distillation column.

Materials with boiling points higher than 1,4-BDO were removed from the 1,4-BDO-containing product stream through the bottom of the second distillation column, The distillate of the second column was fed to the third distillation column Materials with boiling points lower than 1,4-BDO were removed from the top of the third distillation column. The purified 1,4-BDO product was removed as a vapor and condensed from a side-draw located below the feed location of the second distillation column.

Assuming a feed composition of 80% 1,4-BDO, 16% water, 0.2% gamma-butyrolactone, 0.05% 1,4-BDO monoacetate, 3% unidentified heavy material (material boiling higher than 1,4-BDO), and traces of 2-(4'-hydroxybutoxy)tetrahydrofuran and 2-pyrrolidone, operating conditions of the three column system with a side-draw and wiped-film evaporator were modeled in ASPEN-PLUS® simulation program. The results of the modeling are presented in Table 5. The simulation results indicated that recovery of 1,4-BDO from the crude 1,4-BDO mixture by the distillation system including the wiped-film evaporator will be greater than 98%.

TABLE 5

Results of ASPEN-PLUS ® simulation program of a Three Column System with Side-Draw.

|  | First Column (Dewater) | Third Column (Heavies) | Second Column (BDO Product) |
|---|---|---|---|
| # Stages in Rectification | 4 | 11 | 11 |
| # Stages in Stripping | 4 | 17 | 22 |
| Mass Distillate to Feed Ratio | 0.165 | 0.969 | 0.012 |
| Mass Bottoms to Feed Ratio | — | — | 0.019 |
| Molar Reflux Ratio | 1 | 1 | 210 |
| Boilup Ratio | 2.0 | 12.8 | 175 |
| Condenser Pressure, mbar | 107 | 30 | 33 |
| Condenser Temperature, C. | 45 | 137.2 | 119 |
| Condenser Duty, MW | 0.79 | 1.13 | 1.28 |
| Reboiler Pressure, mbar | 127 | 50 | 60 |
| Reboiler Temperature, C. | 169.2 | 160.7 | 152 |
| Reboiler Duty, MW | 1.08 | 1.06 | 1.86 |

Example 10

Production of 1,4-BDO with a Three Column System with Side-Draw

The following exemplifies how 1,4-BDO can be purified from a crude 1,4-BDO mixture using a three column distillation system similar to Example 9 with the addition of a Hydrogenation System located between the second and third distillation column. The components in the feed to the distillation are about 80 wt % 1,4-BDO, about 15 wt % water, 0.2 wt % γ-butyrolactone (GBL), 0.05 wt % 1,4-BDO monoacetate, 100 ppm 2-pyrrolidone (2P), 1000 ppm 2-(4'-hydroxybutoxy)tetrahydrofuran, 50 ppm butanetriol, 500 tetrahydrofuran and other unidentified heavy impurities. The first column separates water, the intermediate column separates the major portion of the heavy impurities (impurities with boiling points higher than 1,4-BDO) including 2P, and the second column separates GBL, 1,4-BDO monoacetate and the remaining impurities resulting in the purified 1,4-BDO product.

First Distillation Column (Dewatering Column)

The Dewatering column receives crude 1,4-BDO mixture as feed. The column separates water from the crude 1,4-BDO mixture. In addition to water, the column removes any residual ethanol and other volatile impurities. The distillate stream has more than 99.9 wt % of the initial water in the feed and is routed to the Waste Water Treatment Facility. The bottoms stream is the 1,4-BDO-containing product stream that is fed to the Heavies column.

The Dewatering column incorporates a falling film evaporator to effectively transfer the required heat for separation when there is minimal temperature difference between the process and available heating utility; otherwise, heat can be transferred to the column using alternate type heat exchangers. The overheads system includes a water cooled horizontal shell and tube heat exchanger that condenses the column overheads stream containing residual water and organics. The Dewatering column overhead operates at about 107 mbar.

Intermediate Distillation Column (Heavies Column)

The Heavies column separates heavy impurities (materials with boiling points higher than 1,4-BDO) from the 1,4-BDO-containing product stream from the Dewatering column bottom. The heavy impurities include residual sugar and salts, residual cellular material (proteins, amino acids etc.), BDO esters, sulfur and nitrogen containing compounds that contribute to UV-270 and other unknown high boiling impurities. The Heavies column also separates a major portion of the close boiling heavy impurities such as 2-pyrrolidone (2P). The distillate stream from the top of the column is the 1,4-BDO-containing product stream, and the bottoms stream contains the separated heavy impurities.

The Heavies Column incorporates a forced circulation evaporator to effectively transfer the heat with minimal fouling. The overhead system includes a falling film evaporator to economically condense the column overheads stream and provide low pressure steam to the evaporators. The Heavies column operates at 30 mbar. A wiped-film evaporator with low residence time is utilized to recover entrained 1,4-BDO from the high boiling column bottoms stream, and the distillate of the wiped-film evaporator is fed to the Heavies column.

Hydrogenation Reactor

Hydrogenation reactor is an intermediate polishing step that improves the quality of purified BDO by significantly removing color precursors. The system incorporates reactor beds that operate in a lead-lag configuration to enable continued operation when one of the beds is being switched out. The feed to hydrogenation is the Heavies distillate stream, and the product of hydrogenation feeds the BDO Column. The Hydrogenation System operates at 400 psig to 600 psig and 125° C. to 130° C.

Second Distillation Column (BDO Column)

The BDO column separates any remaining 2P, GBL, BDO monoacetate, and other trace, light impurities. 2P, GBL, and BDO monoacetate are important impurities in the 1,4-BDO product, and efficient separation of those components is critical to achieve the desired 1,4-BDO product purity. The distillate (light material) mainly contains GBL, and the bottoms stream (heavy materials) contains 2P. Purified 1,4-BDO product is collected as a vapor side-draw located below the feed to the BDO column. This location of the side-draw ensures 2P is dropped to the bottom, while separating the light impurities to the top of the column. The bottoms stream contains residual heavy impurities and is recycled to the Heavies Column.

The BDO column incorporates a falling film evaporator to effectively transfer the heat when there is minimal temperature difference between the process and available heating utility; otherwise, heat can be transferred to the column using alternate type heat exchangers. The overheads system includes a falling film evaporator to economically condense the column overheads stream and provide low pressure steam to the evaporators. A horizontal shell and tube condenser common to the Heavies and BDO column ensures stable operation of the overhead system in the event of an evaporator shutdown. The BDO column operates at 30 mbar. The distillate is combined with the Heavies bottoms stream.

Example 11

A Model of a Four-Column Distillation System with Side-Draw

A model for a four-column distillation system with side-draw includes in ASPEN-PLUS® simulation program was carried out. A first distillation column with 10 stages (including reboiler and condenser) and was set up to receive as feed the crude 1,4-BDO mixture at stage 6. A feed rate 3150 kg/hr was used in the model. The column was operated at a top pressure of 80 mmHg, a top temperature of 46.5-47° C., a base temperature of 169° C., with a reflux ratio of 1. Water and light materials (material with boiling points lower than 1,4-BDO) were removed from the crude 1,4-BDO mixture from the top of the first column. A 1,4-BDO-containing product stream was removed from the base of the first column.

A second distillation column with 30 stages (including condenser and reboiler) was set up to receive as feed at stage 12 the 1,4-BDO-containing product stream that was obtained from the base of the first column. The second distillation column was operated at a top pressure of 22.5 mmHg, a top temperature of 137° C., a base temperature of 160° C., and a reflux ration of 1. Materials with boiling points higher than 1,4-BDO were removed from the 1,4-BDO-containing product stream through the bottom of the second distillation column. A 1,4-BDO-containing product stream was removed as the distillate (overhead) of the second column. A wiped film evaporator was used to remove the higher boiler components of the materials with boiling points higher than 1,4-BDO from the bottom of the second distillation column and recycle the 1,4-BDO to the second distillation column feed.

A hydrogenation system containing a nickel-based catalyst was set up to receive as feed the distillate, the 1,4-BDO-containing product stream, of the second distillation column. Nickel based catalysts including NiSAT 310, BASF Ni 3276E, Raney 2486 and E 474 were tested. The system operates from 400 to 600 psig and 125 to 130° C. The hydrogenation system is as described in Example 10.

A third distillation column with 30 stages (including condenser and reboiler) was set up to receive as feed at stage 8 the 1,4-BDO-containing product stream that was obtained from the hydrogenation system. The third distillation column was operated at a top pressure of 25 mmHg, a top temperature of 133° C., a base temperature of 152° C., and a boilup ratio of 2.5. Materials with boiling points lower than 1,4-BDO were removed from the 1,4-BDO-containing product stream through the overhead of the third distillation column. A 1,4-BDO-containing product stream was removed from the bottom of the third column.

A fourth distillation column with 23 stages (including condenser and reboiler) was set up to receive as feed at stage 15 the 1,4-BDO-containing product stream from the bottom of the third column. The fourth distillation column was operated at a top pressure of 25 mmHg, a top temperature of 140° C., a based temperature of 148° C., and a Boilup Ratio of 74. The fourth distillation column removes residual lower boiling components than 1,4-BDO in the overhead and higher boiling components than 1,4-BDO in the bottoms. The overhead was recycled to the third column feed to recover 1,4 BDO, and the bottoms was recycle to the second column feed to also recover 1,4 BDO. The purified 1,4-BDO was taken as a side draw above the fourth column feed.

Example 12

Four-Column Distillation System with Wiped Film Evaporator

This example demonstrates that a four-column distillation system with a wiped film evaporator can significantly increase the percent recovery of 1,4-BDO, and the quality of the purified 1,4-BDO product.

A first distillation column with 8 stages using Koch 1Y packing, was set up to receive feed above stage 5, which was a crude 1,4-BDO mixture. A feed rate of 15 kg/hr was used. The column was operated at a top pressure of 80 mmHg, a top temperature of 46° C. to 47° C., a base temperature of 169° C., with a reflux ratio of 1. Water and light materials (material with boiling points lower than 1,4-BDO) were removed from the crude 1,4-BDO mixture from the top of the first distillation column. A first 1,4-BDO-containing product stream was removed from the base of the first distillation column.

A second distillation column with 18 stages using Koch 1Y packing, was set up to receive feed above stage 11, which was the first 1,4-BDO-containing product stream. The second distillation column was operated at a top pressure of 25 mmHg, a top temperature of 139° C. to 140° C., a base temperature of 148° C., and a reflux ratio of 1-1.5. Materials with boiling points higher than 1,4-BDO were removed from the first 1,4-BDO-containing product stream through the bottom of the second distillation column. A second 1,4-BDO-containing product stream was removed as the distillate (overhead) of the second distillation column.

A wiped film evaporator (WFE) was set up to receive as feed the materials with boiling points higher than 1,4-BDO from the bottom of the second distillation column. The WFE was operated a temperature from 120° C. to 125° C., an overhead temperature of 112° C. to 117° C. (cooled), a bottom temperature of 115° C. to 120° C., and at a pressure of 4.5 mmHg. Material collected from the overhead of the WFE was recycled to the second distillation column feed. Material that exited from the bottom of the WFE contained high boiling by-products.

A hydrogenation unit containing a nickel based catalyst was set up to treat the distillate of the second distillation column (i.e., the second 1,4-BDO-containing product stream). The hydrogenation system operated at a pressure of about 400 psig and a temperature of about 125° C. to 130° C.

A third distillation column with 18 stages using Koch 1Y packing, was set up to receive feed above stage 7, which was the second 1,4-BDO-containing product stream that was treated by the hydrogenation unit. The third distillation column was operated at a pressure of 25 mmHg, a top temperature of 100° C. to 109° C., a base temperature of 167° C. to 171° C., and a boilup ratio of about 1.5. Materials with boiling points lower than 1,4-BDO were removed from the 1,4-BDO-containing product stream through the overhead of the third distillation column. A third 1,4-BDO-containing product stream was removed from the bottom of the third distillation column.

A fourth distillation column with 18 stages using Koch 1Y packing, was set up to receive feed above stage 11, which was the third 1,4-BDO-containing product stream. The fourth distillation column was operated at a top pressure of 25 mmHg, a top temperature of 140° C. to 141° C., a based temperature of 146° C. to 148° C., and a boilup ratio of about 25 to 30. Materials with boiling points higher than 1,4-BDO were removed from the 1,4-BDO-containing product stream through the bottom of the fourth distillation column, and these materials with boiling points higher than 1,4-BDO were recycled to the second distillation column feed to recover 1,4-BDO. The purified 1,4-BDO product was taken as a distillate from the top of the fourth distillation column.

During the distillation of the 1,4-BDO in the present example, samples of process streams were taken at various points in the distillation and UV absorbance was measured. UV absorbance is a measure of the quality of the 1,4-BDO that indicates the amount of impurities present. These UV absorbances are compared to samples taken from a four column distillation system without a wiped film evaporator. The results are displayed in Table 6. With the addition of a wiped film evaporator to the distillation system, the amount of impurities was lowered and the quality of the product was increased in all cases as indicated by about a 50% reduction of the UV absorbances.

Also, percent recovery of 1,4-BDO in the present example for the second distillation column was measured during the distillation of different batches of material and averaged. The average percent recovery of 1,4-BDO was determined to be 98.1% when a wiped film evaporator was present, while the average percent recovery of 1,4-BDO in a system without a wiped film evaporator was determined to be 91.6%. A significant increase in the recovery of the 1,4-BDO was achieved, while improving the quality of the final product.

The inclusion of the wiped film evaporator helped to produce a purified 1,4-BDO product of higher purity and quality, while also helped to improve the amount of 1,4-BDO recovered by the distillation system.

TABLE 6

UV Distillation Results of a 4-column Distillation System with and without a Wiped Film Evaporator (WFE)

| | 2nd Distillation Column Distillate | | Hydrogenation Product | | 4th Distillation Column distillate (purified 1,4-BDO) | |
|---|---|---|---|---|---|---|
| | Without WFE | With WFE | Without WFE | With WFE | Without WFE | With WFE |
| Absorbance at 270 nm | 4.48 | 2.70 | 0.16 | 0.08 | 0.04 | 0.02 |
| Absorbance at 288 nm | 3.22 | 1.75 | 0.11 | 0.07 | 0.02 | 0.01 |
| Absorbance at 308 nm | 1.67 | 0.84 | 0.09 | 0.04 | 0.01 | 0.004 |

Example 13

This example demonstrates the high purity of the purified 1,4-BDO product that can be achieved following processes described herein.

1,4-BDO was produced directly from fermentation of glucose in dextrose using *E. coli* genetically engineered with a pathway converting glucose to 1,4-BDO. 1,4-BDO product was isolated from the fermentation broth. As explained below, samples of 1,4-BDO product from several exemplary runs were characterized.

Purity levels of the 1,4-BDO product samples were determined using a Gas Chromatography-Flame Ionization Detector (GC-FID) (AGILENT 7890; Agilent Technologies, Santa Clara, Calif. USA). 1,4-BDO product samples were diluted 1 to 1 with acetonitrile and injected into the gas chromatograph equipped with a bonded phase INNOWax type capillary column and a flame ionization detector. A majority of the impurities were separated from 1,4-BDO on the column and were detected by the FID. Calibration was performed by injecting known quantities of identified components at multiple amounts and allowing the software (CHROMPERFECT Software, Denville, N.J. USA) to calculate their FID response. Total unknowns were determined using a default response factor. The percent purity for 1,4-BDO was calculated by subtracting all known and unknown compounds from 100. The Response Factor (RF) was calculated as (Area of component/amount of component in calibration standard). The ppm of a component was calculated as the (Area of component/Response Factor)× (Dilution/Sample Amount). The method is applicable to the measurement of purity of >95% pure 1,4-BDO. Under the analytical conditions, retention time and response factor of various compounds were determined, including 12.84 RT for 1,4-BDO, 9.00 RT and 151.714 RF for furfural, 10.39 RT and 154.486 RF for gamma-butyrolactone (GBL) and 13.56 RT and 130.036 RF for solerone.

The 1,4-BDO content in the 1,4-BDO product samples ranged from 98.6 to 99.9 wt %. The samples were slightly acidic to near neutral with pH from about 6.5 to 6.8, colorless, and had American Public Health Association (APHA) color index values from 1 to 3. Total nitrogen was typically 1 to 1.5 ppm; 2-pyrrolidinone was typically 0 ppm or when occasionally observed was 1 to 2 ppm and accounted for the majority of the nitrogen. Several two carbon (C2) to four carbon (C4) mono-, di- and/or tri-ols were occasionally observed, generally from zero to 160 ppm total when present. Three carbon (C3) to six carbon (C6) carbonyl compounds were observed at about 0 to 200 ppm total, accounted for largely by a C3 carbonyl compound. The C4 carbonyl GBL was usually at 0 ppm, and when rarely observed was at 1 to 90 ppm. The five carbon (C5) carbonyls, including N-methyl-2-pyrrolidinone and furfural, were usually 0 ppm, but furfural when occasionally present was from 3 to 10 ppm, and rarely at 20 or 30 ppm. The C6 carbonyls, including solerone, pantolactone and 5-hydroxymethyl-furfural were usually at 0 ppm, and when occasionally observed were at 3 to 9 ppm total.

TABLE 7

Charactistics of Exemplary 1,4-BDO Product Samples

| | Exemplary 1,4-BDO Product Sample | | | | | |
|---|---|---|---|---|---|---|
| | A | B | C | D | E | F |
| 1,4-BDO (w/w %) | 99.84 | 99.90 | 99.81 | 98.70 | 98.69 | 99.84 |
| Hunter Color (APHA) | colorless | colorless | colorless | 1.50 | 2.19 | colorless |
| Moisture (ppm) | 465.00 | 84.00 | 296.00 | 385.00 | 128.00 | 298.00 |
| Total Nitrogen (ppm) | 3 | 1.5 | N.D. | 1.40 | 1.30 | N.D. |
| Non-carbonyl furanyls (ppm) | 680.00 | 845.00 | 1411.00 | 2409.00 | 2797.00 | 1229.00 |

TABLE 7-continued

Charactistics of Exemplary 1,4-BDO Product Samples

Exemplary 1,4-BDO Product Sample

| | A | B | C | D | E | F |
|---|---|---|---|---|---|---|
| 1-Methyl-2-Pyrrolidinone (ppm) | 0.00 | 0.00 | 0.00 | 0.00 | 0.00 | 0.00 |
| 2-Pyrrolidinone (ppm) | 0.00 | 0.00 | 2.00 | 0.00 | 0.00 | 0.00 |
| C2-C4 mono-, di-, tri-ols (ppm) | 90.00 | 4.00 | 0.00 | 125.00 | 81.00 | 0.00 |
| C3 Acetate compound (ppm) | 30.00 | 2.00 | 3.00 | 0.00 | 0.00 | 2.00 |
| C3 carbonyl (ppm) | 20.00 | 53.00 | 90.00 | 77.00 | 132.00 | 88.00 |
| GBL (ppm) | 0.00 | 1.00 | 7.00 | 0.00 | 0.00 | 0.00 |
| 5-Hydroxy-methyl Furfural (ppm) | 0.00 | 0.00 | 0.00 | 0.00 | 0.00 | 0.00 |
| Furfural (ppm) | 20.00 | 0.00 | 3.00 | 0.00 | 0.00 | 0.00 |
| Pantolactone (ppm) | 0.00 | 0.00 | 0.00 | 0.00 | 0.00 | 0.00 |
| Solerone (ppm) | 0.00 | 3.00 | 6.00 | 0.00 | 3.00 | 5.00 |

Example 14

This example describes studies using a four column distillation system. In short, a crude 1,4-BDO mixture was fed to a first "dewater" distillation column to remove low-boilers, including water. The high boilers (1,4-BDO-containing product stream) from the dewater column was fed to a second "heavies" distillation column to produce a low-boilers distillate (1,4-BDO containing product stream) and a bottoms purge. The 1,4-BDO containing product stream from the heavies column was fed to a hydrogenation unit and then fed to a third "lights" column which produced a liquid 1,4-BDO containing product stream that was in turn fed to a fourth "BDO" column. 1,4-BDO product from the four column distillation system was obtained as the distillate from the BDO column. Studies were conducted to assess how impurities in the 1,4-BDO containing product stream from the heavies column could be reduced with minimal loss in recovery of 1,4-BDO from the system. UV (270 nm) absorbance measurements were made to assess the relative amounts of impurities in process streams and product from the four column distillation system. Reducing UV absorbing impurities in the process stream fed to the hydrogenation unit, in addition to increasing the percent 1,4-BDO in a product, can also beneficially increase the catalyst life in the hydrogenation unit.

The initial four column set up was such that the bottoms purge from the heavies column was fed to a forced recirculation reboiler, the vapor of which was recycled into the heavies column (the "no WFE" condition). Different feed rates to, and bottoms purge rates from, the heavies column were undertaken to observe if the purge/feed ratios would reduce impurities in the 1,4-BDO distillate from the BDO column. The same four column set up was used where a portion of the bottoms purge was subjected to wiped-film evaporation, the distillate of which was introduced back into the heavies column or a 1,4-BDO product stream (prior to the hydrogenation unit) of the four column distillation system (the "WFE present" condition).

In particular, the effect of changing the bottoms purge rate from the heavies column on UV 270 absorbance of the 1,4-BDO product from the BDO column was examined.

Purge rates between about 0.30 kg/hr and about 0.90 kg/hr were examined. The UV 270 absorbance of the 1,4-BDO product from the BDO column was above 0.0300 at a purge rate of about 0.3 kg/hr (with no WFE), which was reduced by increasing the purge rate. In these studies, it was observed that, with respect to the heavies column, a bottoms purge rate that is about one tenth of the feed rate would often be near, or be, an optimum ratio to reduce UV absorbing impurities in the 1,4-BDO product. Increasing the heavies column bottoms purge rate might also be associated with a loss in recovery of 1,4-BDO product. Adding a vertical WFE at purge rates above 0.7 kg/hr contributed to the reduction of UV 270 aborbing contaminants. Using a WFE was also observed to be useful for avoiding the loss in percent recovery of 1,4-BDO in the product, for example, when increased bottoms purge rates were used.

Other studies were conducted to assess effects of using a horizontal wiped film evaporator in a BDO process stream, rather than a vertical wiped film evaporator, such as used in the studies described above and in Example 12. The presence of 2-pyrrolidone in a BDO process stream was used as an indicator of the extent of UV 270 absorbing color components in the stream. In these studies, determinations of 2-pyrrolidone concentrations (in ppm) and actual mass rates (kg/hr) were made to assess the likely presense of color components in the WFE distillate. Comparisons were made where horizontal WFE was conducted at various operation temperatures ranging between about 122° C. and 170° C. Results of the studies demonstrated that horizontal WFE operating temperatures below about 160° C., with an optimum operating film temperature from about 145° C. to about 155° C., was effective in reducing 2-pyrrolidone. In these studies it was noted that BDO monoacetate and THF remain relatively unchanged in the WFE distillate at the various WFE operating temperatures. Specifically, 2-pyrrolidone decreased in the WFE distillate as operating temperatures increased up to about 155° C., and then 2-pyrrolidone increased as the film temperature increased above 155° C. These studies demonstrate the usefulness of using horizontal WFE in BDO purification systems and processes such as described herein.

Example 15

A number of tests and modeling runs on ASPEN on a 4 distillation column system were made in order to determine the operating conditions ranges. Depending on the feed composition and separation across each column, distillations can be operated within the exemplary ranges given below.

TABLE 6

Exemplary Distillation 4 Column Operating Design Parameters

| | D/F* | B/F** |
|---|---|---|
| Dewater | 0.05-0.3 | 0.80-0.90 |
| Heavies | 0.75-0.99 | 0.1-0.02 |
| Lights | 0.001-0.05 | 0.95-0.997 |
| BDO | 0.001-0.05 | 0.001-0.1 |

*D/F means Distillate over Feed
**B/F means Bottoms over Feed

It is understood that modifications which do not substantially affect the activity of the various embodiments of this invention are also included within the definition of the invention provided herein. Accordingly, the examples presented herein are intended to illustrate but not limit the present invention.

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific examples and studies detailed above are only illustrative of the invention. It should be understood that various modifications can be made without departing from the spirit of the invention. Accordingly, the invention is limited only by the following claims.

What is claimed is:

1. A process of purifying 1,4-butanediol (1,4-BDO) comprising:
   (a) subjecting a crude 1,4-BDO mixture to a first column distillation procedure to remove materials with a boiling point lower than 1,4-BDO from the crude 1,4-BDO mixture to produce a first 1,4-BDO-containing product stream;
   (b) subjecting the first 1,4-BDO-containing product stream to a first intermediate column distillation procedure to remove materials with a boiling point higher than 1,4-BDO, as a first high boilers stream, to produce a second 1,4-BDO-containing product stream exiting from the top of the first intermediate column, and treating the second 1,4-BDO-containing product stream with a hydrogenation reaction prior to step (d);
   (c) subjecting the first high-boilers stream to wiped-film evaporation (WFE) to produce a WFE distillate and subjecting the WFE distillate to step (b);
   (d) subjecting the second 1,4-BDO-containing product stream to a second intermediate column distillation procedure to remove materials with a boiling point lower than 1,4-BDO, to produce a third 1,4-BDO-containing product stream; and
   (e) subjecting the third 1,4-BDO-containing product stream to a second column distillation procedure to remove materials with boiling points higher than 1,4-BDO as a second high-boilers stream, to produce a purified 1,4-BDO product;
   wherein the crude 1,4-BDO mixture comprises 80% to 85% 1,4-BDO with 1% to 25% water; recovery of the purified 1,4-BDO product from the crude 1,4-BDO mixture is greater than 98%; and the purified 1,4-BDO product is greater than 98% (w/w) 1,4-BDO.

2. The process of claim 1, wherein the purified 1,4-BDO product is collected as a distillate of the second column distillation procedure.

3. The process of claim 1 further comprising culturing a modified non-naturally occurring organism to produce 1,4-BDO in a fermentation broth, subjecting the fermentation broth to a separation procedure to obtain a separated 1,4-BDO product, and subjecting the separated 1,4-BDO product to water removal and salt removal to produce the crude 1,4-BDO mixture, wherein the separation procedure consists of a first filtration and a second filtration, wherein the first filtration is microfiltration or ultrafiltration, and wherein the second filtration is nanofiltration.

4. The process of claim 3 further comprising subjecting the crude 1,4-BDO mixture to a polishing ion exchange using a polishing ion exchange resin that is an anion exchange resin.

5. The process of claim 3, wherein the water removal is by evaporation.

6. The process of claim 3, wherein the salt removal is by primary ion exchange.

7. The process of claim 6, wherein the primary ion exchange resin comprises a cation exchange resin and a anion exchange resin.

8. The process of claim 1, wherein the purified 1,4-BDO product is collected from a side draw of the second column distillation procedure.

9. The process of claim 1, wherein the purified 1,4-BDO product has less than 0.04 percent 2-(4-hydroxybutoxy) tetrahydrofuran.

* * * * *